(12) United States Patent
Kim et al.

(10) Patent No.: US 9,882,149 B2
(45) Date of Patent: Jan. 30, 2018

(54) COMPOUND FOR ORGANIC OPTOELECTRIC DEVICE, ORGANIC OPTOELECTRONIC DEVICE COMPRSING SAME, AND DISPLAY APPARATUS COMPRISING ORGANIC OPTOELECTRIC DEVICE

(71) Applicant: SAMSUNG SDI CO., LTD., Yongin-si, Gyeonggi-do (KR)

(72) Inventors: Hyung-Sun Kim, Suwon-si (KR); Wook Kim, Suwon-si (KR); Chang-Woo Kim, Suwon-si (KR); Mi-Young Chae, Suwon-si (KR); Dal-Ho Huh, Suwon-si (KR); Eun-Sun Yu, Suwon-si (KR); Moo-Jin Park, Suwon-si (KR)

(73) Assignee: Samsung SDI Co., Ltd., Yongin-si, Gyeonggi-do (KR)

( * ) Notice: Subject to any disclaimer, the term of this patent is extended or adjusted under 35 U.S.C. 154(b) by 602 days.

(21) Appl. No.: 14/390,570

(22) PCT Filed: Jul. 4, 2013

(86) PCT No.: PCT/KR2013/005954
§ 371 (c)(1),
(2) Date: Oct. 3, 2014

(87) PCT Pub. No.: WO2014/007565
PCT Pub. Date: Jan. 9, 2014

(65) Prior Publication Data
US 2015/0090974 A1 Apr. 2, 2015

(30) Foreign Application Priority Data

Jul. 4, 2012 (KR) .................. 10-2012-0073091
Nov. 6, 2012 (KR) .................. 10-2012-0124963

(51) Int. Cl.
| | | |
|---|---|---|
| *C07D 401/14* | (2006.01) | |
| *C09K 11/06* | (2006.01) | |
| *C07F 15/00* | (2006.01) | |
| *C07F 7/08* | (2006.01) | |
| *H01L 51/50* | (2006.01) | |
| *H05B 33/14* | (2006.01) | |
| *H01L 51/00* | (2006.01) | |

(52) U.S. Cl.
CPC ...... *H01L 51/0085* (2013.01); *C07F 15/0033* (2013.01); *C09K 11/06* (2013.01); *H01L 51/0094* (2013.01); *H01L 51/5028* (2013.01); *C09K 2211/1007* (2013.01); *C09K 2211/1029* (2013.01); *C09K 2211/185* (2013.01); *H01L 51/006* (2013.01); *H01L 51/0072* (2013.01); *H01L 51/0081* (2013.01); *H01L 51/5016* (2013.01)

(58) Field of Classification Search
CPC ............ C07F 15/003377; C07F 7/0814; C07F 15/0033; C09K 11/06; H01L 51/5032; H05B 33/14
USPC .................................. 546/4; 257/40, E51.046
See application file for complete search history.

(56) References Cited

U.S. PATENT DOCUMENTS

2008/0074033 A1  3/2008  Ionkin et al.
2011/0278555 A1  11/2011  Inoue et al.

FOREIGN PATENT DOCUMENTS

| CN | 100362007 C | 1/2008 |
|---|---|---|
| CN | 101508673 A | 8/2009 |
| CN | 101525354 A | 9/2009 |
| CN | 101535325 A | 9/2009 |
| CN | 101538290 A | 9/2009 |
| CN | 101550167 A | 10/2009 |
| EP | 2 182 002 A1 | 5/2010 |
| EP | 2182002 A1 | 5/2010 |
| EP | 2 568 030 A2 | 3/2013 |
| JP | 2008-137994 | 6/2008 |
| JP | 4474493 B1 | 6/2010 |
| JP | 4500364 B1 | 7/2010 |
| KR | 10-2006-0029866 A | 4/2006 |
| KR | 10-2009-0001071 A | 1/2009 |
| KR | 10-2009-0001072 A | 1/2009 |
| KR | 10-0880220 B1 | 1/2009 |
| KR | 10-0880224 B1 | 1/2009 |
| KR | 10-2011-0122051 A | 11/2011 |
| KR | 10-2012-0057561 A | 6/2012 |
| WO | WO-2008/056799 A1 | 5/2008 |
| WO | WO 2008/073440 A2 | 6/2008 |
| WO | WO 2012/015274 A2 | 2/2012 |
| WO | WO-2012/023947 A1 | 2/2012 |
| WO | WO-2012/057138 A1 | 5/2012 |

OTHER PUBLICATIONS

Lee, et al., "Improved Performance of Solution-Processable OLEDs by Silyl Substitution to Phosphorescent Iridium Complexes", Synthetic Metals 162 (2012)1961-1967.
Chinese Search Report dated Sep. 15, 2015 in Corresponding Chinese Patent Application No. 201380033478.8.
Extended European Search Report dated Jan. 25, 2016 in Corresponding European Patent Application No. 13813173.5.
Jung, et al., "A Green Emitting Iridium(III) Complex with Narrow Emission Band and Its Application to Phosphorescence Organic Light-Emitting Diodes (OLEDs)" Organic Electronics 10 (2009) 1066-1073.
Extended European Search Report dated Mar. 4, 2016 in Corresponding European Patent Application No. 13812616.4.

*Primary Examiner* — Venkataraman Balasubramanian
(74) *Attorney, Agent, or Firm* — Lee & Morse, P.C.

(57) ABSTRACT

Provided is a compound for an organic optoelectric device, an organic light emitting diode including the same, and a display device including the organic light emitting diode, wherein the compound for an organic optoelectric device is represented by Chemical Formula 1. The Chemical Formula 1 and description thereof are the same as described in the specification.

14 Claims, 1 Drawing Sheet

COMPOUND FOR ORGANIC OPTOELECTRIC DEVICE, ORGANIC OPTOELECTRONIC DEVICE COMPRSING SAME, AND DISPLAY APPARATUS COMPRISING ORGANIC OPTOELECTRIC DEVICE

TECHNICAL FIELD

A compound for an organic optoelectric device, an organic light emitting diode including the same, and a display device including the organic light emitting diode are disclosed.

BACKGROUND ART

An organic optoelectric device is a device requiring a charge exchange between an electrode and an organic material by using holes or electrons.

An organic optoelectric device may be classified as follows in accordance with its driving principles. A first organic optoelectric device is an electronic device driven as follows: excitons are generated in an organic material layer by photons from an external light source; the excitons are separated into electrons and holes; and the electrons and holes are transferred to different electrodes as a current source (voltage source).

A second organic optoelectric device is an electronic device driven as follows: a voltage or a current is applied to at least two electrodes to inject holes and/or electrons into an organic material semiconductor positioned at an interface of the electrodes, and the device is driven by the injected electrons and holes.

Examples of an organic optoelectric device include an organic photoelectric device, an organic light emitting diode, an organic solar cell, an organic photo conductor drum, an organic transistor, and the like, which require a hole injecting or transport material, an electron injecting or transport material, or a light emitting material.

Particularly, an organic light emitting diode (OLED) has recently drawn attention due to an increase in demand for flat panel displays. In general, organic light emission refers to conversion of electrical energy into photo-energy.

Such an organic light emitting diode converts electrical energy into light by applying current to an organic light emitting material. It has a structure in which a functional organic material layer is interposed between an anode and a cathode. Herein, the organic material layer includes a multi-layer including different materials, for example a hole injection layer, a hole transport layer, an emission layer, an electron transport layer, and an electron injection layer, in order to improve efficiency and stability of an organic light emitting diode.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material may be used for a light emitting material of an organic light emitting diode in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect. Therefore, a host/dopant system is included as a light emitting material in order to improve color purity and increase luminous efficiency and stability through energy transfer.

In order to implement excellent performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting diode has thus far not been satisfactory and thus there is a need for a novel material. This material development is also required for other organic optoelectric devices.

The low molecular organic light emitting diode is manufactured as a thin film in a vacuum deposition method and can have good efficiency and life-span performance, and a polymer organic light emitting diode is manufactured in an inkjet or spin coating method has an advantage of low initial cost and being large-sized.

Both low molecular organic light emitting and polymer organic light emitting diodes have an advantage of self-light emitting, high speed response, wide viewing angle, ultra-thin, high image quality, durability, large driving temperature range, and the like. In particular, they have good visibility due to self-light emitting characteristics compared with a conventional LCD (liquid crystal display) and have an advantage of decreasing a thickness and weight of LCD up to a third, because they do not need a backlight.

In addition, since they have a response speed 1000 time faster microsecond unit than LCD, they can realize a perfect motion picture without after-image. Accordingly, based on these advantages, they have been remarkably developed to have 80 times efficiency and more than 100 times life-span since they come out for the first time in the late 1980s, and recently, they keep being rapidly larger such as a 40-inch organic light emitting diode panel.

They are simultaneously required to have improved luminous efficiency and life-span in order to be larger. Therefore, there are needs for developments for a stable and efficient organic material layer material for an organic light emitting diode.

DISCLOSURE

Technical Problem

A composition for an organic optoelectric device being capable of providing an organic optoelectric device having characteristics such as high efficiency, long life-span and the like may be provided.

An organic light emitting diode including the compound for an organic optoelectric device and a display device including the organic light emitting diode are provided.

Technical Solution

In one embodiment of the present invention, a compound represented by the following Chemical Formula 1 for an organic optoelectric device is represented.

[Chemical Formula 1]

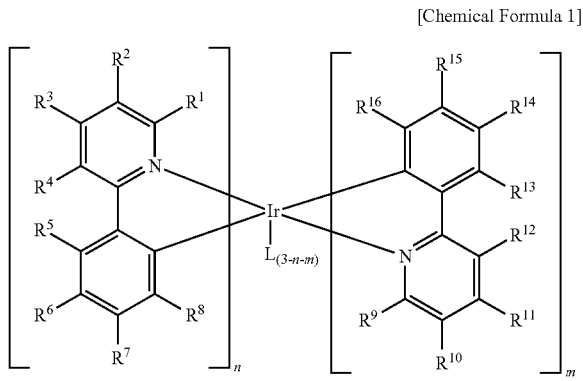

In the above Chemical Formula 1, $R^1$ to $R^{16}$ are independently hydrogen, deuterium, a substituted or unsubstituted C1 to C10 alkyl group, a substituted or unsubstituted C6 to C20 aryl group, or —$SiR^{17}R^{18}R^{19}$, wherein the $R^{17}$ to $R^{19}$ are independently a substituted or unsubstituted C1 to C6 alkyl group.

One of $R^1$ to $R^8$ is a functional group represented by the following Chemical Formula 2, and another of the $R^1$ to $R^8$ is —$SiR^{17}R^{18}R^{19}$. In addition, one of $R^9$ to $R^{16}$ is a functional group represented by the following Chemical Formula 2, and another of the $R^9$ to $R^{16}$ is —$SiR^{17}R^{18}R^{19}$.

L is a bidentate ligand of a monovalent anion, and is a ligand coordination-bonding with iridium through a unshared electron pair of carbon or heteroatom, and n and m are independently integers of 0 to 3, and n+m is one of integers of 1 to 3.

[Chemical Formula 2]

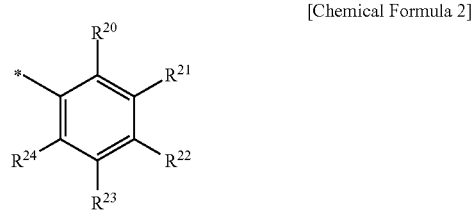

In the above Chemical Formula 2, $R^{20}$ to $R^{24}$ are independently hydrogen, deuterium, a substituted or unsubstituted C1 to C10 alkyl group, or a substituted or unsubstituted C6 to C20 aryl group, and * denotes position bonding with a carbon atom.

In another embodiment of the present invention, an organic optoelectric device includes an anode, a cathode, and at least one or more organic thin layer between the anode and the cathode, and at least one of the organic thin layers may include the compound for an organic optoelectric device.

The organic thin layer may be an emission layer.

The compound for an organic optoelectric device may be used as a dopant in an emission layer.

In yet another embodiment of the present invention, a display device including the organic light emitting diode is provided.

Advantageous Effects

An organic optoelectric device including the compound for an organic optoelectric device has excellent electrochemical and thermal stability and life-span characteristic, and has high luminous efficiency at a low driving voltage. The compound for an organic optoelectric device may be desirable for a solution process.

MODE FOR INVENTION

Figure 1:
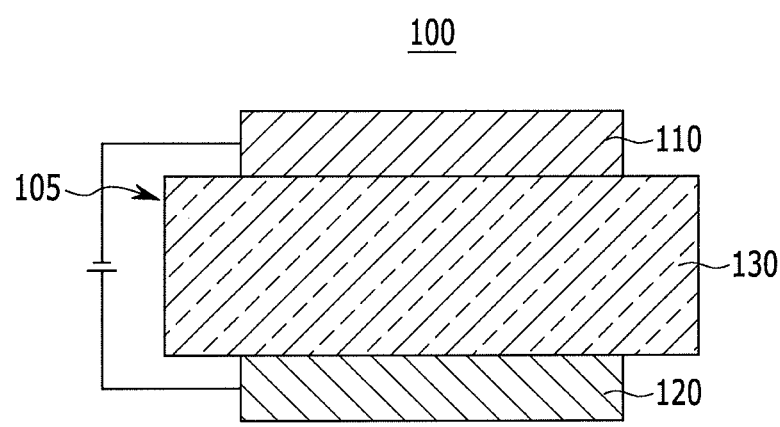
FIGS. 1 and 2 are cross-sectional views showing organic light emitting diodes according to various embodiments of the present invention including the compounds for an organic optoelectric device according to one embodiment of the present invention.

Hereinafter, embodiments of the present invention are described in detail. However, these embodiments are exemplary, and the present invention is not limited thereto and is limited by the claims.

In the present specification, when a definition is not otherwise provided, "substituted" refers to one substituted with deuterium, a halogen, a hydroxy group, an amino group, a substituted or unsubstituted C1 to C30 amine group, a nitro group, a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like, or a cyano group, instead of at least one hydrogen of a substituent or a compound.

The two adjacent substituent of the substituted halogen, hydroxy group, an amino group, a substituted or unsubstituted C1 to C20 amine group, a nitro group, a substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group and the like, or cyano group may be fused to form a ring.

In the present specification, when specific definition is not otherwise provided, "hetero" refers to one including 1 to 3 hetero atoms selected from N, O, S, and P, and remaining carbons in one functional group.

In the present specification, when a definition is not otherwise provided, "alkyl group" refers to an aliphatic hydrocarbon group. The alkyl group may be a saturated alkyl group without any double bond or a triple bond.

The alkyl group may be a C1 to C20 alkyl group. More specifically, the alkyl group may be a C1 to C10 alkyl group or a C1 to C6 alkyl group. For example, a C1 to C4 alkyl group may have 1 to 4 carbon atoms in alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group a cyclopropyl group, a cyclobutyl group, a cyclopentyl group, a cyclohexyl group, and the like.

"Aryl group" refers to a cyclic functional group where all elements have p-orbitals, and these p-orbitals forms conjugation and includes monocyclic or fused ring polycyclic (i.e., rings sharing adjacent pairs of carbon atoms) groups.

A "heteroaryl group" refers to aryl group including 1 to 3 hetero atoms selected from N, O, S, and P, and remaining carbons. When the heteroaryl group is a fused ring, each ring may include 1 to 3 hetero atoms.

More specifically, the substituted or unsubstituted aryl group and/or a substituted or unsubstituted heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof, but are not limited thereto.

In the present specification, hole characteristics refer to characteristics that holes formed in the anode is easily injected into the emission layer and transported in the emission layer due to conductive characteristics according to HOMO level. More specifically, it is similar to electron-repelling characteristics.

Electron characteristics refer to characteristics that electron formed in the cathode is easily injected into the emission layer and transported in the emission layer due to conductive characteristics according to LUMO level. More specifically, it is similar to electron-withdrawing characteristics.

In one embodiment of the present invention, a compound represented by the following Chemical Formula 1 for an organic optoelectric device is provided.

[Chemical Formula 1]

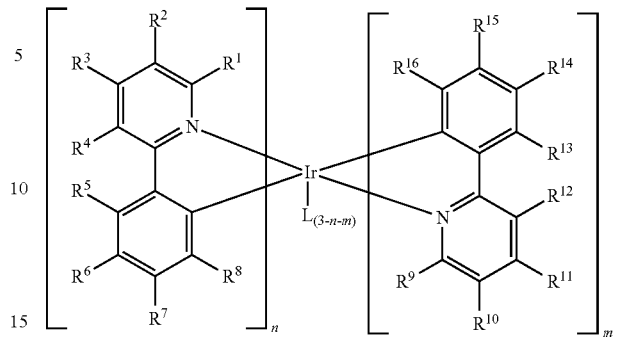

In the above Chemical Formula 1, $R^1$ to $R^{16}$ are independently hydrogen, deuterium, a substituted or unsubstituted C1 to C10 alkyl group, a substituted or unsubstituted C6 to C20 aryl group, or —$SiR^{17}R^{18}R^{19}$, wherein the $R^{17}$ to $R^{19}$ are independently a substituted or unsubstituted C1 to C6 alkyl group.

One of $R^1$ to $R^8$ is a functional group represented by the following Chemical Formula 2, and another of the $R^1$ to $R^8$ is —$SiR^{17}R^{18}R^{19}$. In addition, one of $R^9$ to $R^{16}$ is a functional group represented by the following Chemical Formula 2, and another of the $R^9$ to $R^{16}$ is —$SiR^{17}R^{18}R^{19}$.

L is a bidentate ligand of a monovalent anion, and is a ligand coordination-bonding with iridium through a unshared electron pair of carbon or heteroatom, and n and m are independently integers of 0 to 3, and n+m is one of integers of 1 to 3.

[Chemical Formula 2]

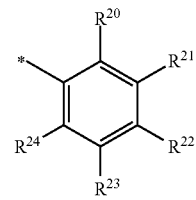

The above Chemical Formula 2 is a form of a substituted or unsubstituted phenyl group, and in Chemical Formula 2, $R^{20}$ to $R^{24}$ are independently hydrogen, deuterium, a substituted or unsubstituted C1 to C10 alkyl group, or a substituted or unsubstituted C6 to C20 aryl group, and * denotes a position bonding with a carbon atom.

The compound represented by the above Chemical Formula 1 for an organic optoelectric device necessarily has a substituted or unsubstituted phenyl group represented by the above Chemical Formula 2 in a main ligand having a 2-phenylpyridine backbone and also, necessarily —$SiR^{17}R^{18}R^{19}$. The main ligand is marked as a combination No. n or m among the ligands having a coordination bond with iridium.

Herein, the compound represented by the above Chemical Formula 1 for an organic optoelectric device may have excellent heat resistance stability and life-span characteristics and high luminous efficiency at a low driving voltage.

In general, a device manufactured by using a phosphorescent material has a drawback of sharply decreased efficiency by an extinction phenomenon due to saturation of a triplet exited state at a high current density. This drawback may be overcome by introducing a very bulky substituent into a luminous material or making the luminous material have a branch having a dendrimer structure to prevent the triplet-triplet extinction phenomenon.

According to one embodiment, a dopant as the luminous material has decreased interactions among molecules due to introduction of —$SiR^{17}R^{18}R^{19}$ and a phenyl group having large steric hindrance and thus, is prevented from the triplet-triplet extinction phenomenon and may realize a device having very excellent life-span and luminous efficiency. In addition, the introduction of a bulky substituent decreases interactions among molecules and thus, may have an effect on decreasing a deposition temperature.

In the above Chemical Formula 1, one main ligand has one —$SiR^{17}R^{18}R^{19}$.

For example, in the above Chemical Formula 1, n may be an integer of 1 to 3, one of $R^1$ to $R^4$ may be —$SiR^{17}R^{15}R^{19}$, and the rest of $R^1$ to $R^4$ may be independently hydrogen, deuterium, or a substituted or unsubstituted C1 to C10 alkyl group. At the same time, one of $R^5$ to $R^8$ may be the functional group represented by the above Chemical Formula 2, and the rest of $R^5$ to $R^8$ may be independently hydrogen, deuterium, or a substituted or unsubstituted C1 to C10 alkyl group. In this case, the compound for an organic optoelectric device may realize excellent heat resistance stability, life-span characteristics and luminous efficiency. The introduction of a bulky substituent such as the —$SiR^{17}R^{18}R^{19}$ and the phenyl group may make a ligand have an overall three dimensional shape, and accordingly, a dopant as a luminous material also has a bulky three dimensional structure suppressing interactions among molecules and thus, may realize a device having excellent life-span characteristics and luminous efficiency.

For specific examples, in the above Chemical Formula 1, n may be an integer of 1 to 3, $R^2$ is —$SiR^{17}R^{18}R^{19}$, $R^6$ is a phenyl group, and $R^1$, $R^3$ to $R^5$, $R^7$ and $R^8$ may be independently hydrogen, deuterium, or a substituted or unsubstituted C1 to C10 alkyl group. In this case, the compound for an organic optoelectric device has improved heat resistance stability, life-span characteristic and luminous efficiency.

When a phenyl group is substituted at the $R^6$, the phenyl group does not only change color purity of green luminescence but also increases entire volume of molecules and thus, minimizes interactions among the molecules, resultantly realizing a light emitting device having high efficiency and a long life-span.

For another example, in the above Chemical Formula 1, n may be an integer of 1 to 3, one of $R^1$ to $R^4$ may be the functional group represented by the above Chemical Formula 2, another of the $R^1$ to $R^4$ may be —$SiR^{17}R^{18}R^{19}$, and the rest of $R^1$ to $R^4$ and $R^5$ to $R^8$ may be independently hydrogen, deuterium, or a substituted or unsubstituted C1 to C10 alkyl group. Herein, the —$SiR^{17}R^{18}R^{19}$ and the functional group represented by Chemical Formula 2 may be bonded at an ortho, meta, or para position.

For specific examples, in the above Chemical Formula 1, n may be an integer of 1 to 3, $R^2$ is a phenyl group, $R^3$ is —$SiR^{17}R^{18}R^{19}$, and $R^1$, $R^4$ to $R^8$ may be independently hydrogen, deuterium, or a substituted or unsubstituted C1 to C10 alkyl group. In this case, the compound for an organic optoelectric device has improved heat resistance stability, life-span characteristic and luminous efficiency.

For another example, in the above Chemical Formula 1, n may be an integer of 1 to 3, one of $R^1$ to $R^4$ may be —$SiR^{17}R^{18}R^{19}$, and the rest of $R^1$ to $R^4$ may be independently hydrogen, deuterium, or a substituted or unsubstituted C1 to C10 alkyl group. At the same time, one of $R^5$ to $R^8$ may be the functional group represented by the above Chemical Formula 2, and the rest of $R^5$ to $R^8$ may be independently hydrogen, deuterium, or a substituted or unsubstituted C1 to C10 alkyl group. At the same time, m may be an integer of 1 to 3, one of $R^9$ to $R^{12}$ may be the functional group represented by the above Chemical Formula 2, another of the $R^9$ to $R^{12}$ may be —$SiR^{17}R^{18}R^{19}$, and the rest of $R^9$ to $R^{12}$ and $R^{13}$ to $R^{16}$ may be independently hydrogen, deuterium, or a substituted or unsubstituted C1 to C10 alkyl group.

Herein, the —$SiR^{17}R^{18}R^{19}$ and the functional group represented by Chemical Formula 2 may be bonded at an ortho, meta, or para position.

In the above Chemical Formula 1, n may be an integer of 1 to 3, at least one of $R^1$ to $R^8$ may be a substituted or unsubstituted C1 to C20 alkyl group, specifically a unsubstituted C1 to C10 alkyl group, for example a methyl group. In this case, thermal stability may be improved.

In the —$SiR^{17}R^{18}R^{19}$, the $R^{17}$ to $R^{19}$ may be independently a methyl group. That is to say, the —$SiR^{17}R^{18}R^{19}$ may be a trimethylsilyl group. In this case, the compound for an organic optoelectric device may realize improved heat resistance stability, life-span characteristic and luminous efficiency.

In the above Chemical Formula 1, n+m may be 3. In the above Chemical Formula 1, n or m may be 3. This means that in Chemical Formula 1, the ligand represented by L is not included. In this case, its synthesis becomes easier and the compound may be stabilized. Accordingly, a light emitting device having life-span characteristics may be provided.

In the above Chemical Formula 1, n+m may be 1 or 2. This means that in Chemical Formula 1, at least one of the ligand represented by L is included. In this case, a color tuning of the compound may be possible.

In the above Chemical Formula 1, L is an auxiliary ligand, and may be selected from the following Chemical Formulae L-1 to L-14. These are examples of ligands represented by L, but the present invention is not limited thereto.

[Chemical Formula L-1]

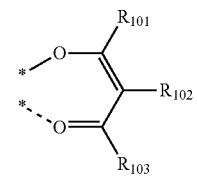

[Chemical Formula L-2]

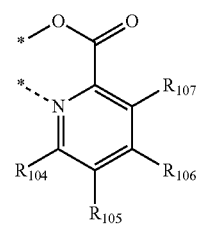

[Chemical Formula L-3]

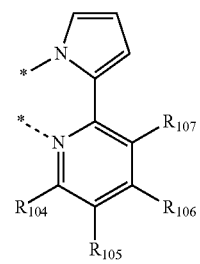

[Chemical Formula L-4]
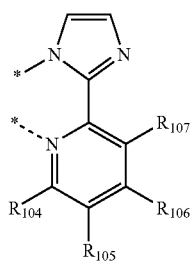
[Chemical Formula L-5]
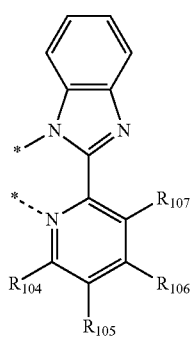
[Chemical Formula L-6]
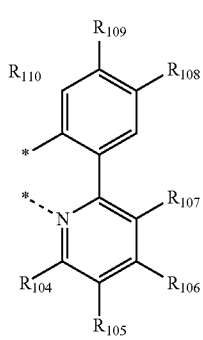
[Chemical Formula L-7]
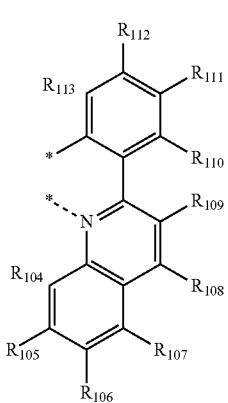
[Chemical Formula L-8]
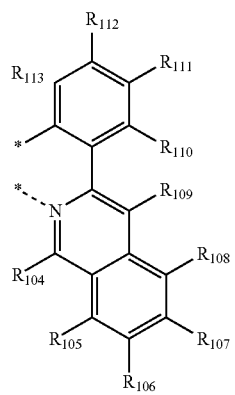
[Chemical Formula L-9]
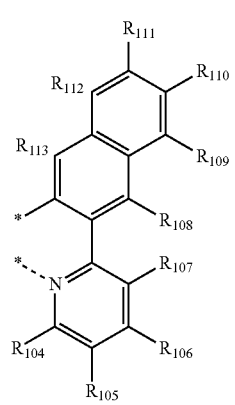
[Chemical Formula L-10]
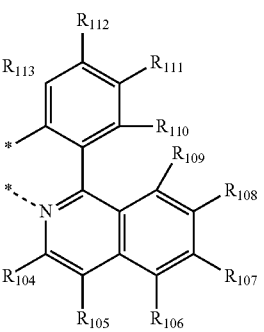
[Chemical Formula L-11]
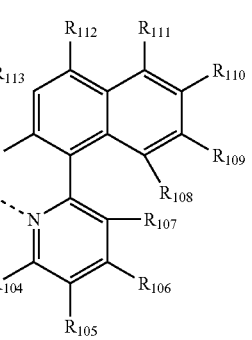

-continued

[Chemical Formula L-12]

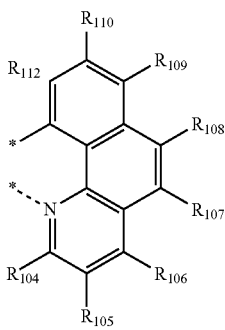

[Chemical Formula L-13]

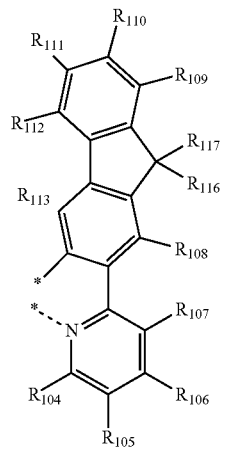

[Chemical Formula L-14]

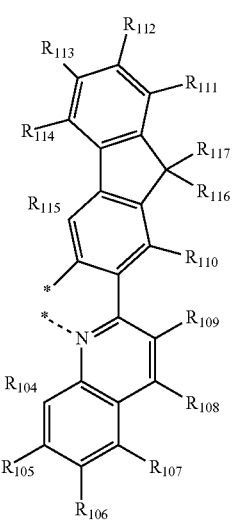

In the above Chemical Formulae L-1 to L-14, the asterisk (*) denotes a position bonding with iridium (Ir), and $R_{101}$ to $R_{103}$ are independently hydrogen, deuterium, a C1 to C30 alkyl group substituted or unsubstituted with a halogen, a C6 to C30 aryl group substituted or unsubstituted with a C1 to C30 alkyl, or a halogen.

$R_{104}$ to $R_{115}$ are independently hydrogen, deuterium, halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C2 to C30 alkenyl group, a substituted or unsubstituted C6 to C30 aryl group, a substituted or unsubstituted C1 to C30 heteroaryl group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group.

$R_{116}$ to $R_{117}$ are independently hydrogen, deuterium, a C1 to C30 alkyl group substituted or unsubstituted with a halogen, a C6 to C30 aryl group substituted or unsubstituted with a C1 to C30 alkyl.

Specific examples of the above Chemical Formula 1 may be one of the following Chemical Formulae M-1 to M-40, Chemical Formulae P-1 to P-26, and Chemical Formulae Q-1 to Q-46. These have a structure where the main ligand is substituted with one phenyl group and one trimethylsilyl group. However, these are specific examples of Chemical Formula 1 which is not limited thereto.

[Chemical Formula M-1]

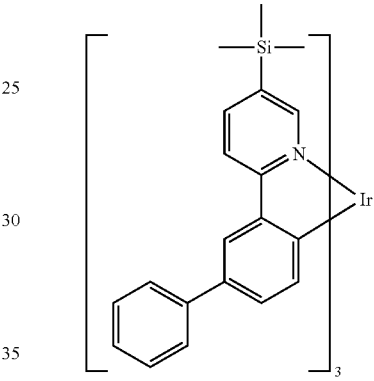

[Chemical Formula M-2]

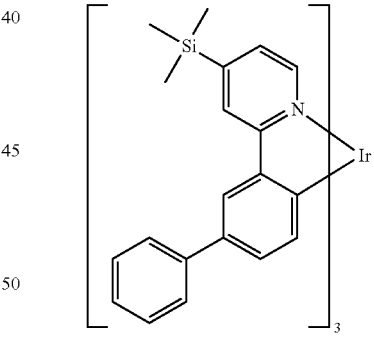

[Chemical Formula M-3]

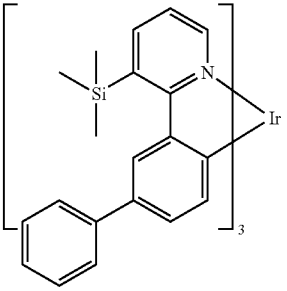

[Chemical Formula M-4]
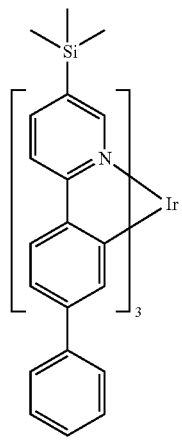
[Chemical Formula M-5]
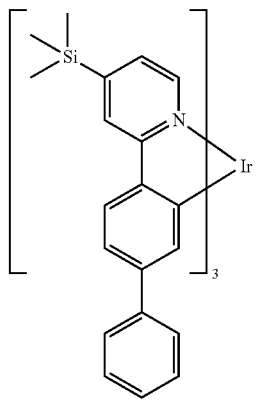
[Chemical Formula M-6]
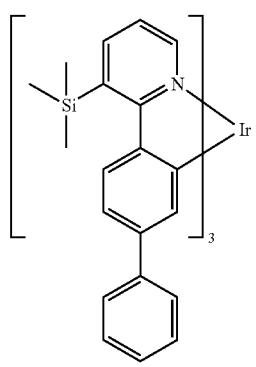
[Chemical Formula M-7]
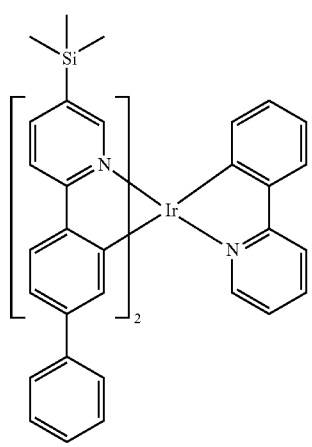
[Chemical Formula M-8]
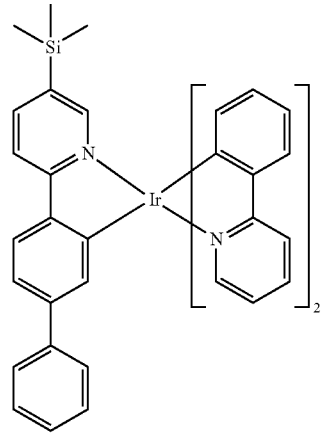
[Chemical Formula M-9]
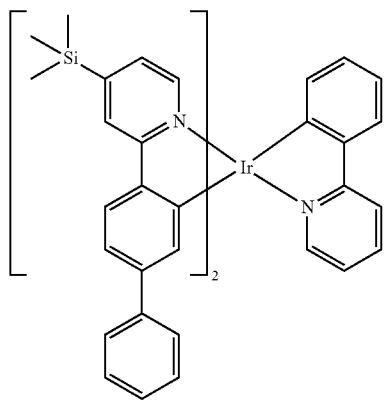
[Chemical Formula M-10]
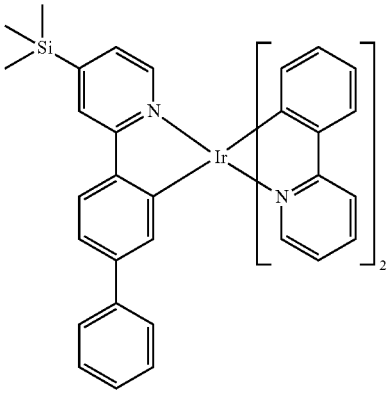
[Chemical Formula M-11]
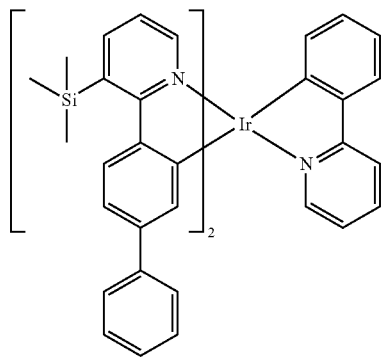

[Chemical Formula M-12]
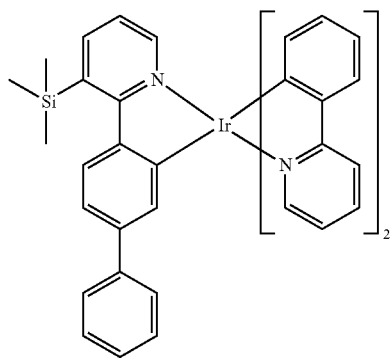
[Chemical Formula M-13]
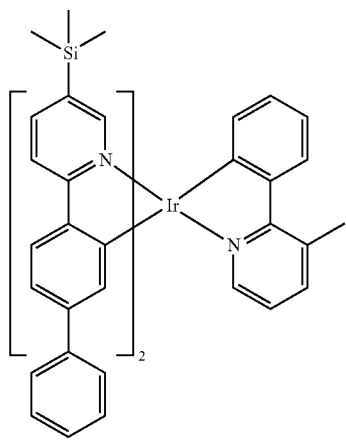
[Chemical Formula M-14]
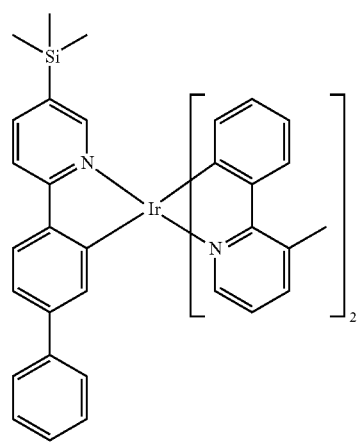
[Chemical Formula M-15]
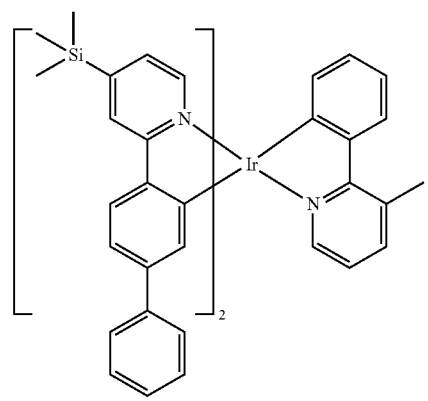
Chemical Formula M-16]
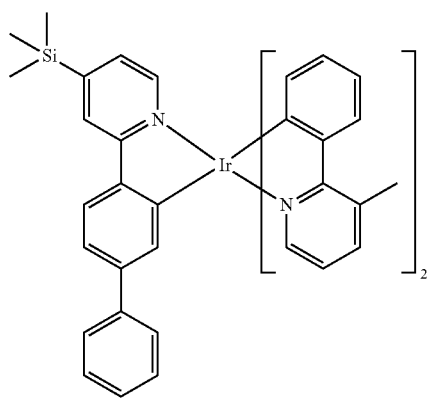
[Chemical Formula M-17]
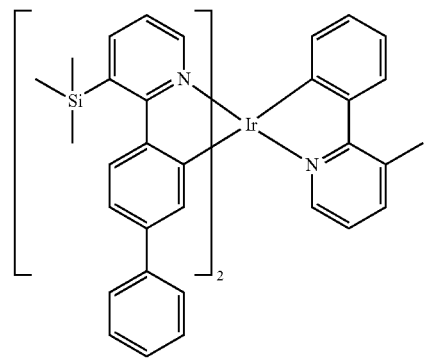
[Chemical Formula M-18]
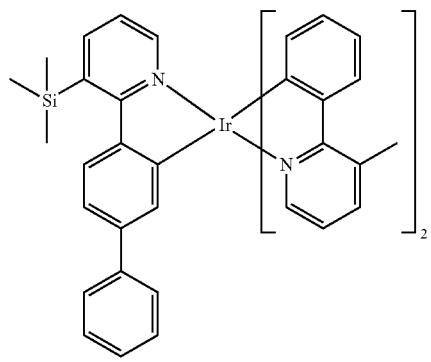

[Chemical Formula M-19]
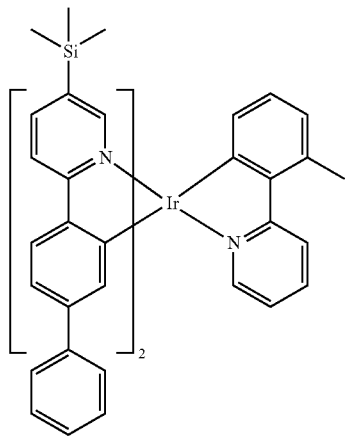
[Chemical Formula M-20]
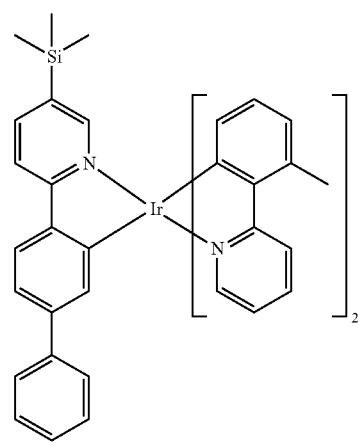
[Chemical Formula M-21]
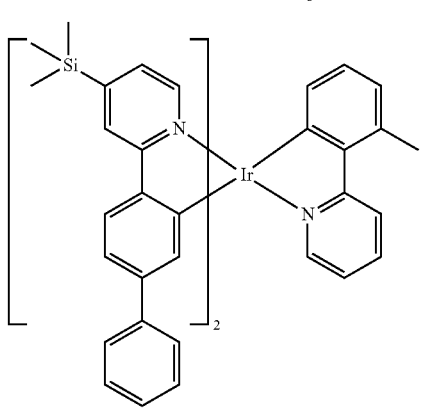
[Chemical Formula M-22]
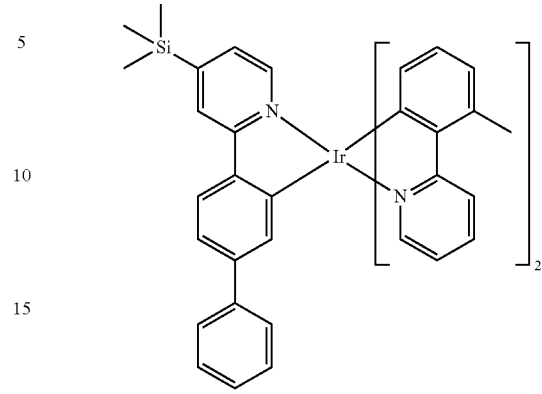
[Chemical Formula M-23]
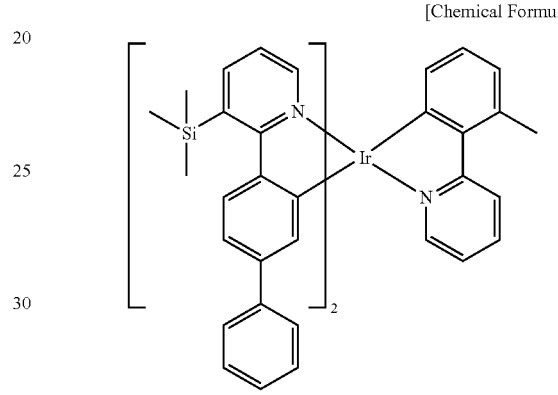
[Chemical Formula M-24]
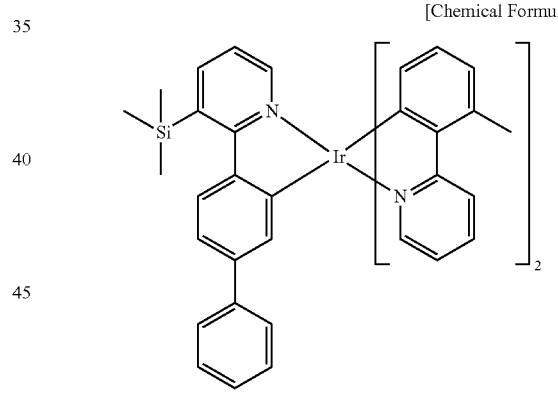
[Chemical Formula M-25]
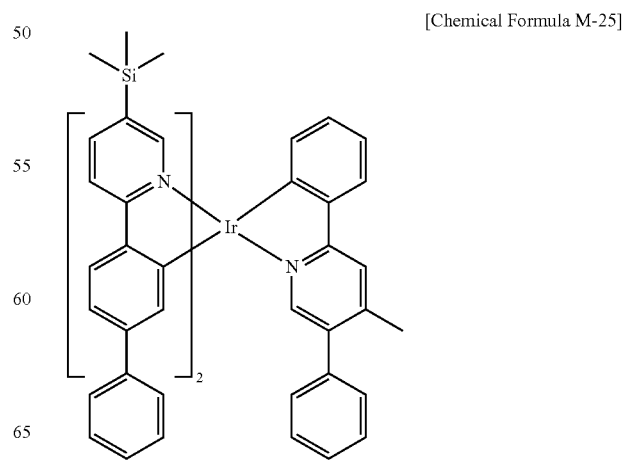

[Chemical Formula M-26]
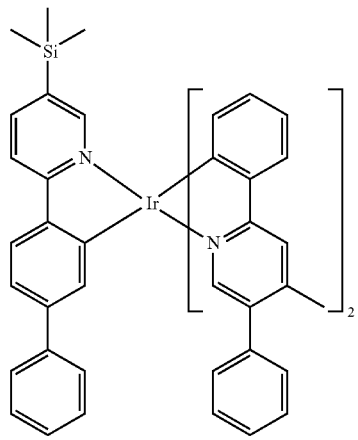
[Chemical Formula M-27]
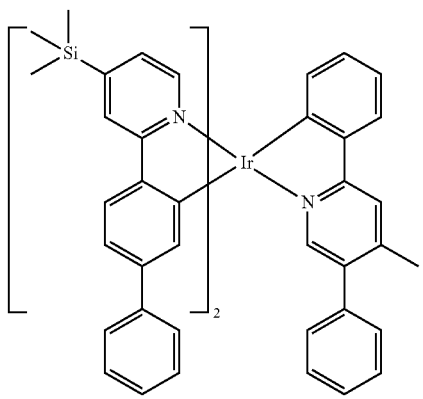
[Chemical Formula M-28]
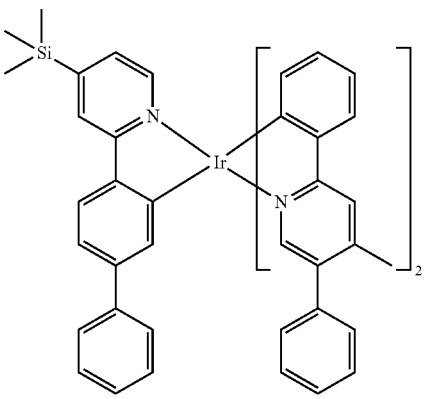
[Chemical Formula M-29]
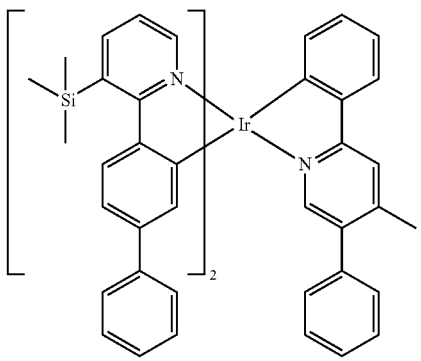
[Chemical Formula M-30]
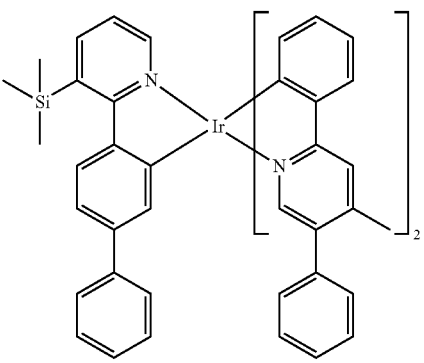
[Chemical Formula M-31]
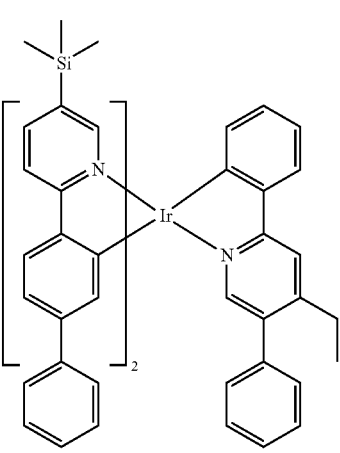

[Chemical Formula M-32]
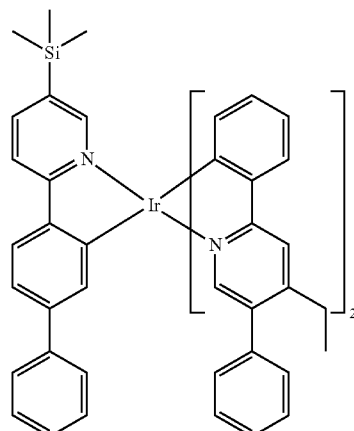
[Chemical Formula M-33]
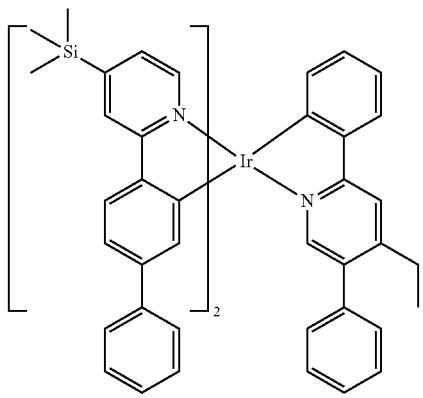
[Chemical Formula M-34]
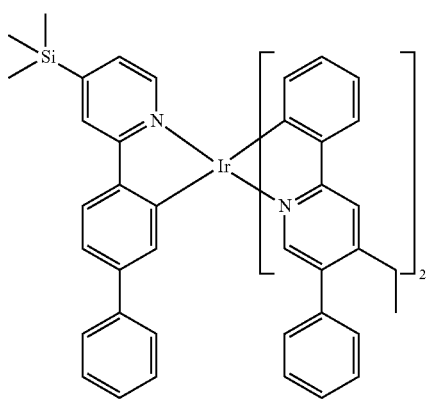
[Chemical Formula M-35]
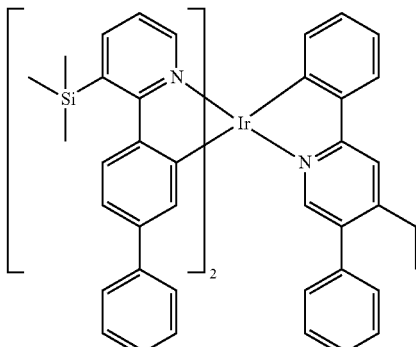
[Chemical Formula M-36]
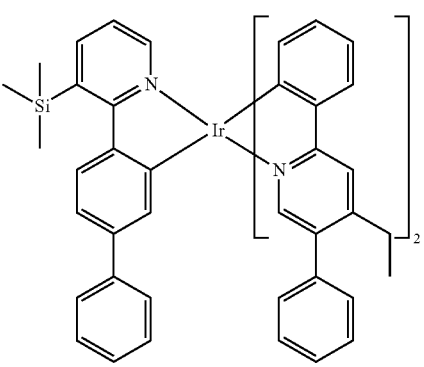
[Chemical Formula M-37]
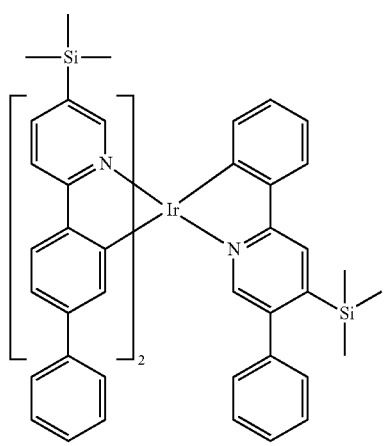

[Chemical Formula M-38]
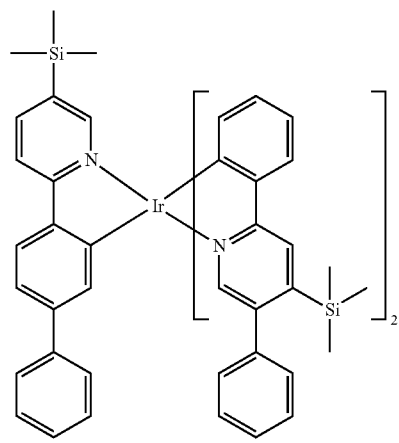
[Chemical Formula M-39]
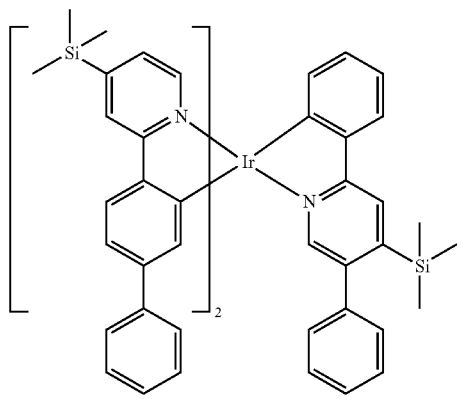
[Chemical Formula M-40]
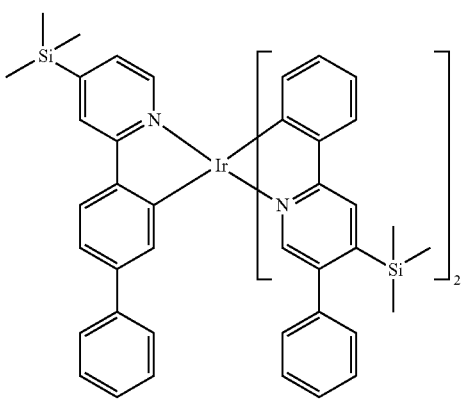
[Chemical Formula P-1]
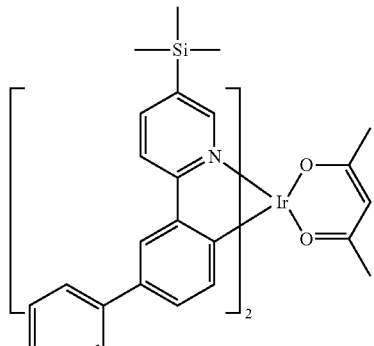
[Chemcial Formula P-2]
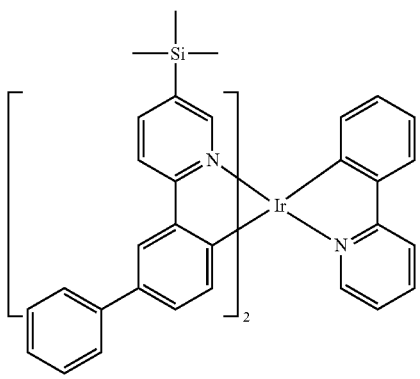
[Chemical Formula P-3]
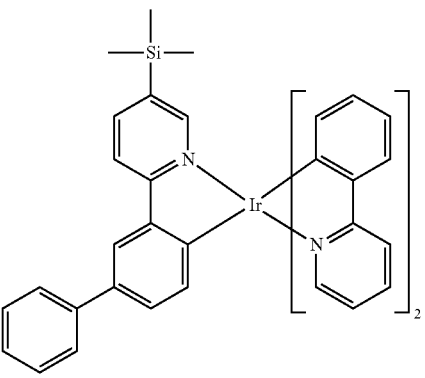
[Chemical Formula P-4]
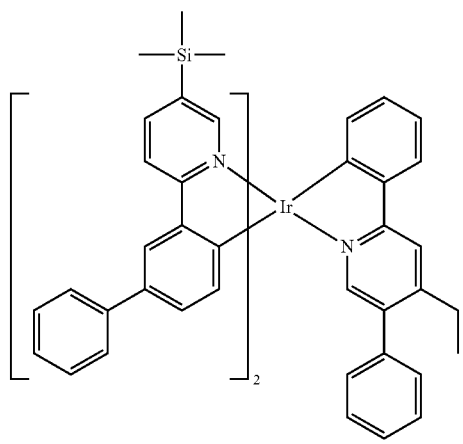

[Chemical Formula P-5]
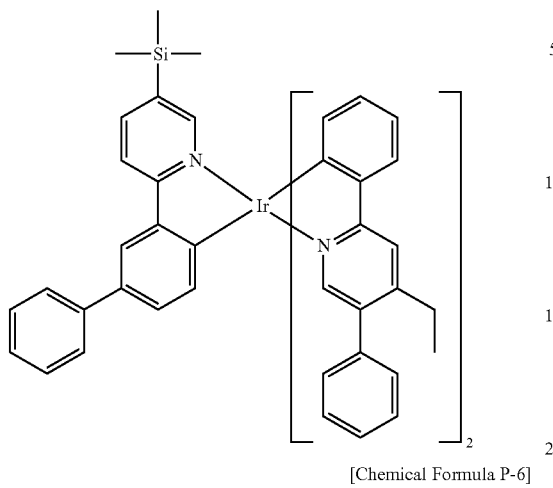
[Chemical Formula P-6]
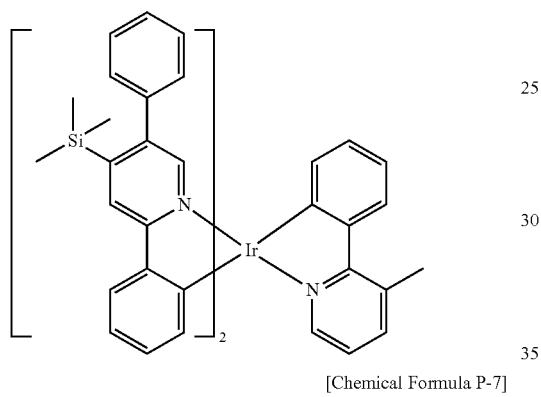
[Chemical Formula P-7]
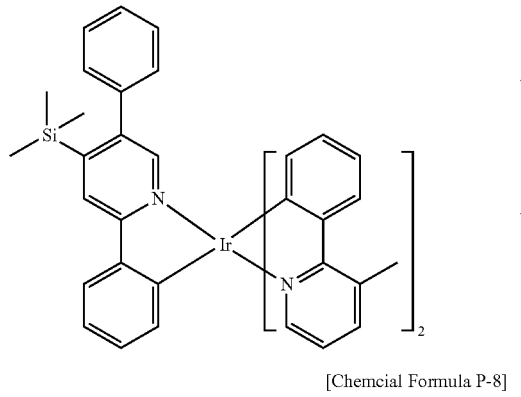
[Chemcial Formula P-8]
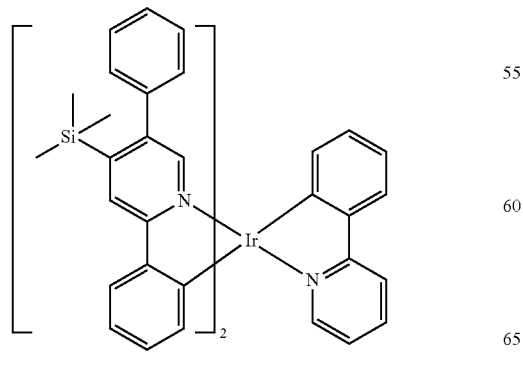
[Chemical Formula P-9]
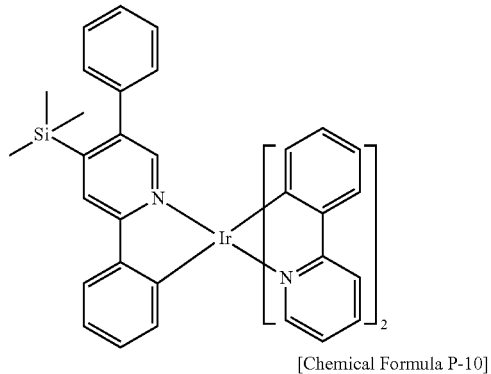
[Chemical Formula P-10]
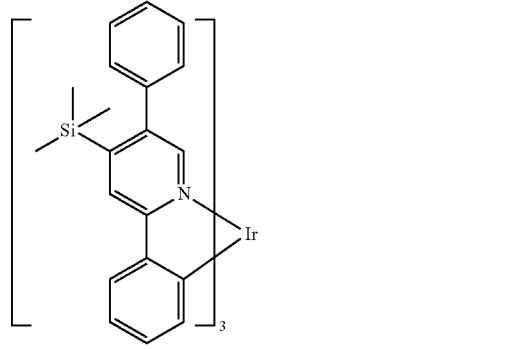
[Chemical Formula P-11]
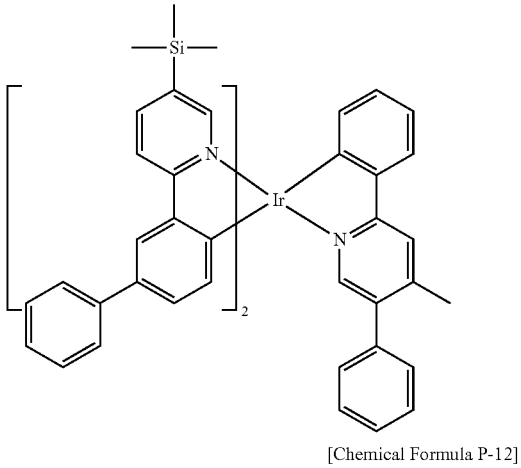
[Chemical Formula P-12]
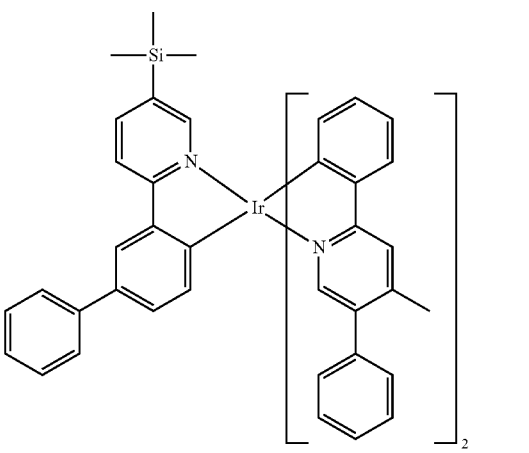

[Chemical Formula P-13]
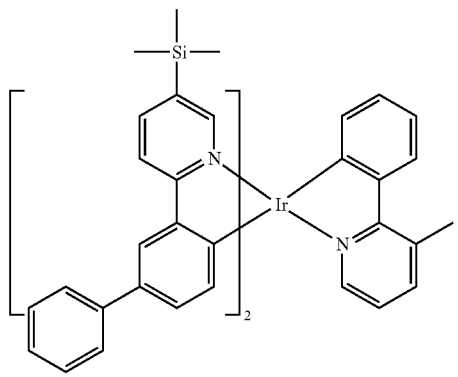
[Chemical Formula P-14]
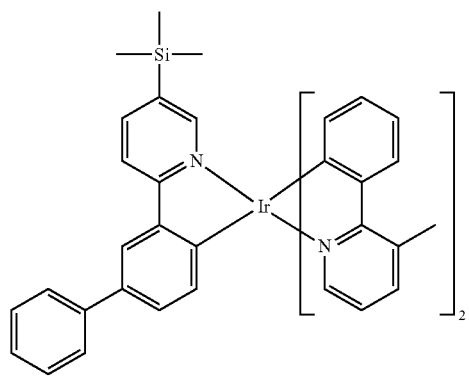
[Chemical Formula P-15]
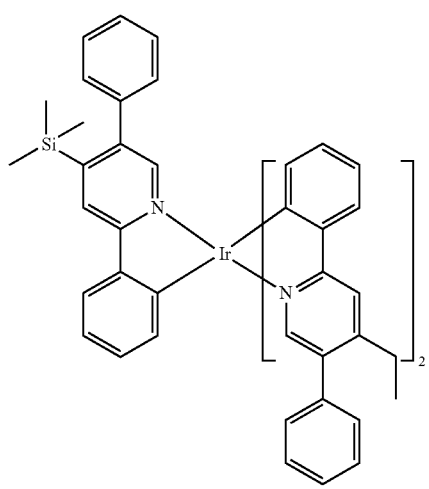
[Chemical Formula P-16]
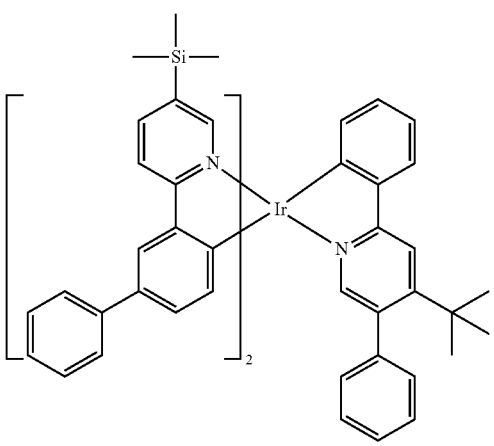
[Chemical Formula P-17]
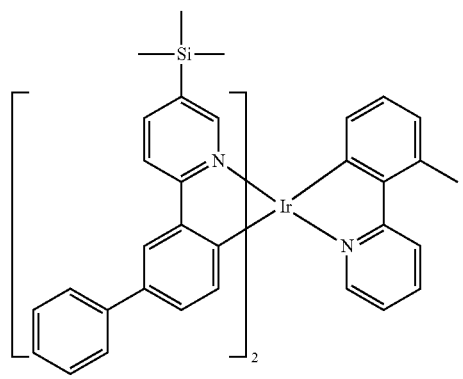
[Chemical Formula P-18]
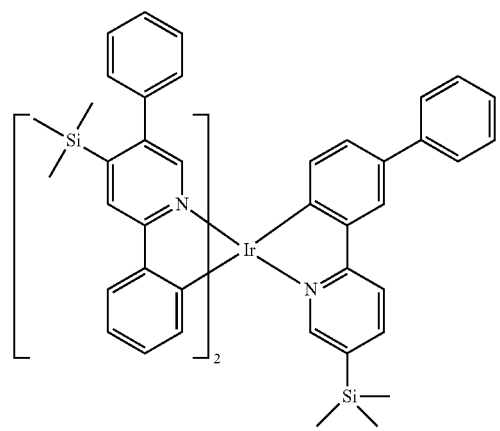

[Chemical Formula P-19]
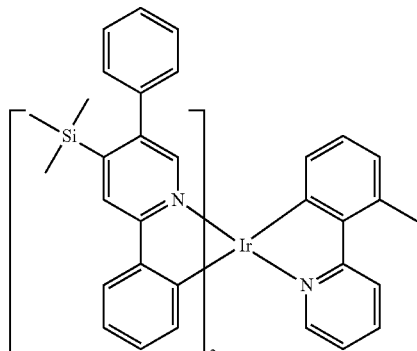
[Chemical Formula P-20]
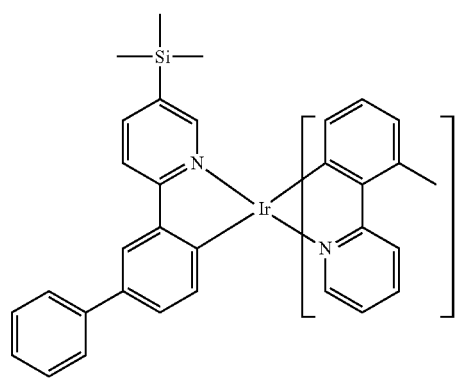
[Chemical Formula P-21]
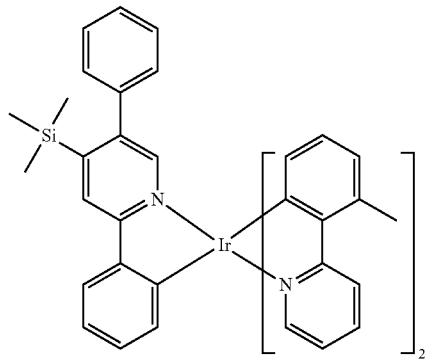
[Chemical Formula P-22]
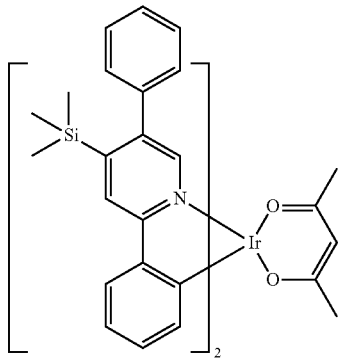
[Chemical Formula P-23]
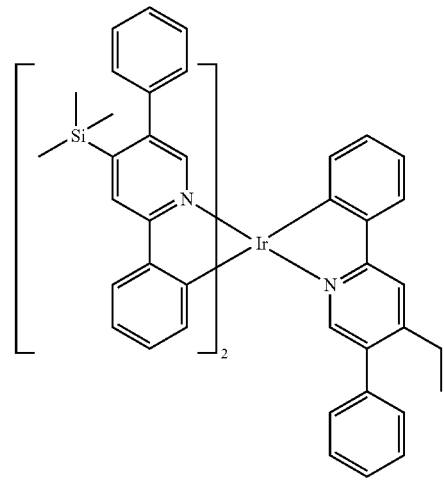
[Chemical Formula P-24]
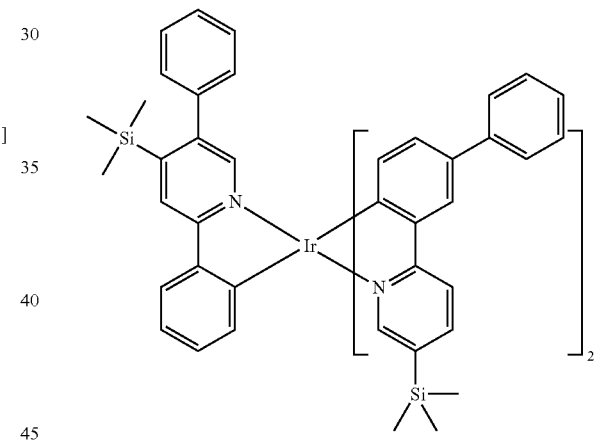
[Chemical Formula P-25]
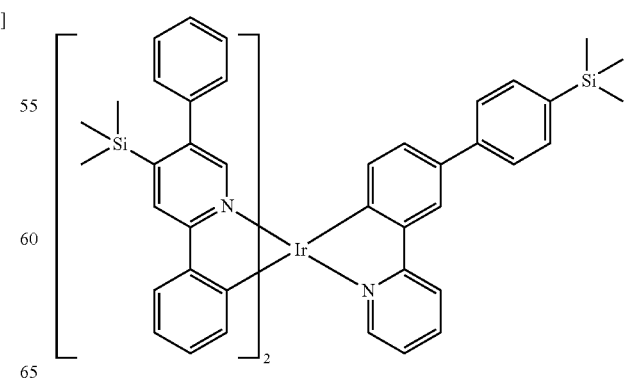

[Chemical Formula P-26]
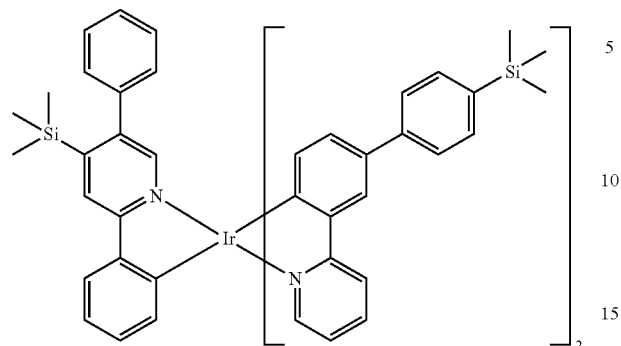
[Chemical Formula Q-1]
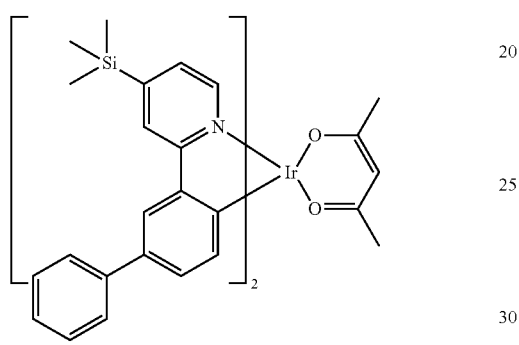
[Chemical Formula Q-2]
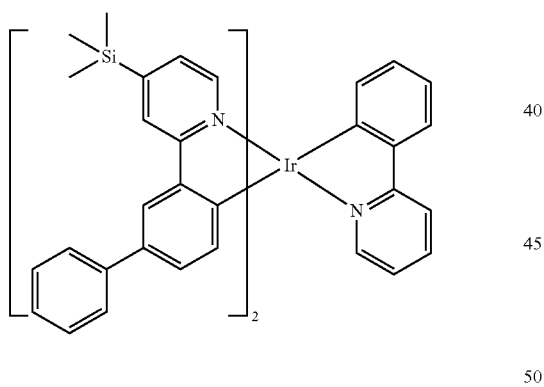
[Chemical Formula Q-3]
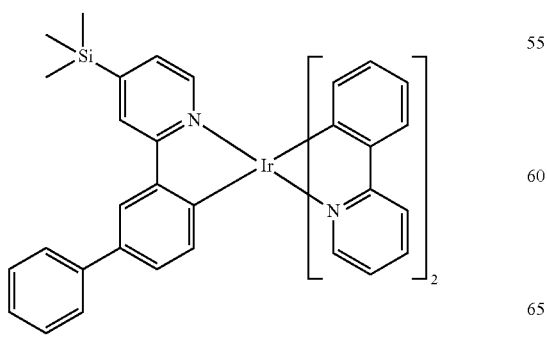
[Chemical Formula Q-4]
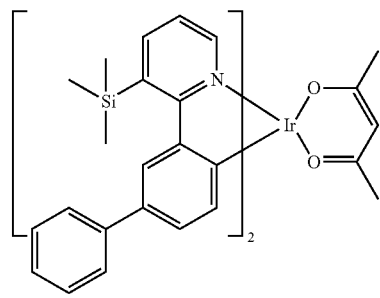
[Chemical Formula Q-5]
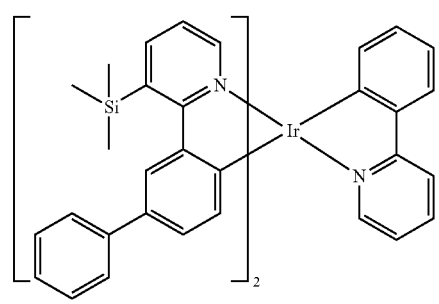
[Chemical Formula Q-6]
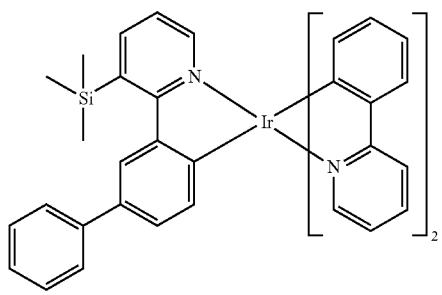
[Chemical Formuula Q-7]
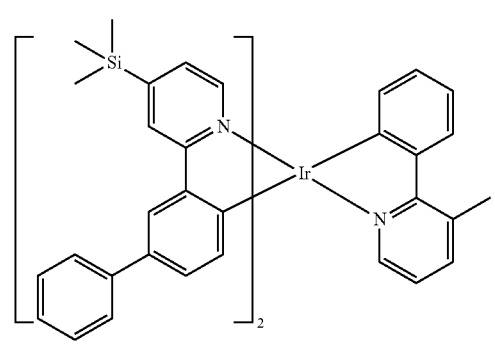

[Chemical Formula Q-8]
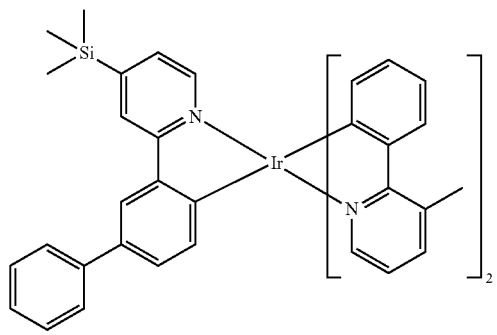
[Chemical Formula Q-12]
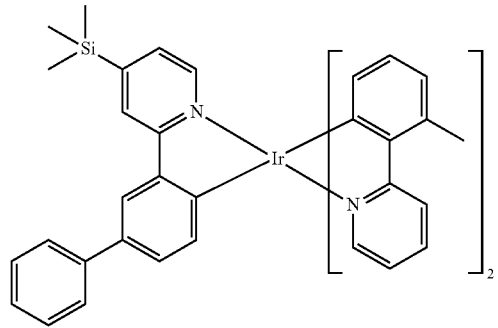
[Chemical Formula Q-9]
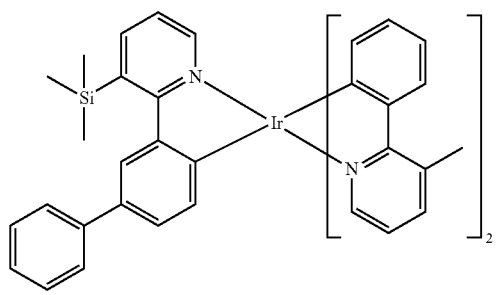
[Chemical Formula Q-13]
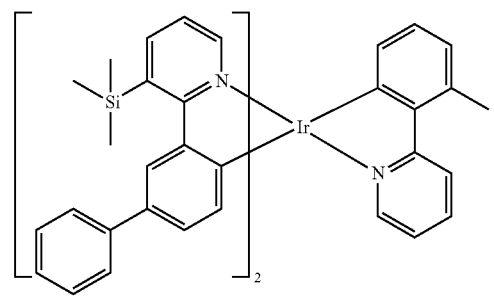
[Chemical Formula Q-10]
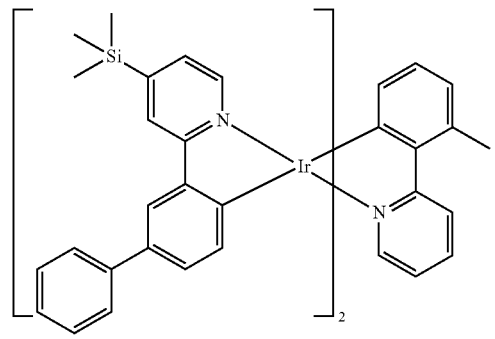
[Chemical Formula Q-14]
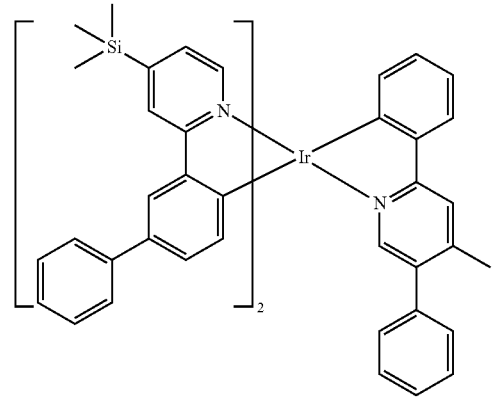
[Chemical Formula Q-11]
[Chemical Formula Q-15]

-continued
[Chemical Formula Q-16]
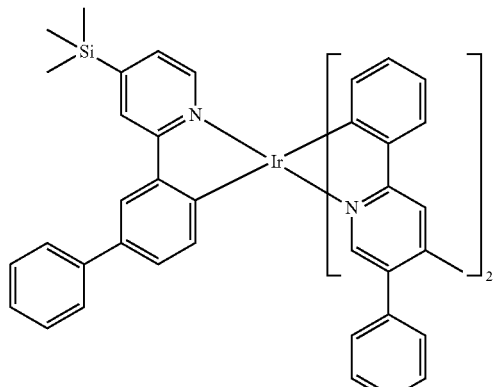
[Chemical Formula Q-17]
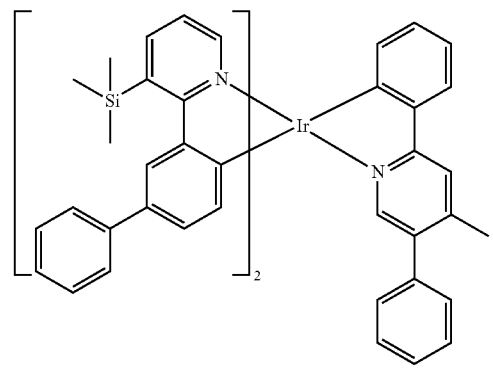
[Chemical Formula Q-18]
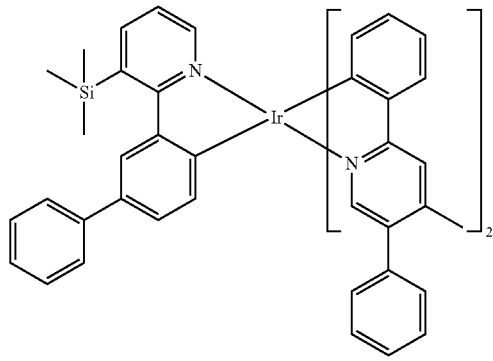
[Chemical Formula Q-19]
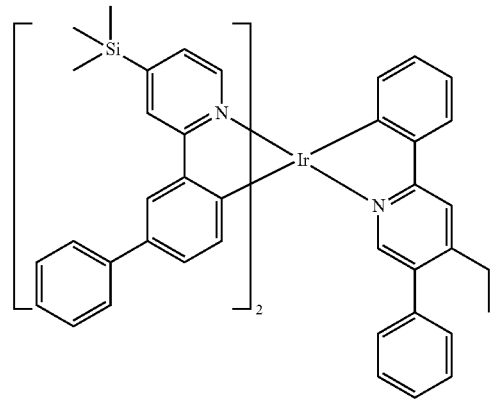
-continued
[Chemical Formula Q-20]
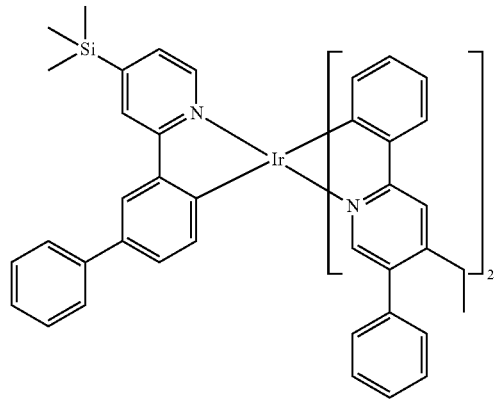
[Chemical Formula Q-21]
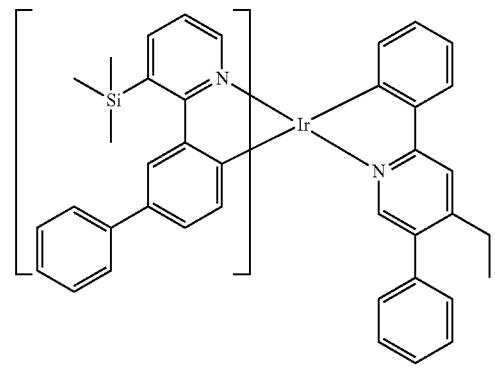
[Chemical Formula Q-22]
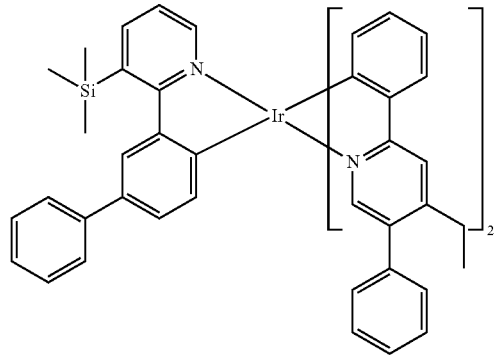
[Chemical Formula Q-23]
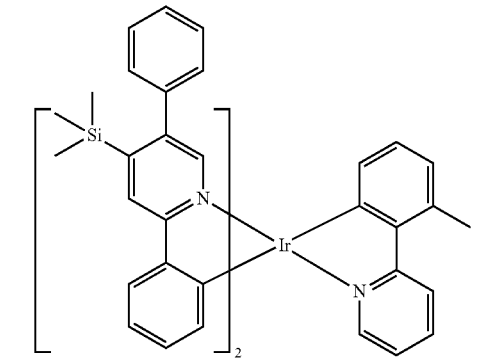

[Chemical Formula Q-24]
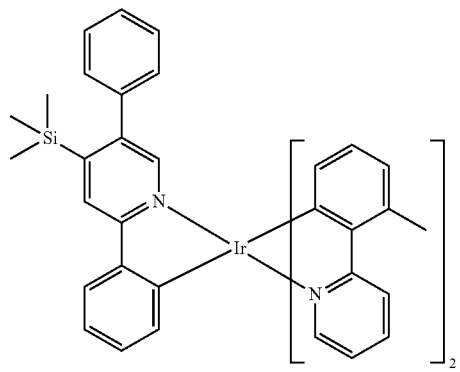
[Chemical Formula Q-25]
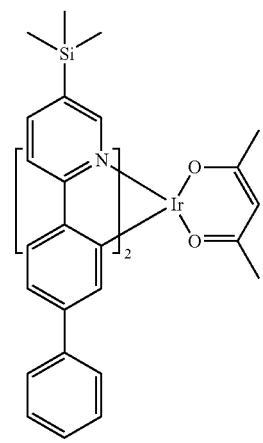
[Chemical Formula Q-26]
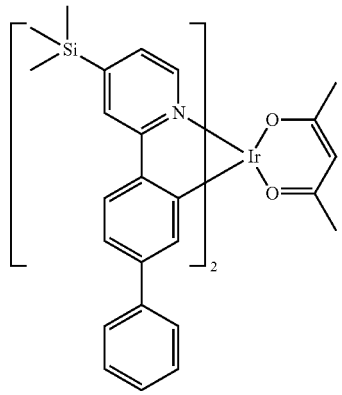
[Chemical Formula Q-27]
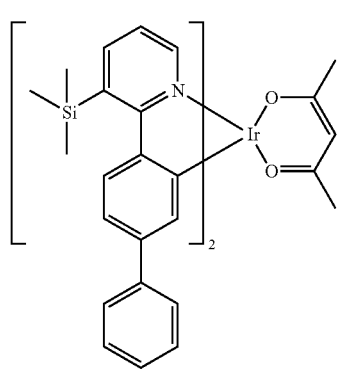
[Chemical Formula Q-28]
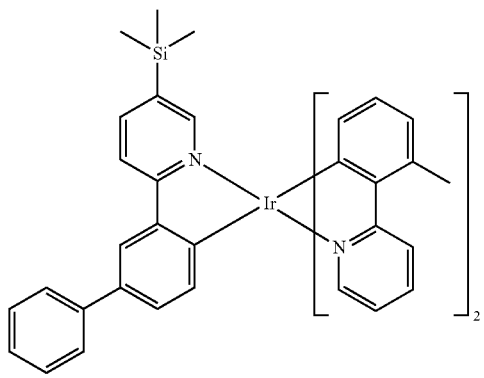
[Chemical Formula Q-29]
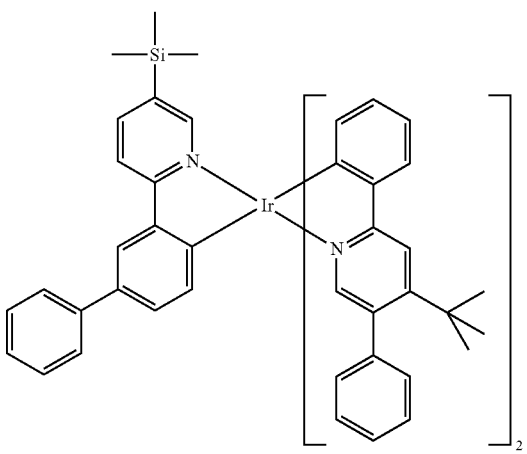
[Chemical Formula Q-30]
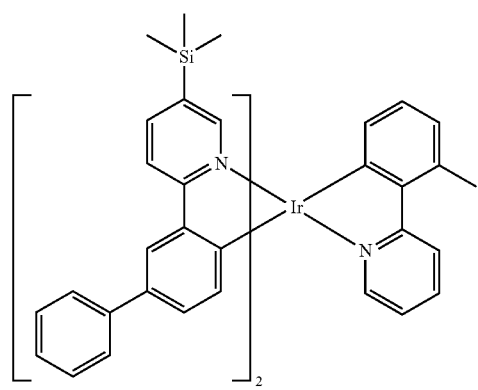

[Chemical Formula Q-31]
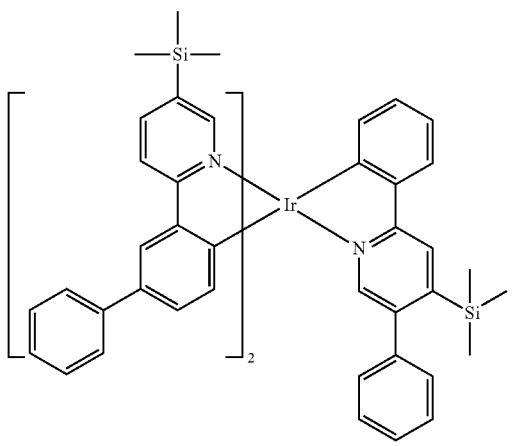
[Chemical Formula Q-32]
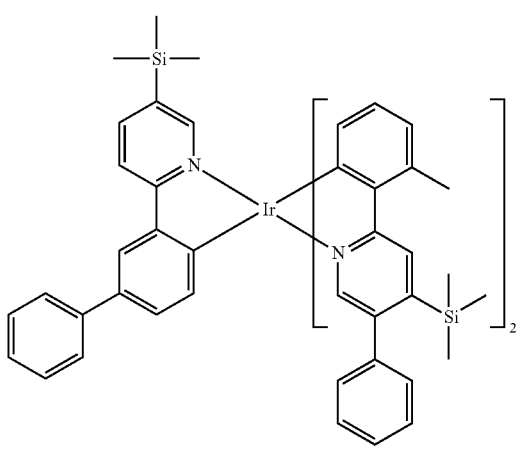
[Chemical Formula Q-33]
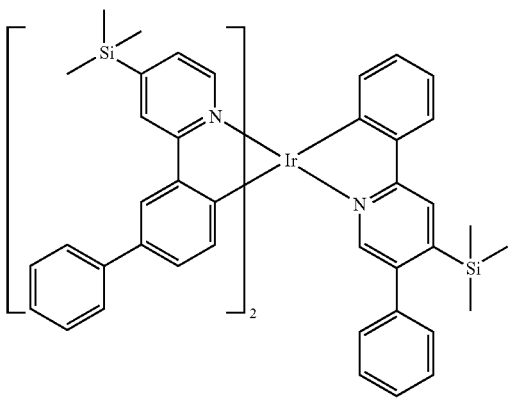
[Chemical Formula Q-34]
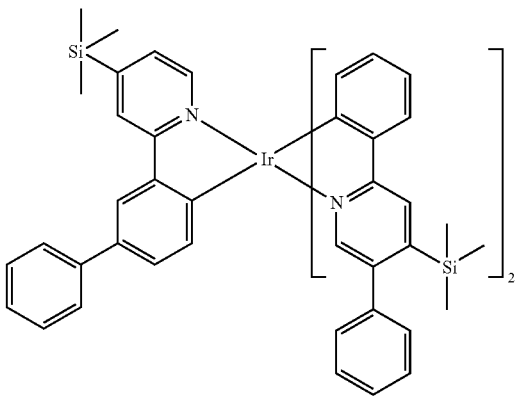
[Chemical Formula Q-35]
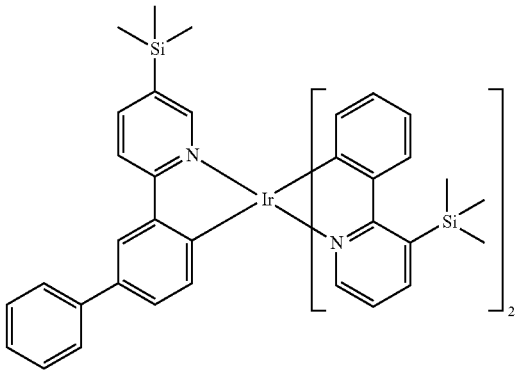
[Chemical Formula Q-36]
[Chemical Formula Q-37]
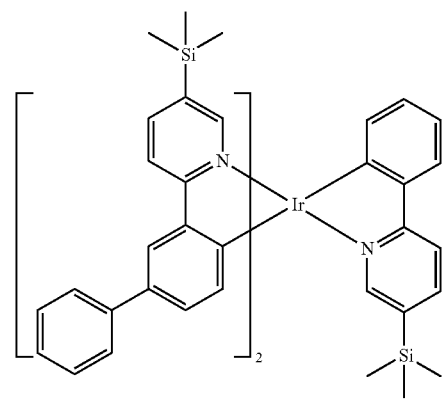

[Chemical Formula Q-38]
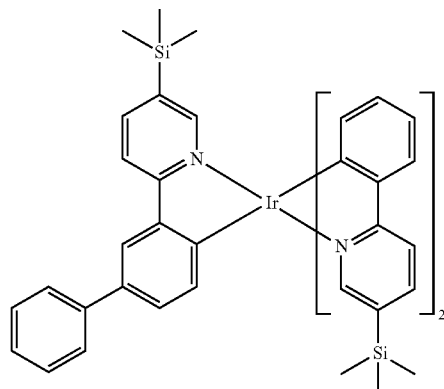
[Chemical Formula Q-39]
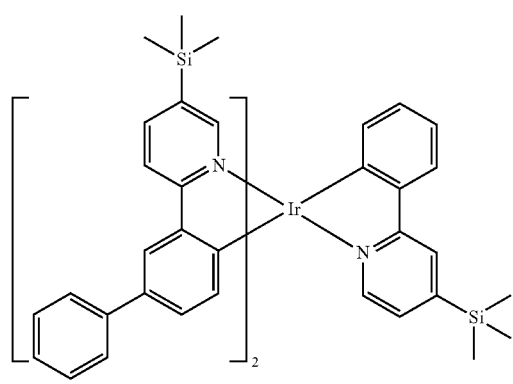
[Chemical Formula Q-40]
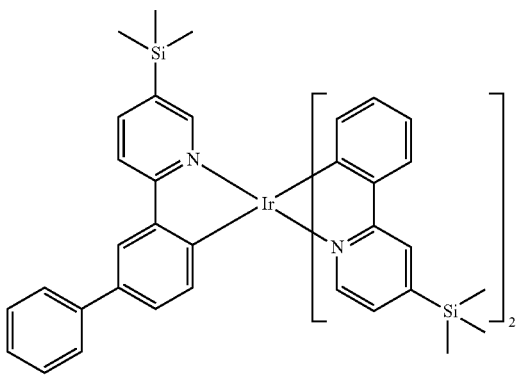
[Chemical Formula Q-41]
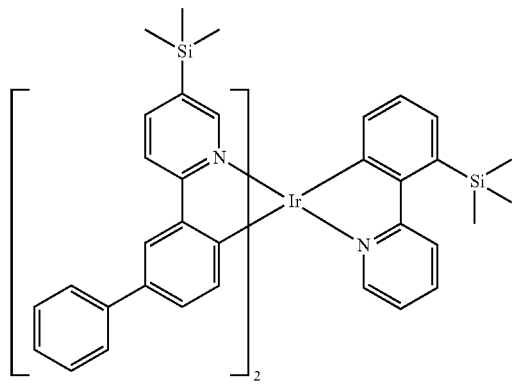
[Chemical Formula Q-42]
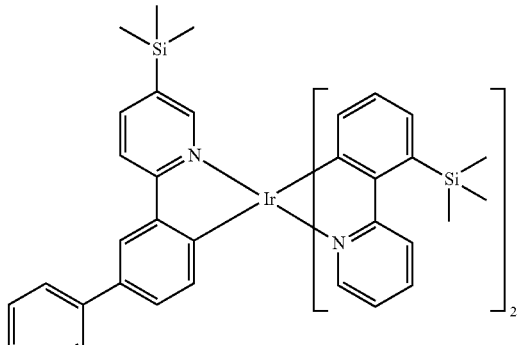
[Chemical Formula Q-43]
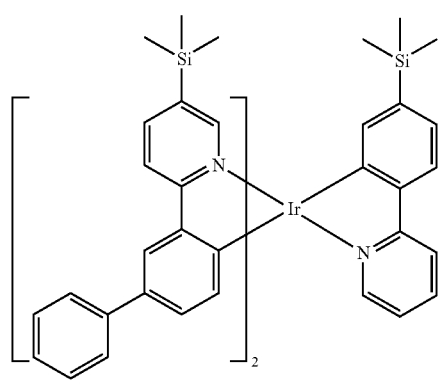
[Chemical Formula Q-44]
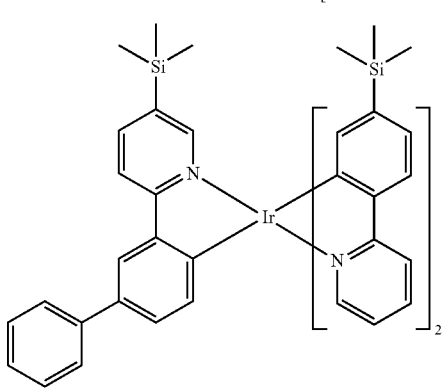
[Chemical Formula Q-45]
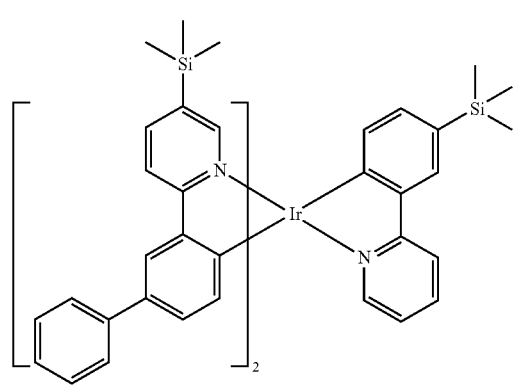

[Chemical Formula Q-46]

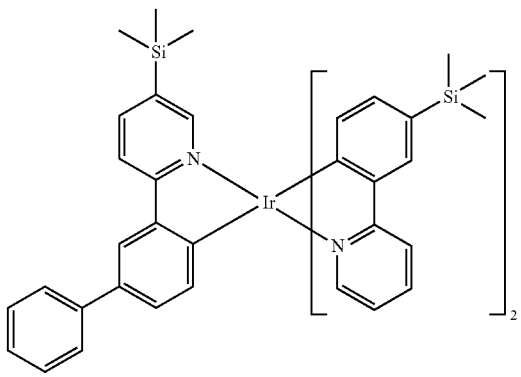

In another embodiment of the present invention, an organic optoelectric device includes an anode, a cathode, and at least one or more organic thin layer between the anode and the cathode, and at least one of the organic thin layers may include the compound for an organic optoelectric device.

The compound for an organic optoelectric device is used in an organic thin layer and thus improves life-span characteristics, efficiency characteristics, electrochemical stability, and thermal stability of an organic optoelectric device, and lowers a driving voltage.

The organic thin layer may be specifically an emission layer.

The organic optoelectric device may be an organic light emitting diode, an organic photoelectric device, an organic solar cell, an organic transistor, an organic photo-conductor drum, or an organic memory device.

More specifically, the organic optoelectric device may be an organic light emitting diode. FIGS. 1 to 5 are cross-sectional views showing organic light emitting diodes including the compound for an organic optoelectric device according to one embodiment of the present invention.

Figure 2:
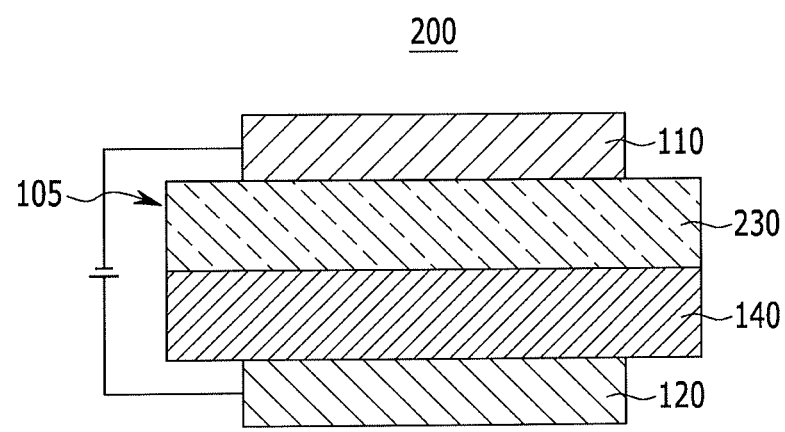

Referring to FIGS. 1 and 2, organic light emitting diodes 100 and 200 according to one embodiment of the present invention includes an anode 120, a cathode 110, and at least one organic thin layer 105 between the anode and the cathode.

The anode 120 includes an anode material having a large work function to help hole injection into an organic thin layer. Specific examples of the anode material includes: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a bonded metal and oxide such as ZnO:Al or $SnO_2$:Sb; or a conductive polymer such as poly(3-methylthiophene), poly[3,4-(ethylene-1,2-dioxy) thiophene] (PEDT), polypyrrole, and polyaniline, but is not limited thereto. It is preferable to include a transparent electrode including indium tin oxide (ITO) as an anode.

The cathode 110 includes a cathode material having a small work function to help electron injection into an organic thin layer. The cathode material includes: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca, but is not limited thereto. It is preferable to include a metal electrode including aluminum as a cathode.

Referring to FIG. 1, the organic light emitting diode 100 includes an organic thin layer 105 including only an emission layer 130.

Referring to FIG. 2, a double-layered organic light emitting diode 200 includes an organic thin layer 105 including an emission layer 230 including an electron transport layer (ETL), and a hole transport layer (HTL) 140. As shown in FIG. 2, the organic thin layer 105 includes a double layer of the emission layer 230 and hole transport layer (HTL) 140. The emission layer 130 also functions as an electron transport layer (ETL), and the hole transport layer (HTL) 140 layer has an excellent binding property with a transparent electrode such as ITO or an excellent hole transport capability. In one embodiment of the present invention, in FIG. 1 or 2, an organic light emitting diode that further includes an electron transport layer (ETL), an electron injection layer (EIL), a hole injection layer, and the like as an organic thin layer 105 may be provided.

In FIG. 1 or FIG. 2, the emission layers 130 and 230, the hole transport layer (HTL) 140 or even though not drawn in the drawings, one selected from the group consisting of the electron transport layer (ETL), the electron injection layer (EIL), the hole injection layer (HIL) and a combination thereof which constitute the organic thin layer 105 may include the compound for an organic optoelectric device.

Particularly the compound for an organic optoelectric device may be used in the emission layers 130 and 230, and may be used as a green phosphorescent dopant material in the emission layers.

The organic light emitting diode may be manufactured by: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

In another embodiment of the present invention, a display device including the organic optoelectric device is provided.

Hereinafter, the embodiments are illustrated in more detail with reference to examples. These examples, however, should not in any sense be interpreted as limiting the scope of the present invention.

(Preparation of Compound for Organic Optoelectronic Device)

PREPARATION EXAMPLE 1

Preparation of Compound M-1

[Reaction Scheme 1]

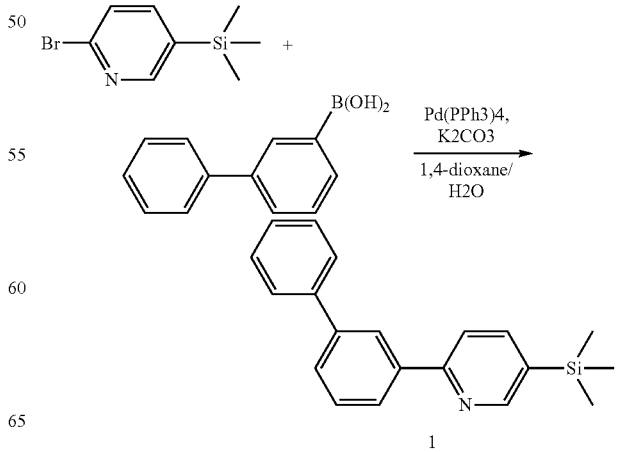

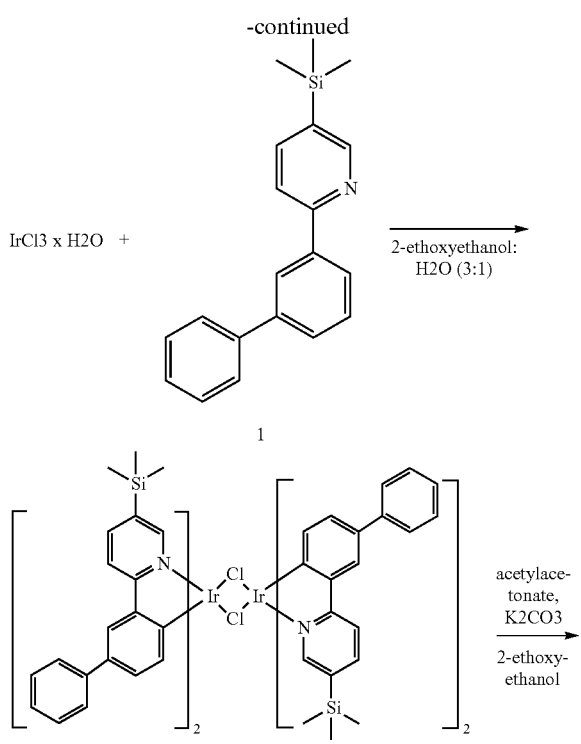

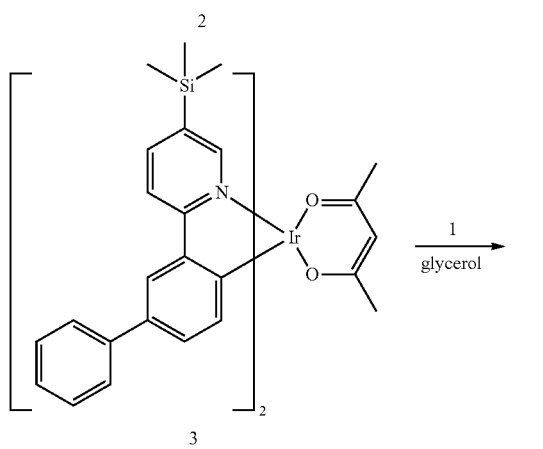

Preparation of Compound 1

87 g (377.97 mmol) of 5-trimethylsilyl-2-bromopyridine (Organic Electrinics 10 (2009) p. 1066-1073), 89.82 g (453.56 mmol) of 3-biphenylboronic acid, 630 mL of 1,4-dioxane, and 378 mL of a 2 M-potassium carbonate aqueous solution were mixed in a 2 L round-bottomed flask equipped with an agitator having a nitrogen atmosphere, 13.1 g (11.34 mmol) of tetrakistriphenyl phosphine palladium (0) was added thereto, and the mixture was heated and refluxed under a nitrogen stream for 12 hours. When the reaction was terminated, an organic layer was separated, and a solvent was all removed therefrom. Then, column chromatography was performed, obtaining 53.34 g of a compound 1 (a yield: 47%).

Preparation of Compound 2

22.36 g (74 mmol) of the compound 1, 8.8 g (29 mmol) of iridium chloride, 123 mL of 2-ethoxyethanol, and 41 mL of distilled water were put in a 500 mL round-bottomed flask and then, heated and refluxed for 24 hours. When the reaction was terminated, the resultant was cooled down to room temperature, and a solid produced during the reaction was filtered and washed with water and methanol. The solid was dried in a vacuum oven, obtaining 15.8 g of a compound 2 (a yield: 64%).

Preparation of Compound 3

23 g (13.95 mmol) of the compound 2, 3.072 g (30.68 mmol) of 2,4-pentanedione, and 14.78 g (139.47 mmol) of sodium carbonate were dissolved in 140 mL of 2-ethoxy-ethanol in a 500 mL round-bottomed flask, and the solution was heated and refluxed for 5 hours. When the reaction was terminated, the resultant was cooled down to room temperature, and a solid produced therein was filtered. Then, 13 g of a compound 3 (a yield: 52%) was obtained by performing column chromatography.

Preparation of Compound M-1

13.584 g (15.16 mmol) of the compound 3 and 13.8 g (45.47 mmol) of the compound 1 were dissolved in 150 mL of glycerol in a 250 mL round-bottomed flask, and the solution was heated and refluxed at 220° C. for 12 hours. The reaction was terminated by pouring water to the reactant, and a solid produced therein was filtered. Then, a solid produced therein was washed with water and methanol, dissolved in dichloromethane, separated through column chromatography, and then, recrystallized, obtaining 9 g of a compound M-1 (a yield: 27%).

calcd. $C_{60}H_{60}IrN_3Si_3$: C, 65.54; H, 5.50; Ir, 17.48; N, 3.82; Si, 7.66. found: C, 65.62; H, 5.53; N, 3.91.

PREPARATION EXAMPLE 2

Preparation of Compound P-2

[Reaction Scheme 2]

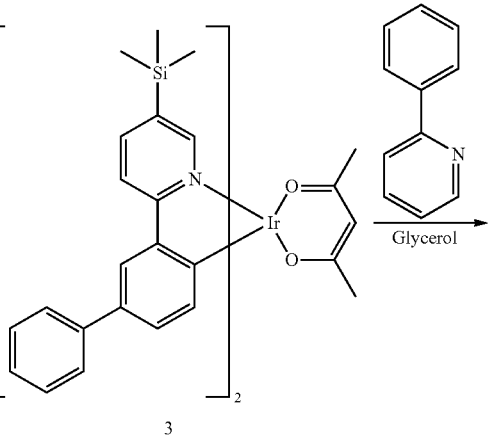

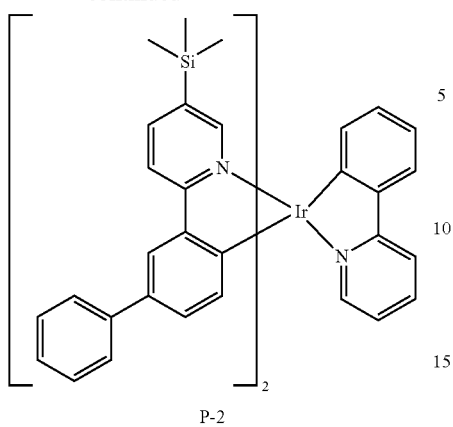

P-2

Preparation of Compound P-2

30.0 g (33.48 mmol) of the compound 3 according to Preparation Example 1 and 15.58 g (100.44 mmol) of 2-phenylpyridine were dissolved in 300 mL of glycerol in a 250 mL round-bottomed flask, and the solution was heated and refluxed at 220° C. for 12 hours. The reaction was terminated by pouring the reactant to water, and a solid produced therein was filtered. The solid was washed with water and methanol, dissolved in dichloromethane, separated through column chromatography, and recrystallized, obtaining 9.54 g of a compound P-2 (a yield: 30%).

calcd. $C_{51}H_{48}IrN_3Si_2$: C, 64.39; H, 5.09; Ir, 20.20; N, 4.42; Si, 5.90. found: C, 64.28; H, 5.04; N, 4.44.

PREPARATION EXAMPLE 3

Preparation of Compound P-3

[Reaction Scheme 3]

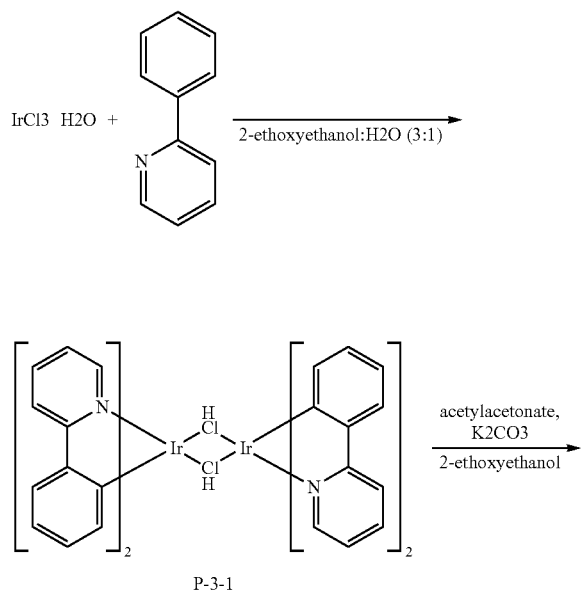

P-3-1

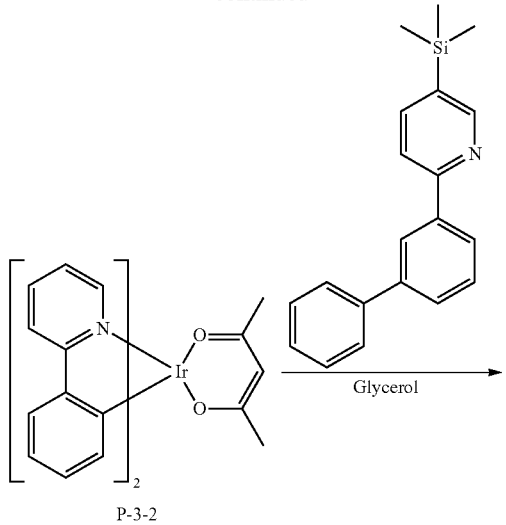

P-3-2

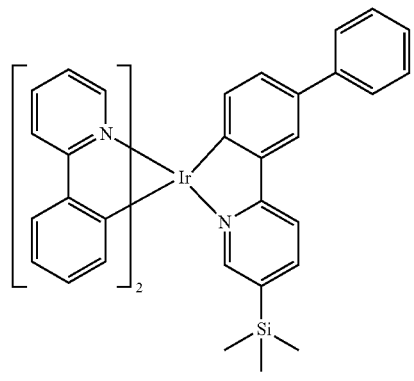

P-3

Preparation of Compound P-3-1

79.32 g (511.10 mmol) of 2-phenylpyridine, 61.04 g (204.44 mmol) of iridium chloride, 852 mL of 2-ethoxyethanol, and 283 mL of distilled water were put in a 100 mL round-bottomed flask and then, heated and refluxed for 24 hours. When the reaction was terminated, the resultant was cooled down to room temperature, and a solid produced during the reaction was filtered and then, washed with water and methanol. The solid was dried in a vacuum oven, obtaining 80 g of a compound P-3-1 (a yield: 73%).

Preparation of Compound P-3-2

80 g (74.62 mmol) of the compound P-3-1, 16.42 g (164.04 mmol) of 2,4-pentanedione, and 79.06 g (746.20 mmol) of sodium carbonate were dissolved in 800 mL of 2-ethoxyethanol in a 2000 mL round-bottomed flask and then, heated and refluxed for 5 hours. When the reaction was terminated, the resultant was cooled down to room temperature, and a solid produced therein was filtered. Then, 25.04 g of a compound P-3-2 (a yield: 56%) was obtained through column chromatography.

Preparation of Compound P-3

25.0 g (41.68 mmol) of the compound P-3-2 and 37.94 g (125.04 mmol) of the compound 1 according to Preparation Example 1 were dissolved in 450 mL of glycerol in a 250 mL round-bottomed flask, and the solution was heated and refluxed at 220° C. for 12 hours. The reaction was terminated by pouring the reactant to water, and a solid produced therein was filtered. The solid was washed with water and methanol, dissolved in dichloromethane, separated through column chromatography, and recrystallized, obtaining 10.71 g of a compound P-3 (a yield: 32%).

calcd. $C_{42}H_{36}IrN_3Si$: C, 62.82; H, 4.52; Ir, 23.94; N, 5.23; Si, 3.50. found: C, 62.79; H, 4.50; N, 5.20.

PREPARATION EXAMPLE 4

Preparation of P-11

[Reaction Scheme 4]

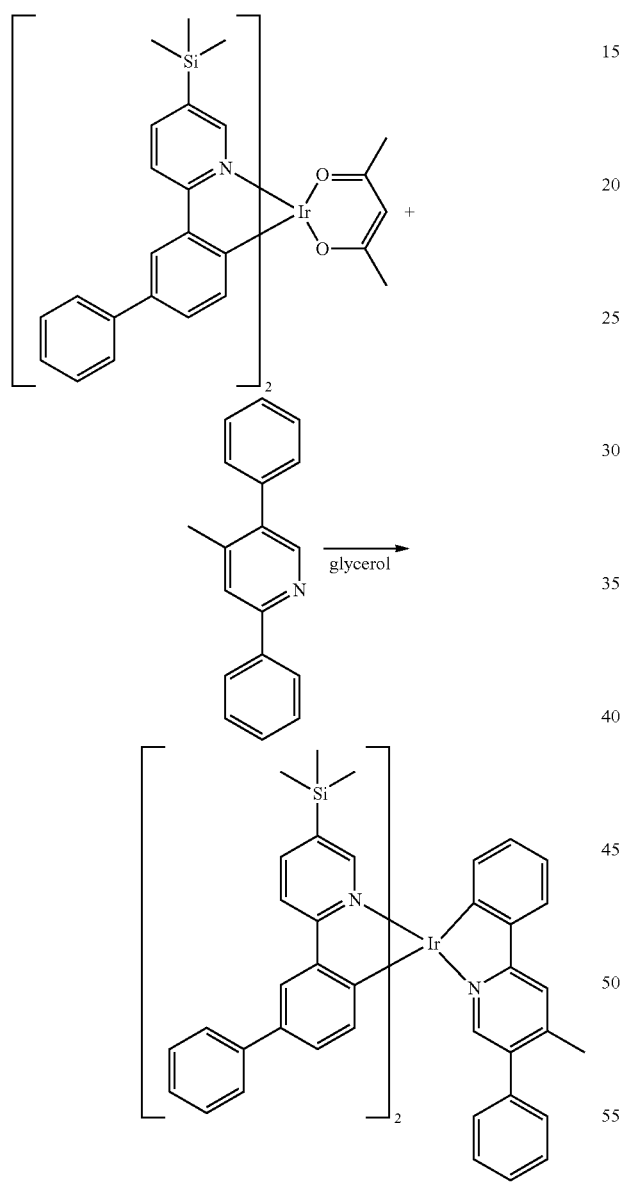

PREPARATION EXAMPLE 5

Preparation of Compound P-12

[Reaction Scheme 5]

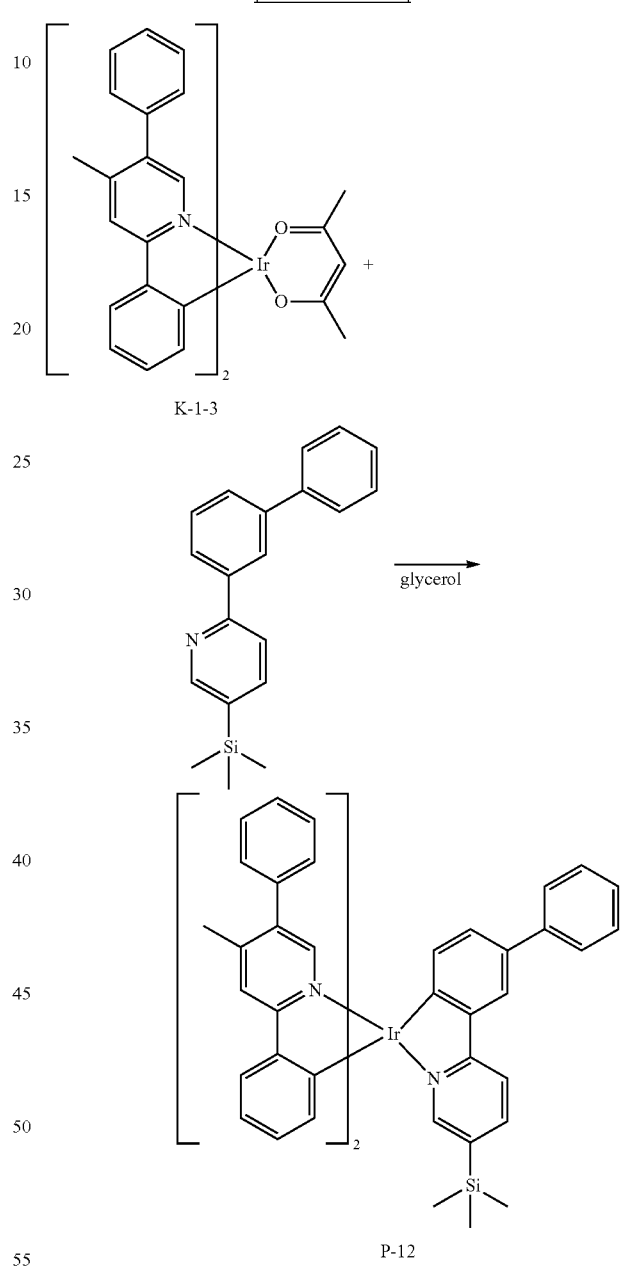

5 g of a compound P-11 (a yield: 31%) was synthesized by using 13.001 g (14.51 mmol) of the compound 3 according to Preparation Example 1 and 10.679 g (43.53 mmol) of a compound K-1-1 (KR2011-0065496A, page 87) in a 250 mL round-bottomed flask according to the same method as a method of preparing the compound M-1.

calcd. $C_{58}H_{54}IrN_3Si_2$: C, 66.89; H, 5.23; Ir, 18.46; N, 4.03; Si, 5.39. found: C, 66.92; H, 5.24; N, 4.09.

4.8 g of a compound P-12 (a yield: 30%) was synthesized by using 16.2 g (37.67 mmol) of the compound K-1-3 according to Preparation Example 1 and 34.3 g (113.02 mmol) of the compound 1 in a 250 mL round-bottomed flask according to the same method as a method of preparing the compound M-1.

calcd. $C_{56}H_{48}IrN_3Si$: C, 68.40; H, 4.92; Ir, 19.55; N, 4.27; Si, 2.86. found: C, 68.50; H, 4.90; N, 4.29.

PREPARATION EXAMPLE 6

Preparation of Compound P-10

[Reaction Scheme 6]

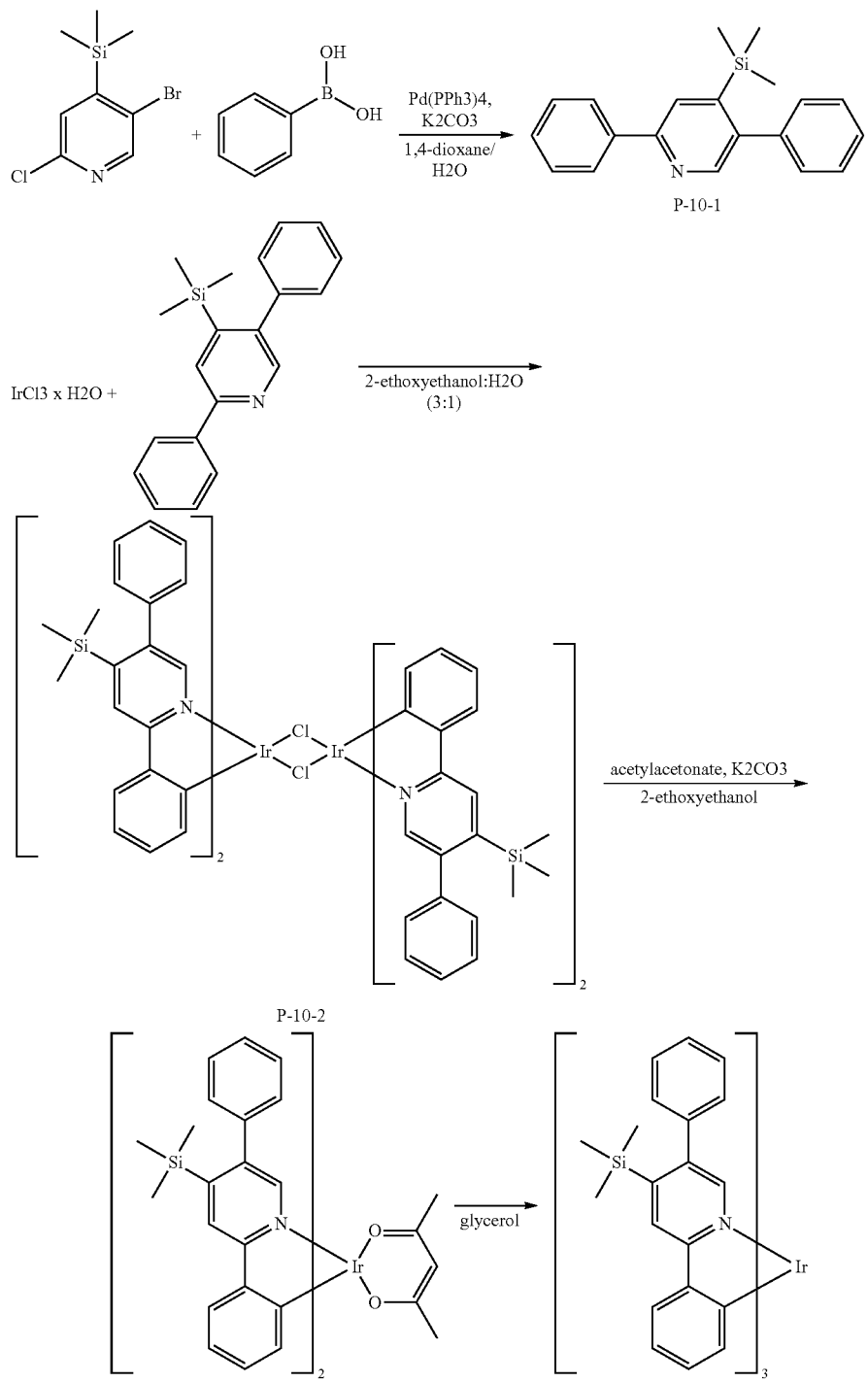

Preparation of Compound P-10-1

130.11 g (491.27 mmol) of 5-bromo-2-chloro-4-trimethylsilylpyridine (AINNOS, ABI Chem, AC2A0F7FP), 118.06 g (968.24 mmol) of phenylboronic acid, 560 mL of THF, 560 mL of toluene, and 560 mL of a 2.5 M-potassium carbonate aqueous solution were mixed in a round-bottomed flask equipped with an agitator having a nitrogen atmosphere, 24.32 g (21.05 mmol) of tetrakistriphenyl phosphine palladium (0) was added thereto, and the mixture was heated and refluxed under a nitrogen stream for 12 hours. When the reaction was terminated, an organic layer was separated, and a solvent therein was all removed. Then, 83.04 g of a compound P-10-1 (a yield: 65%) was obtained through column chromatography.

Preparation of Compound P-10-2

35.57 g (117.22 mmol) of the compound P-10-1, 14.01 g (46.89 mmol) of iridium chloride, 195 mL of 2-ethoxyethanol, and 65 mL of distilled water were put in a 500 mL round-bottomed flask and then, heated and refluxed for 24 hours. When the reaction was terminated, the resultant was cooled down to room temperature, and a solid produced during the reaction was filtered and washed with water and methanol. The solid was dried in a vacuum oven, obtaining 27.5 g of a compound P-10-2 (a yield: 70%).

Preparation of Compound P-10-3

23 g (13.95 mmol) of the compound P-10-2, 3.072 g (30.68 mmol) of 2,4-pentanedione, and 14.78 g (139.47 mmol) of sodium carbonate were put in a 500 mL round-bottomed flask, dissolved in 140 mL of 2-ethoxyethanol, and the solution was heated and refluxed for 5 hours. When the reaction was terminated, the resultant was cooled down to room temperature, and a solid produced therein was filtered. Then, 13 g of a compound P-10-3 (a yield: 52%) was obtained through column chromatography.

Preparation of Compound P-10

6.37 g (40%) of a compound P-10 was synthesized according to the same method as a method of preparing the compound M-1 by using 13 g (14.49 mmol) of the compound P-10-3 and 13.19 g (43.48 mmol) of the compound P-10-1 in a 500 mL round-bottomed flask.

calcd. $C_{60}H_{60}IrN_3Si_3$: C, 65.54; H, 5.50; Ir, 17.48; N, 3.82; Si, 7.66. found: C, 65.62; H, 5.60; N, 3.90.

PREPARATION EXAMPLE 7

Preparation of Compound P-13

[Reaction Scheme 7]

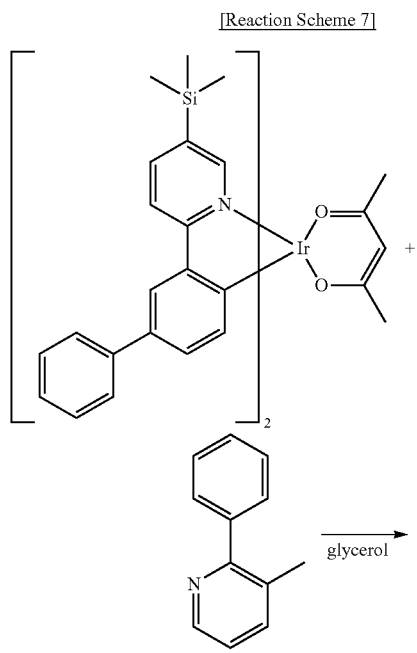

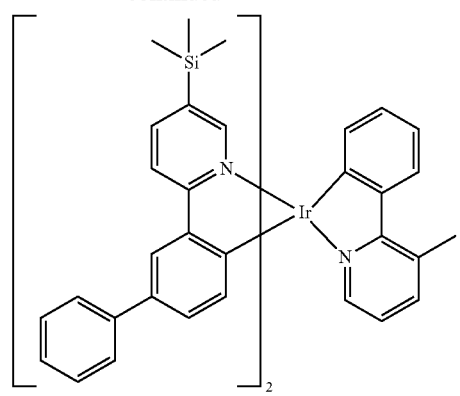

6.13 g (38%) of a compound P-13 was synthesized by using 15 g (16.72 mmol) of the compound 3 according to Preparation Example 1 and 8.49 g (50.17 mmol) of 3-methyl-2-phenylpyridine (TCI M0932) in a 250 mL round-bottomed flask according to the same method as a method of preparing the compound M-1.

calcd. $C_{52}H_{50}IrN_3Si_2$: C, 64.70; H, 5.22; Ir, 19.91; N, 4.35; Si, 5.82. found: C, 64.80; H, 5.27; N, 4.45.

PREPARATION EXAMPLE 8

Preparation of Compound P-14

[Reaction Scheme 8]

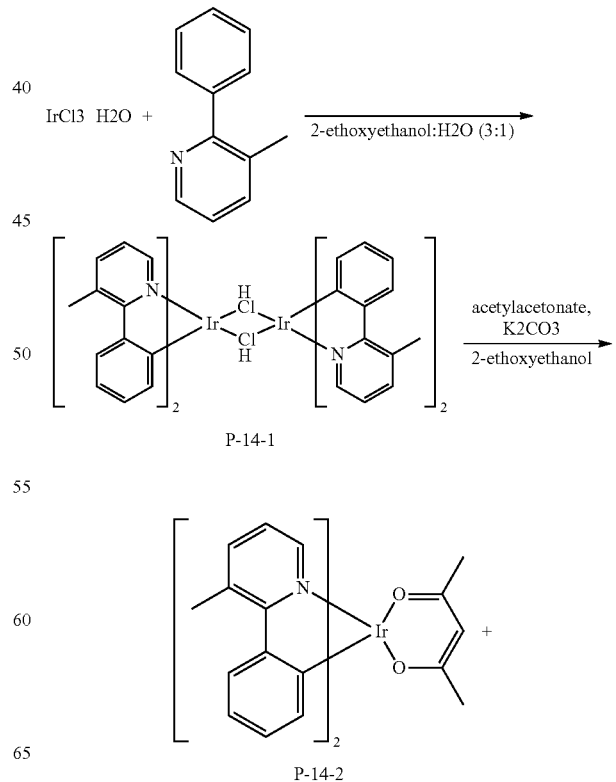

-continued

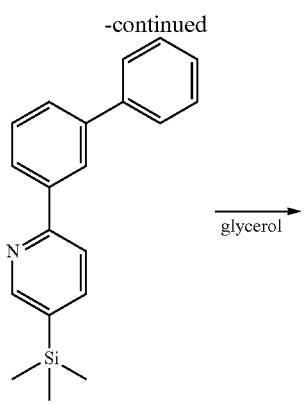

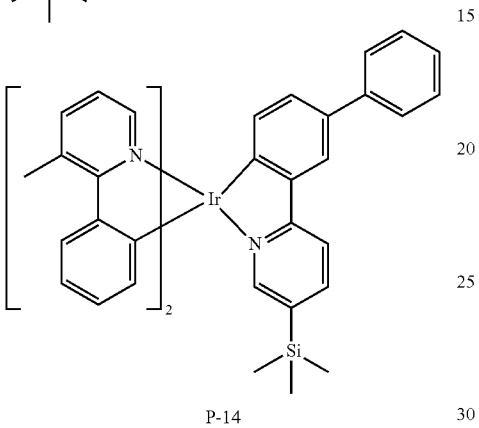

P-14

Preparation of Compound P-14-1

99.12 g (586.11 mmol) of 3-methyl-2-phenylpyridine, 70.0 g (234.44 mmol) of iridium chloride, 976 mL of 2-ethoxyethanol, and 326 mL of distilled water were mixed in a 2 L round-bottomed flask and then, heated and refluxed for 24 hours. When the reaction was terminated, the resultant was cooled down to room temperature, and a solid produced during the reaction was filtered and then, washed with water and methanol. The solid was dried in a vacuum oven, obtaining 90.5 g of a compound P-14-1 (a yield: 68%).

Preparation of Compound P-14-2

90.5 g (80.22 mmol) of the compound P-14-1, 17.67 g (176.48 mmol) of 2,4-pentanedione, and 110.87 g (802.18 mmol) of sodium carbonate were put in a 2 L round-bottomed flask and dissolved in 850 mL of 2-ethoxyethanol, and the solution was heated and refluxed for 5 hours. When the reaction was terminated, the resultant was cooled down to room temperature, and a solid produced therein was filtered. Then, 39.57 g of a compound P-14-2 (a yield: 51%) was obtained through column chromatography.

Preparation of Compound P-14

24.13 g of a compound P-14 (36%) was synthesized by using 39 g (80.64 mmol) of the compound P-14-2 and 73.42 g (241.92 mmol) of the compound 1 according to Preparation Example 1 in a 1 L round-bottomed flask according to the same method as a method of preparing the compound M-1.

calcd. $C_{44}H_{40}IrN_3Si$: C, 63.59; H, 4.85; Ir, 23.13; N, 5.06; Si, 3.38. found: C, 63.68; H, 4.93; N, 5.13.

(Manufacture of Organic Light Emitting Diode)

COMPARATIVE EXAMPLE 1

A glass substrate coated with 1500 Å-thick ITO (indium tin oxide) was ultrasonic wave-washed with a distilled water. When the washing with distilled water was terminated, the coated glass substrate was ultrasonic wave-washed with a solvent such as isopropyl alcohol, acetone, methanol and the like, dried, delivered to a plasma cleaner, cleaned for 5 minutes by using an oxygen plasma, and delivered to a vacuum depositor. The ITO transparent electrode was used as an anode, and HTM (N-(biphenyl-4-yl)-9,9-diphenyl-N-(4-(9-phenyl-9H-carbazole)-3-yl)phenyl) 9H-fluorene-2-amine) represented by the following Chemical Formula Z-1 was vacuum-deposited on the ITO substrate to form a 1200 Å-thick hole injection layer (HIL).

[Chemical Formula Z-1]

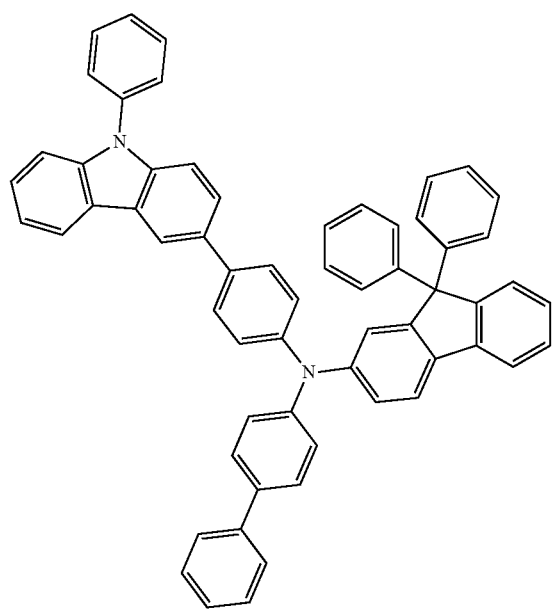

On the hole transport layer (HTL), a 300 Å-thick emission layer was formed by using CBP as a host and doping the host with 7 wt % of PhGD (tris(3-methyl-2-pyridine) iridium) represented by the following Chemical Formula Z-2 as a green phosphorescent dopant.

[Chemical Formula Z-2]

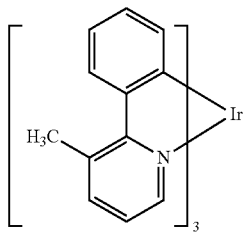

On the emission layer, 50 Å-thick BAlq (bis(2-methyl-8-quinolinolato-N1,O8)-(1,1'-biphenyl-4-olato)aluminum)) represented by the following Chemical Formula Z-3 and 250 Å-thick Alq3 (tris(8-hydroxyquinolinato)aluminium) represented by the following Chemical Formula Z-4 were sequentially stacked to form an electron transport layer (ETL). On the electron transport layer (ETL), 5 Å-thick LiF and 1000 Å-thick Al were sequentially vacuum-deposited to form a cathode, preparing an organic light emitting diode.

[Chemical Formula Z-3]

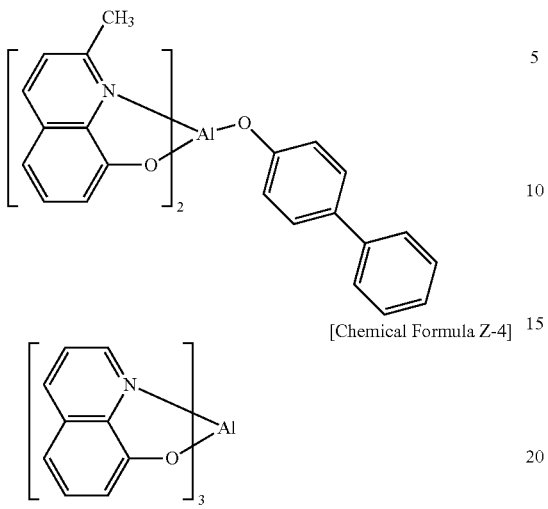

[Chemical Formula Z-4]

COMPARATIVE EXAMPLE 2

An organometallic compound represented by the following Chemical Formula T-1 was manufactured according to the same method as a method used in Preparation Example 1 in order to compare characteristics of the compounds according to the present invention, and an organic light emitting diode was manufactured according to the same method as a method used in Comparative Example 1 except for using 10 wt % of the compound represented by the following Chemical Formula T-1 instead of PhGD represented by the above Chemical Formula Z-2 as a green phosphorescent dopant.

[Chemical Formula T-1]

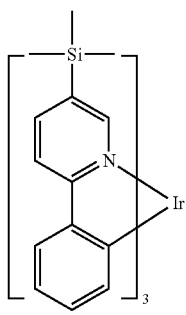

EXAMPLE 1

An organic light emitting diode was manufactured according to the same method as a method used in Comparative Example 1 except for using 10 wt % of the compound M-1 according to Preparation Example 1 instead of PhGD represented by the above Chemical Formula Z-2 as a green phosphorescent dopant.

EXAMPLE 2

An organic light emitting diode was manufactured according to the same method as Example 1 except for using the dopant according to Preparation Example 2 instead of the dopant according to Preparation Example 1.

EXAMPLE 3

An organic light emitting diode was manufactured according to the same method as Example 1 except for using the dopant according to Preparation Example 3.

EXAMPLE 4

An organic light emitting diode was manufactured according to the same method as Example 1 except for using the dopant according to Preparation Example 4.

EXAMPLE 5

An organic light emitting diode was manufactured according to the same method as Example 1 except for using the dopant according to Preparation Example 5.

EXAMPLE 6

An organic light emitting diode was manufactured according to the same method as Example 1 except for using the dopant according to Preparation Example 6.

EXAMPLE 7

An organic light emitting diode was manufactured according to the same method as Example 1 except for using the dopant according to Preparation Example 7.

EXAMPLE 8

An organic light emitting diode was manufactured according to the same method as Example 1 except for using the dopant according to Preparation Example 8.

(Performance Measurement of Organic Light Emitting Diode)

Current density change and luminance change of each organic light emitting diode according to the Examples 1 to 8 and Comparative Examples 1 and 2 depending on a voltage were measured, and thus luminous efficiency and life-span characteristics were evaluated. Specific measurement methods are as follows, and the results are shown in the following Table 1.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

The luminance, current density, and voltage obtained from the (1) and (2) were used to calculate current efficiency (cd/A) at the same luminance (9000 cd/m$^2$).

(4) Measurement of Life-span

A decreasing time of luminous efficiency by 3% was measured maintaining luminance (cd/m$^2$) at 6000 cd/m$^2$.

TABLE 1

| | Chemical Formula | Luminous efficiency (cd/A) | Device life-span (h) T97 (%) at 6000 nit |
|---|---|---|---|
| Comparative Example 1 | Z-2 | 46 | 2 |
| Comparative Example 2 | T-1 | 46.8 | <10 min |
| Example 1 | M-1 | 55 | 52 |
| Example 2 | P-2 | 49 | 47 |
| Example 3 | P-3 | 48 | 50 |
| Example 4 | P-11 | 47 | 40 |
| Example 5 | P-12 | 46.1 | 45 |
| Example 6 | P-10 | 46.8 | 40 |
| Example 7 | P-13 | 50.6 | 42 |
| Example 8 | P-14 | 51.3 | 41 |

As shown in Table 1, the organic light emitting diodes manufactured by using a material provided in the present invention showed much excellent luminous efficiency and life-span. The result shows that the compound according to the present invention may be used as a preferable material for an organic light emitting diode.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

[Description of Symbols]

| | |
|---|---|
| 100: organic light emitting diode | 110: cathode |
| 120: anode | 105: organic thin layer |
| 130: emission layer | 140: hole transport layer (HTL) |
| 230: emission layer + electron transport layer (ETL) | |

The invention claimed is:

1. A compound for an organic optoelectric device, the compound being represented by the following Chemical Formula 1:

[Chemical Formula 1]

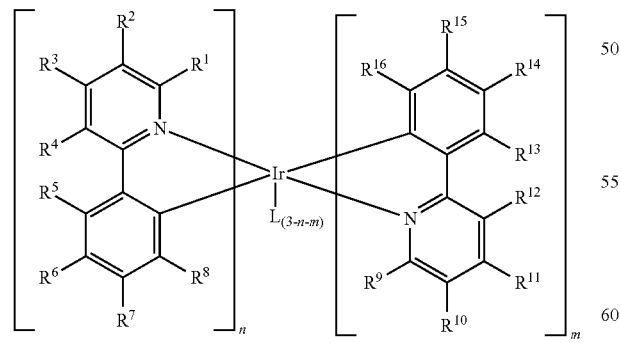

wherein, in the above Chemical Formula 1,
$R^1$ to $R^{16}$ are independently hydrogen, a C1 to C10 alkyl group, a C6 to C20 aryl group, or —$SiR^{17}R^{18}R^{19}$, where $R^{17}$ to $R^{19}$ are independently a C1 to C6 alkyl group, provided that one of $R^1$ to $R^8$ is a functional group represented by the following Chemical Formula 2, and another of $R^1$ to $R^8$ is —$SiR^{17}R^{18}R^{19}$, and provided that one of $R^9$ to $R^{16}$ is a functional group represented by the following Chemical Formula 2, and another of $R^9$ to $R^{16}$ is —$SiR^{17}R^{18}R^{19}$, L is one of the follwing Chemical Formulae L-1 to L-14:

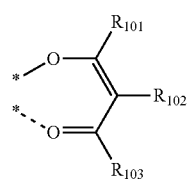
[L-1]

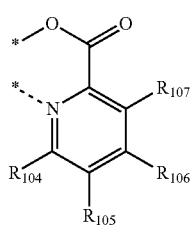
[L-2]

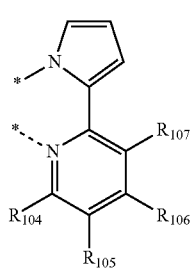
[L-3]

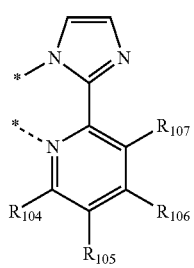
[L-4]

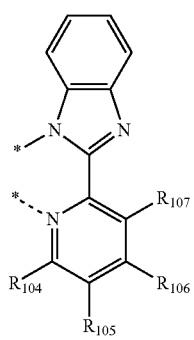
[L-5]

-continued
[L-6]
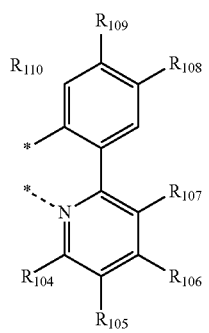
[L-7]
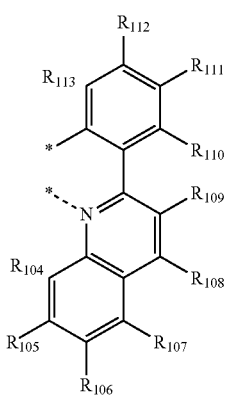
[L-8]
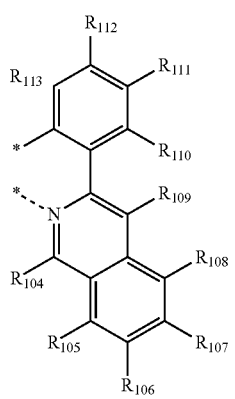
[L-9]
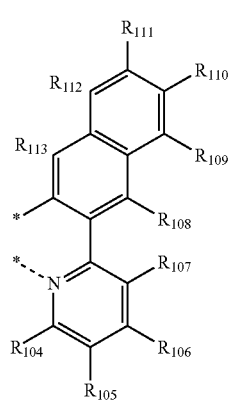
-continued
[L-10]
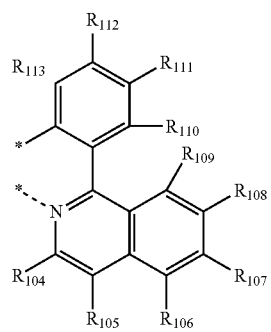
[L-11]
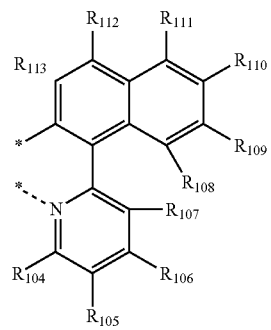
[L-12]
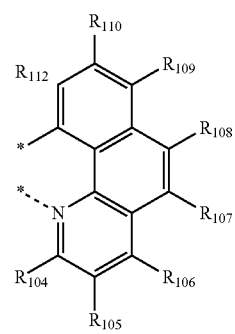
[L-13]
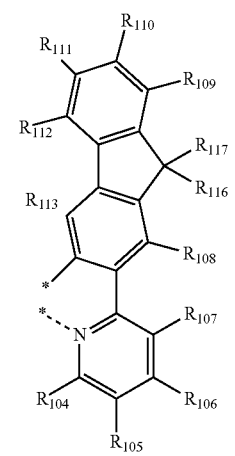

-continued

[L-14]

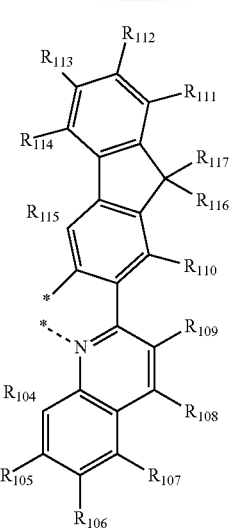

wherein, in the above Chemical Formulae L-1 to L-14, the asterisk (*) denotes a position bonding with iridium, $R_{101}$ to $R_{103}$ are independently hydrogen, a C1 to C30 alkyl group that is unsubstituted or substituted with a halogen, a C6 to C30 aryl group that is unsubstituted or substituted with a C1 to C30 alkyl group, or a halogen, $R_{104}$ to $R_{115}$ are independently hydrogen, a halogen, a C1 to C30 alkyl group, a C6 to C30 aryl group, a trialkylsilyl group having C1 to C30 alkyl groups, or a triarylsilyl group having C6 to C30 aryl groups, and $R_{116}$ to $R_{117}$ are independently hydrogen, a C1 to C30 alkyl group that is unsubstituted or substituted with a halogen, or a C6 to C30 aryl group that is unsubstituted or substituted with a C1 to C30 alkyl group, and n and m are independently integers of 0 to 3, and n+m is an integer of 1 to 3,

[Chemical Formula 2]

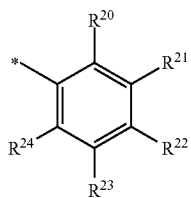

wherein, in the above Chemical Formula 2, $R^{20}$ to $R^{24}$ are independently hydrogen, a C1 to C10 alkyl group, or a C6 to C20 aryl group, and

* denotes a bonding position with a carbon atom.

2. The compound for an organic optoelectric device of claim 1, wherein, in the above Chemical Formula 1, n is an integer of 1 to 3, one of $R^1$ to $R^4$ is —SiR$^{17}$R$^{18}$R$^{19}$, and the rest of $R^1$ to $R^4$ are independently hydrogen, or a C1 to C10 alkyl group, and one of $R^5$ to $R^8$ is the functional group represented by the above Chemical Formula 2, and the rest of $R^5$ to $R^8$ are independently hydrogen, or a C1 to C10 alkyl group.

3. The compound for an organic optoelectric device of claim 1, wherein, in the above Chemical Formula 1, n is an integer of 1 to 3, one of $R^1$ to $R^4$ is the functional group represented by the above Chemical Formula 2, and another of $R^1$ to $R^4$ is —SiR$^{17}$R$^{18}$R$^{19}$, and the rest of $R^1$ to $R^4$ and $R^5$ to $R^8$ are independently hydrogen, or a C1 to C10 alkyl group.

4. The compound for an organic optoelectric device of claim 1, wherein, in the above Chemical Formula 1, $R^{17}$ to $R^{19}$ are each a methyl group.

5. The compound for an organic optoelectric device of claim 1, wherein, in the above Chemical Formula 1, n is an integer of 1 to 3, $R^2$ is —SiR$^{17}$R$^{18}$R$^{19}$, $R^6$ is a phenyl group, and $R^1$, $R^3$ to $R^5$, $R^7$, and $R^8$ are independently hydrogen, or a C1 to C10 alkyl group.

6. The compound for an organic optoelectric device of claim 1, wherein, in the above Chemical Formula 1, n is an integer of 1 to 3, $R^2$ is a phenyl group, $R^3$ is —SiR$^{17}$R$^{18}$R$^{19}$, and $R^1$ and $R^4$ to $R^8$ are independently hydrogen, or a C1 to C10 alkyl group.

7. The compound for an organic optoelectric device of claim 1, wherein, in the above Chemical Formula 1, n+m is 3.

8. The compound for an organic optoelectric device of claim 1, wherein, in the above Chemical Formula 1, n+m is 1 or 2.

9. A compound for an organic optoelectric device, the compound being represented by one of the following Chemical Formulae M-1 to M-40, Chemical Formulae P-1 to P-26, or Chemical Formulae Q-1 to Q-46:

[Chemical Formula M-1]

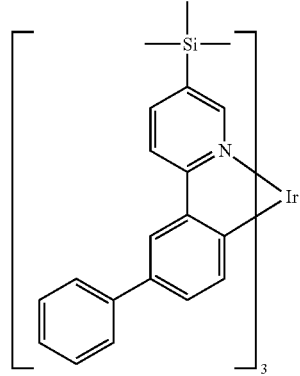

[Chemical Formula M-2]

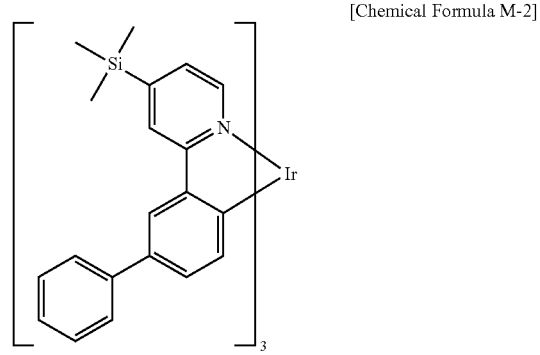

[Chemical Formula M-3]
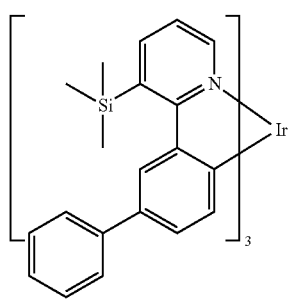
[Chemical Formula M-4]
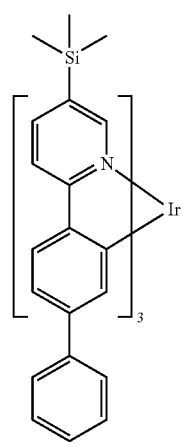
[Chemical Formula M-5]
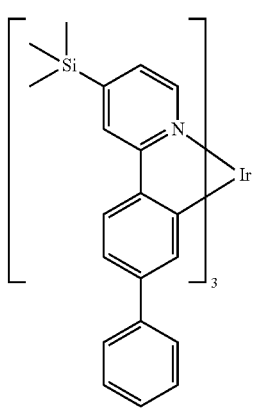
[Chemical Formula M-6]
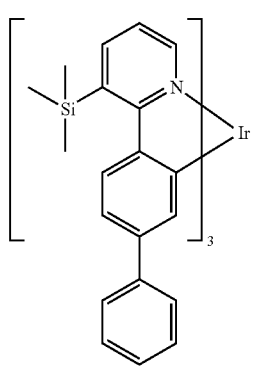
[Chemical Formula M-7]
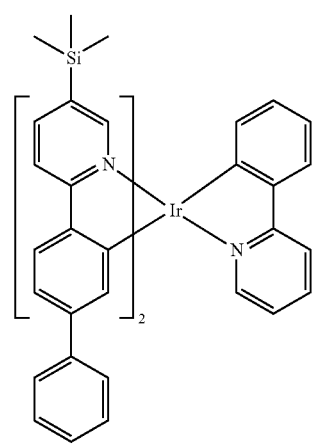
[Chemical Formula M-8]
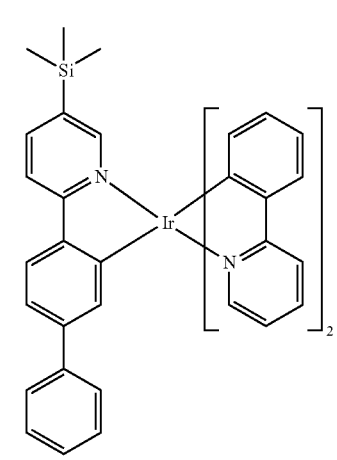
[Chemical Formula M-9]
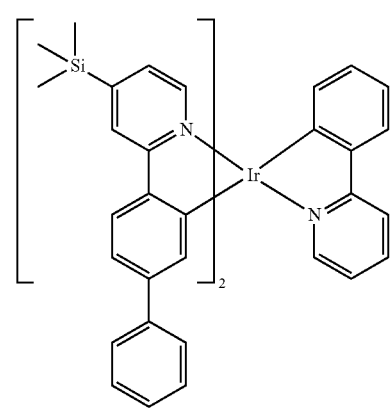

[Chemical Formula M-10]
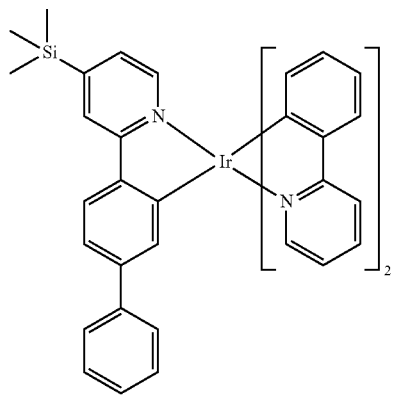
[Chemical Formula M-11]
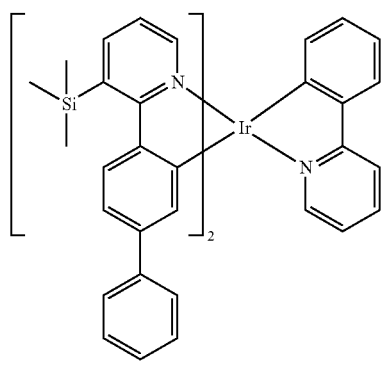
[Chemical Formula M-12]
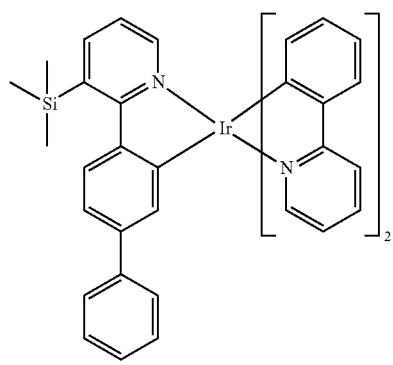
[Chemical Formula M-13]
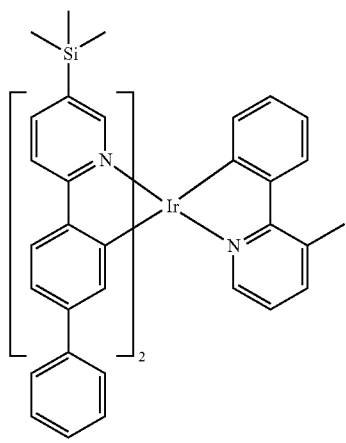
[Chemical Formula M-14]
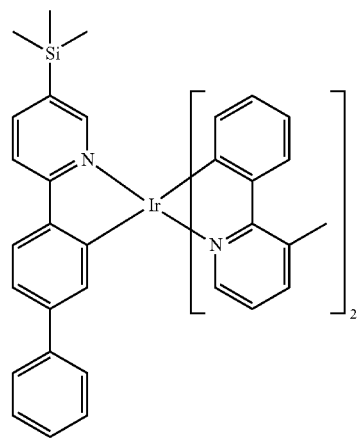
[Chemical Formula M-15]
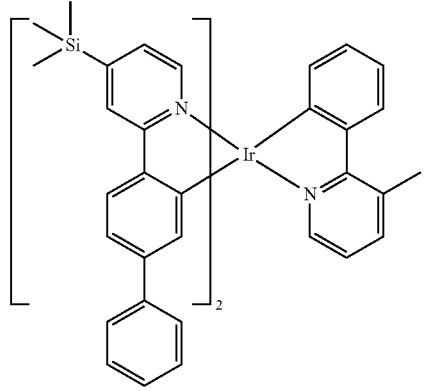
Chemical Formula M-16
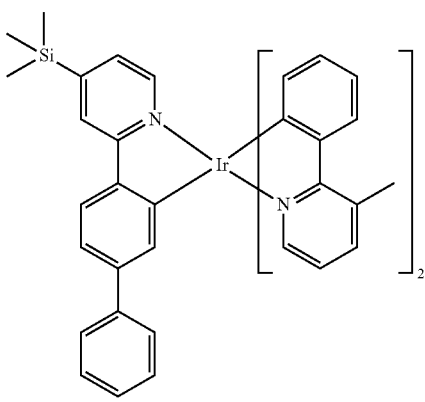

[Chemical Formula M-17]
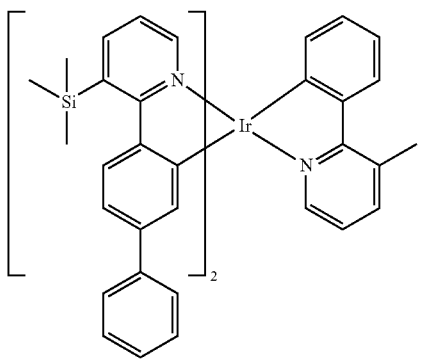
[Chemical Formula M-18]
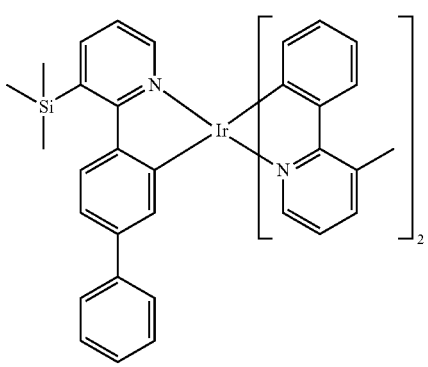
[Chemical Formula M-19]
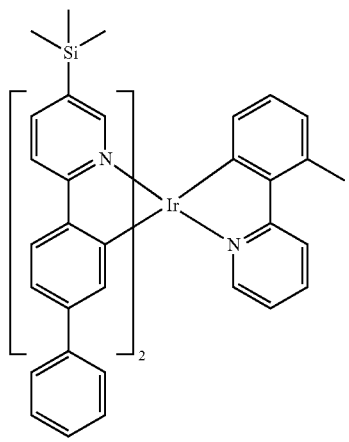
[Chemical Formula M-20]
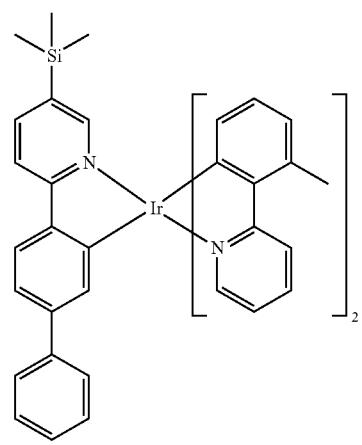
[Chemical Formula M-21]
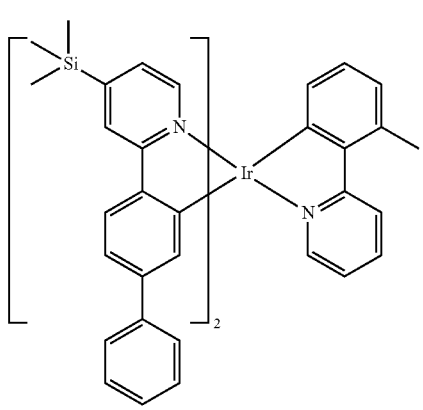
[Chemical Formula M-22]
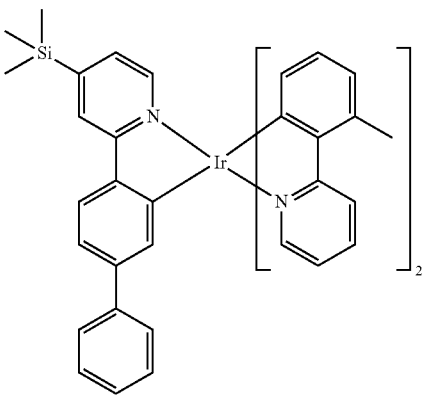
[Chemical Formula M-23]
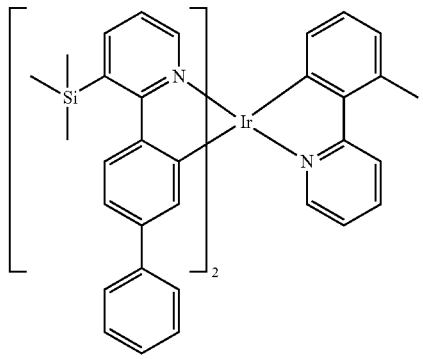
[Chemical Formula M-24]
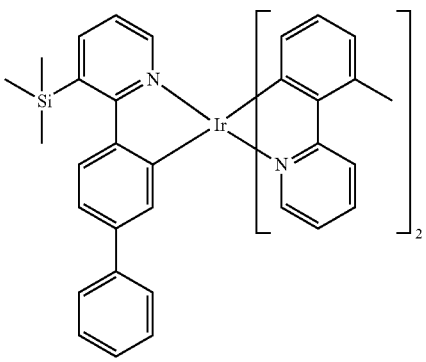

[Chemical Formula M-25]
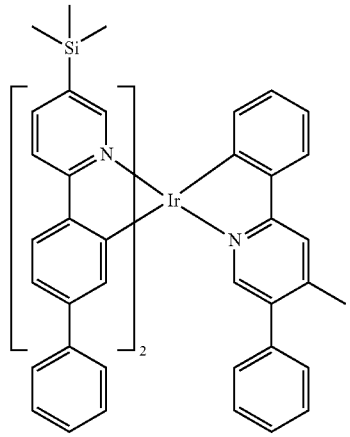
[Chemical Formula M-26]
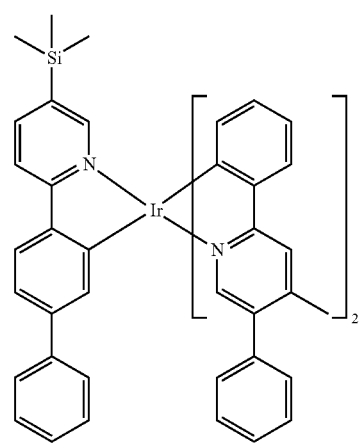
[Chemical Formula M-27]
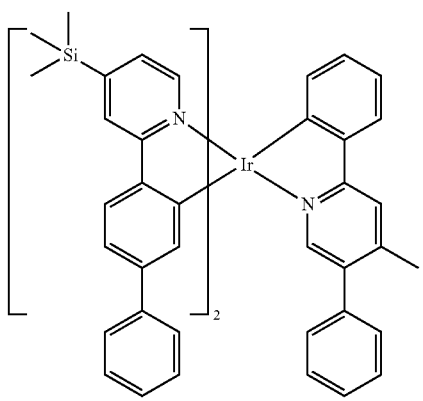
[Chemical Formula M-28]
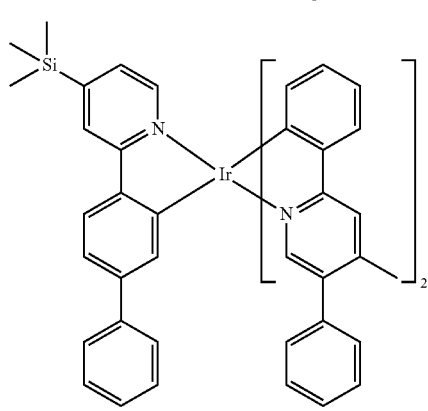
[Chemical Formula M-29]
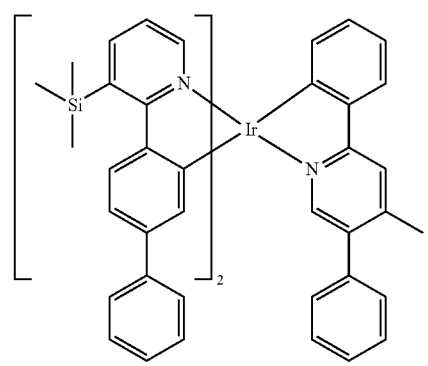
[Chemical Formula M-30]
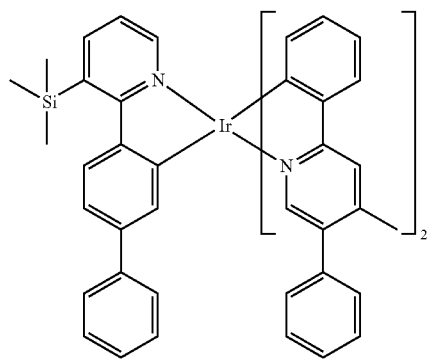
[Chemical Formula M-31]
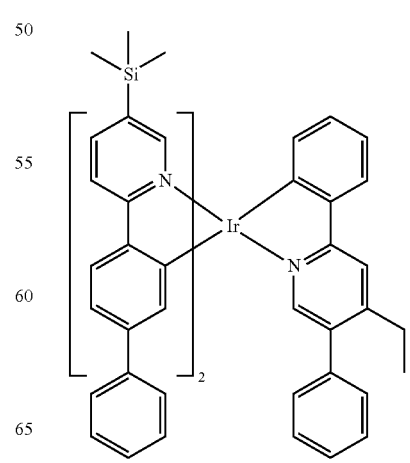

[Chemical Formula M-32]
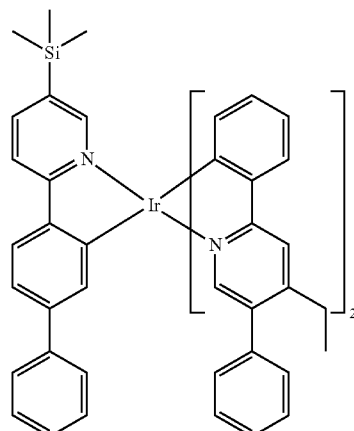
[Chemical Formula M-33]
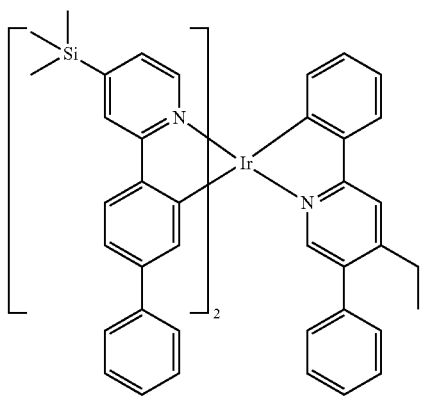
[Chemical Formula M-34]
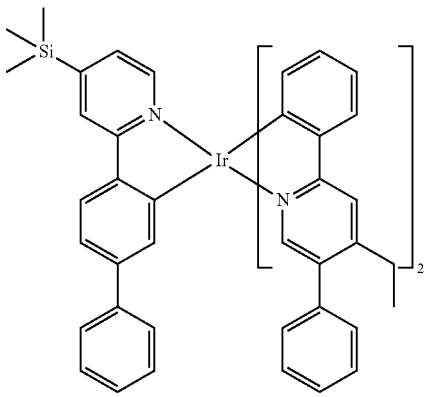
[Chemical Formula M-35]
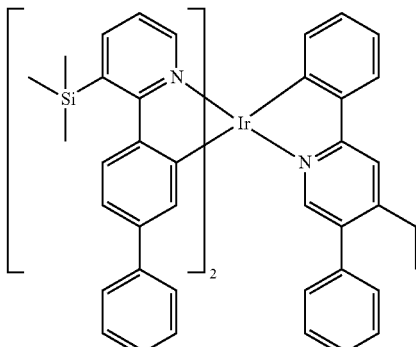
[Chemical Formula M-36]
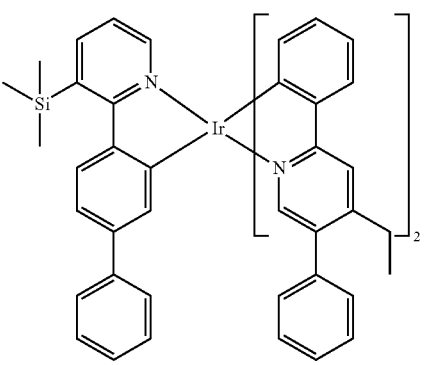
[Chemical Formula M-37]
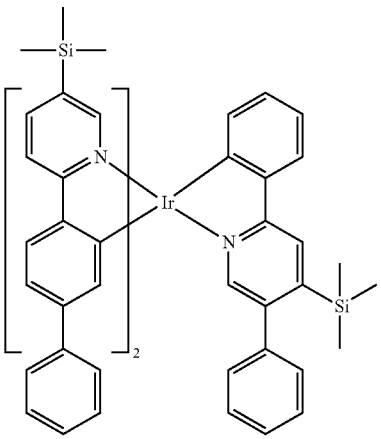

[Chemical Formula M-38]
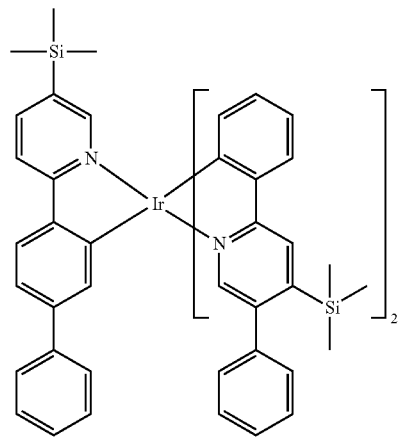
[Chemical Formula M-39]
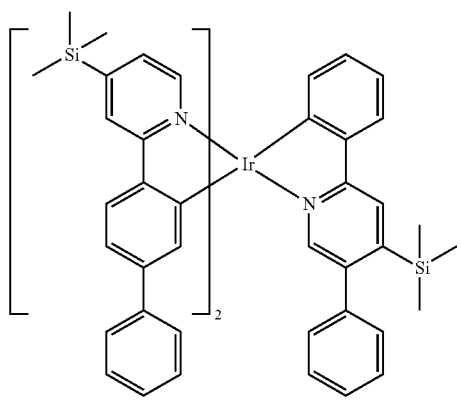
[Chemical Formula M-40]
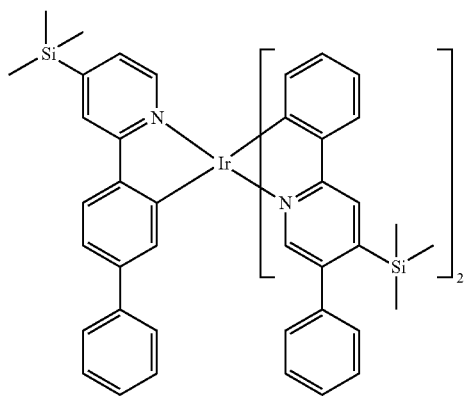
[Chemical Formula P-1]
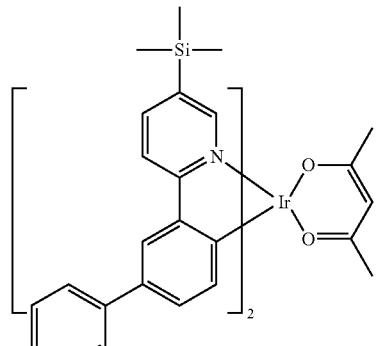
[Chemcial Formula P-2]
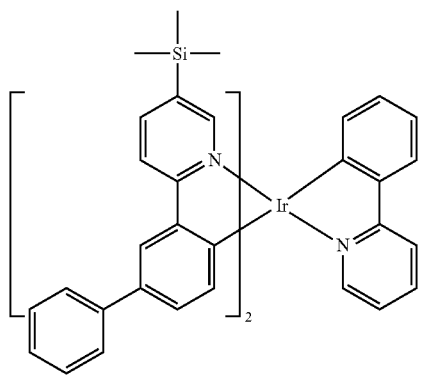
[Chemical Formula P-3]
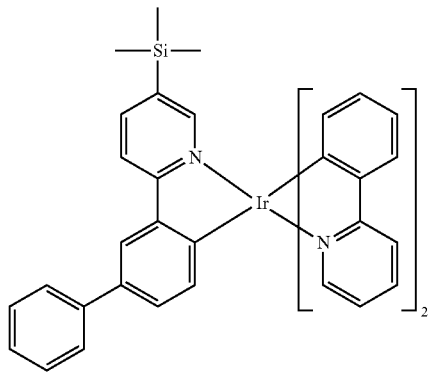
[Chemical Formula P-4]
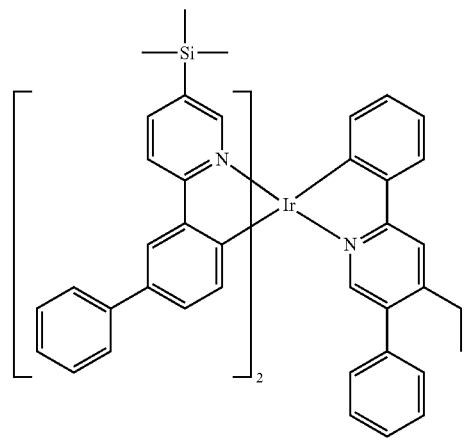

[Chemical Formula P-5]
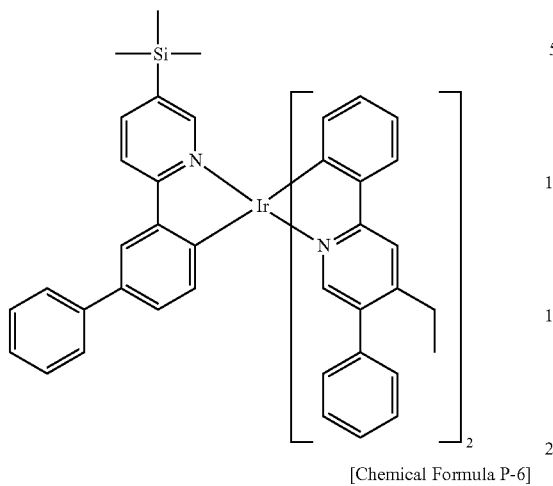
[Chemical Formula P-6]
[Chemical Formula P-7]
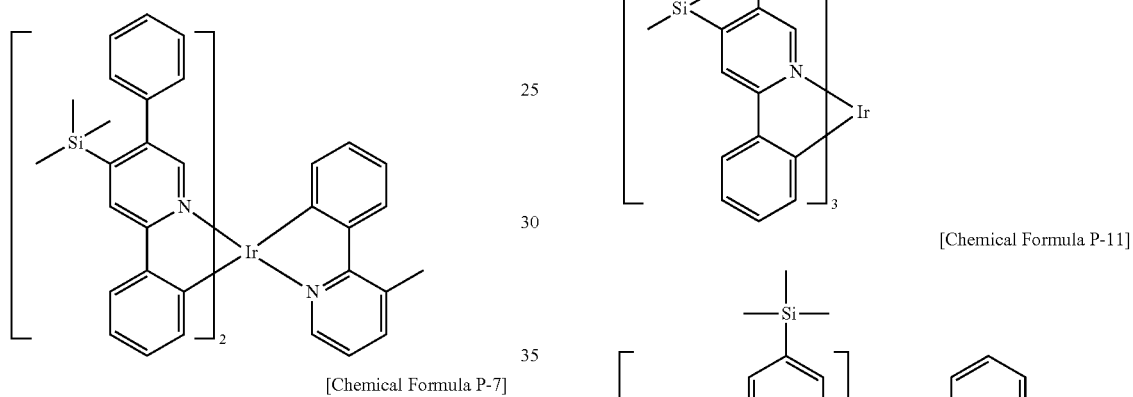
[Chemcial Formula P-8]
[Chemical Formula P-9]
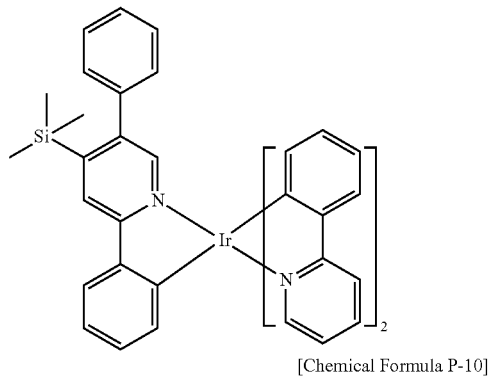
[Chemical Formula P-10]
[Chemical Formula P-11]
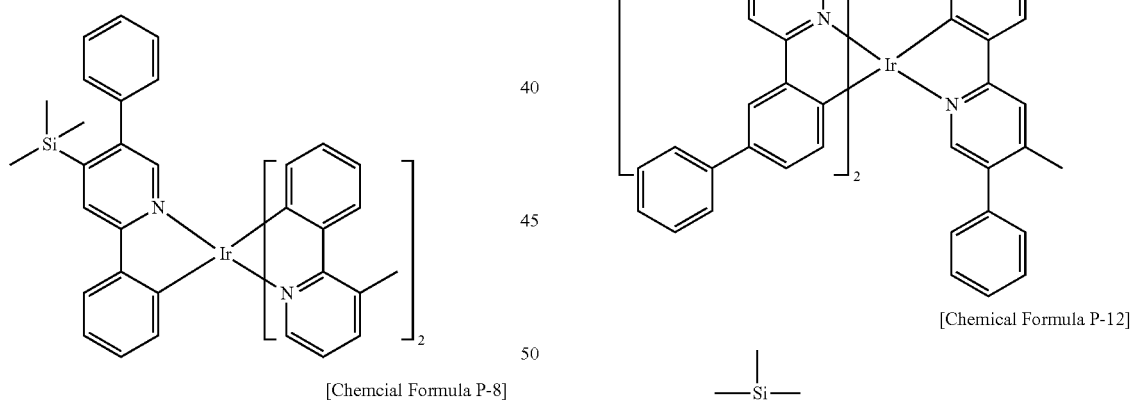
[Chemical Formula P-12]
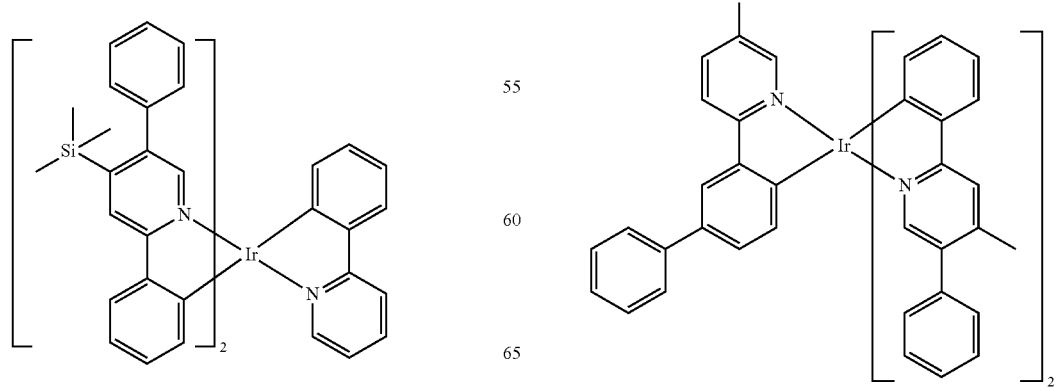

[Chemical Formula P-13]
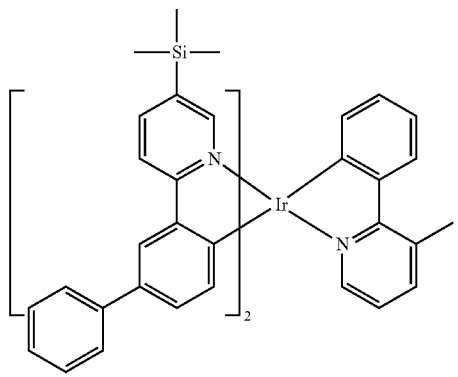
[Chemical Formula P-14]
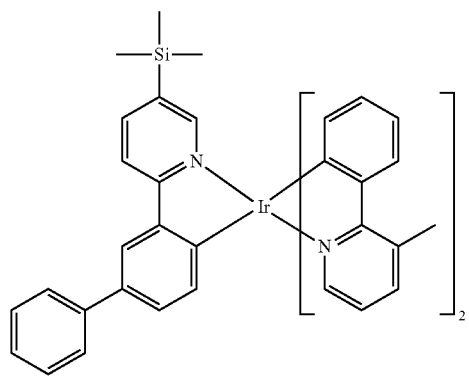
[Chemical Formula P-15]
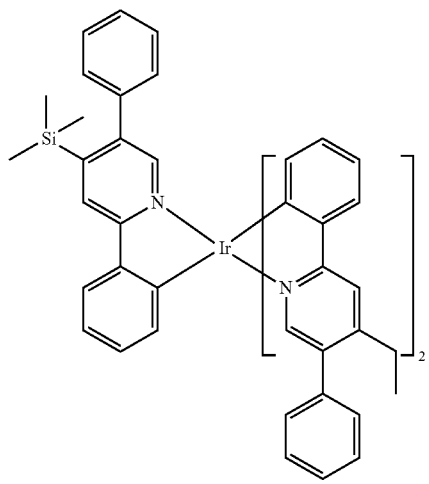
[Chemical Formula P-16]
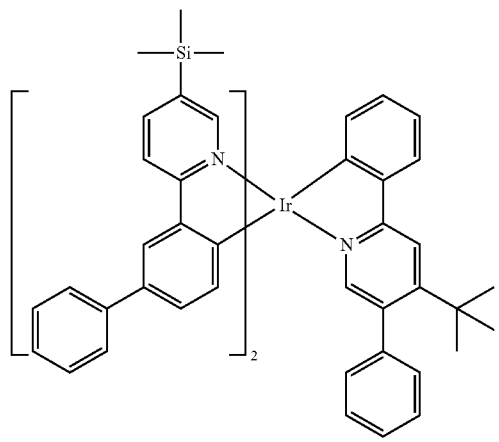
[Chemical Formula P-17]
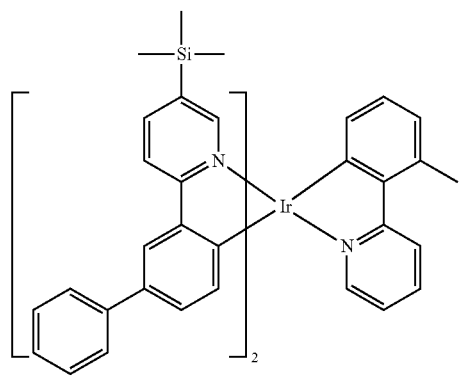
[Chemical Formula P-18]
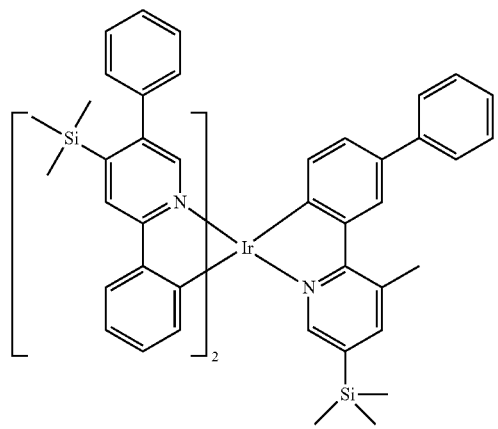

[Chemical Formula P-19]
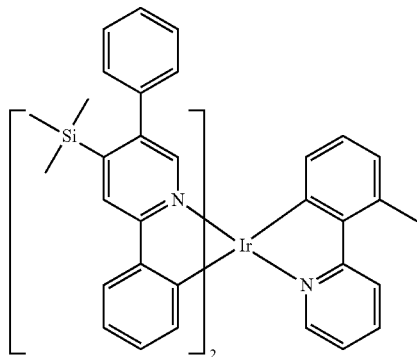
[Chemical Formula P-20]
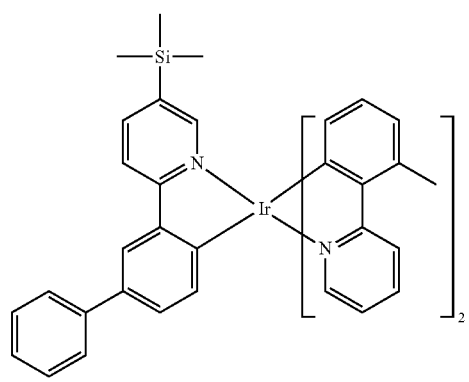
[Chemical Formula P-21]
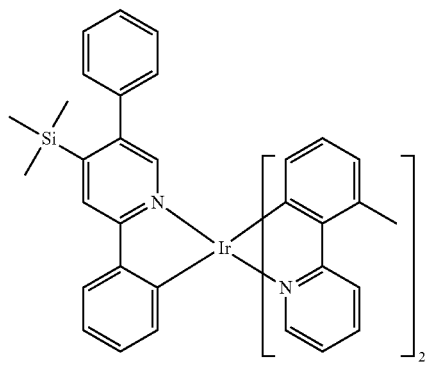
[Chemical Formula P-22]
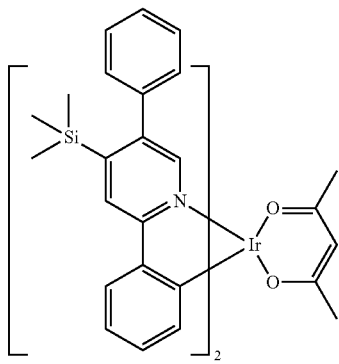
[Chemical Formula P-23]
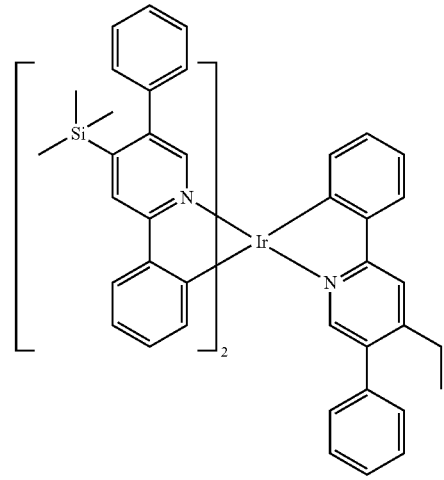
[Chemical Formula P-24]
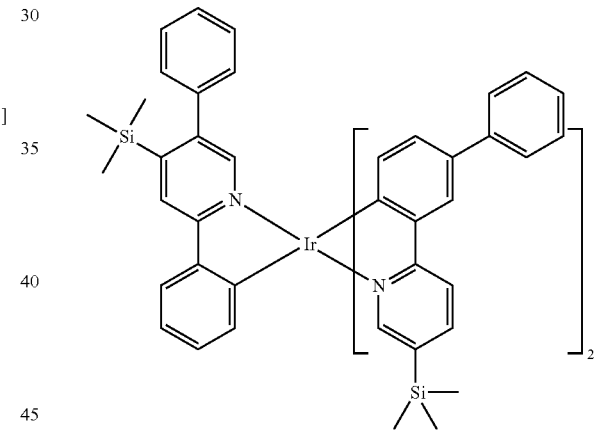
[Chemical Formula P-25]
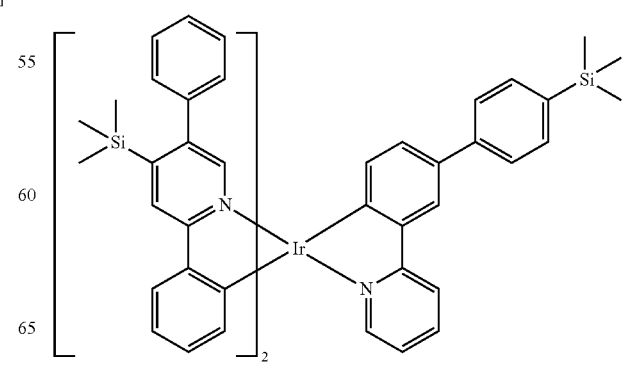

[Chemical Formula P-26]
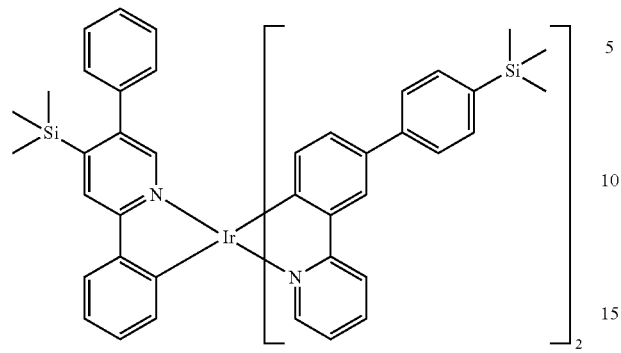
[Chemical Formula Q-1]
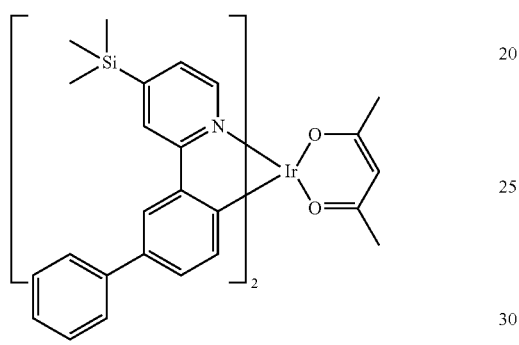
[Chemical Formula Q-2]
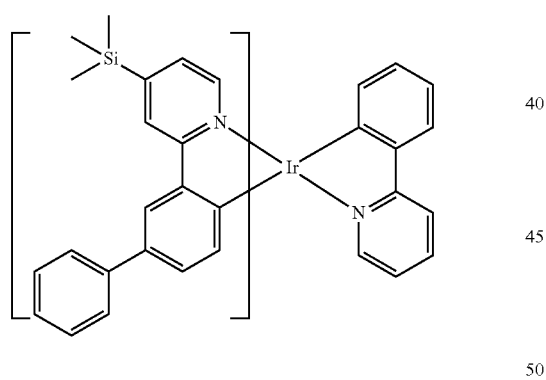
[Chemical Formula Q-3]
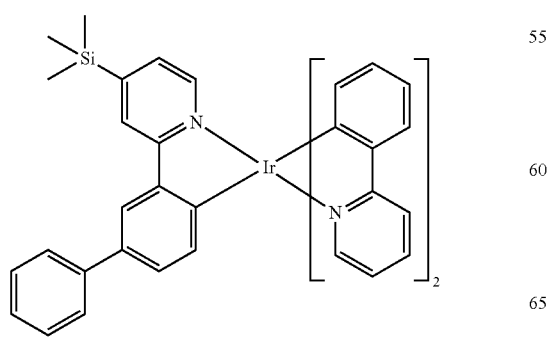
[Chemical Formula Q-4]
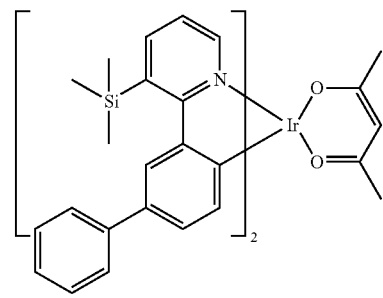
[Chemical Formula Q-5]
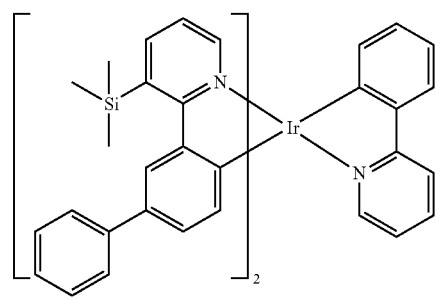
[Chemical Formula Q-6]
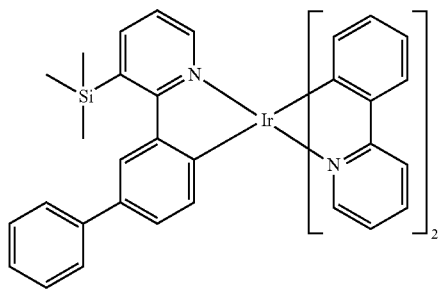
[Chemical Formuula Q-7]
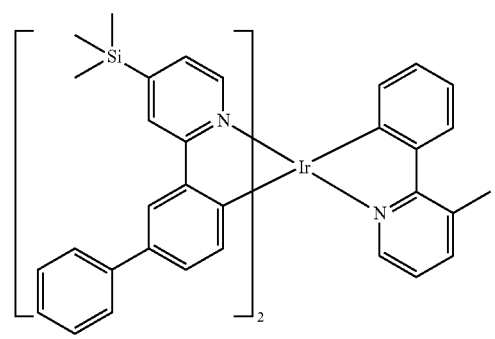

[Chemical Formula Q-8]
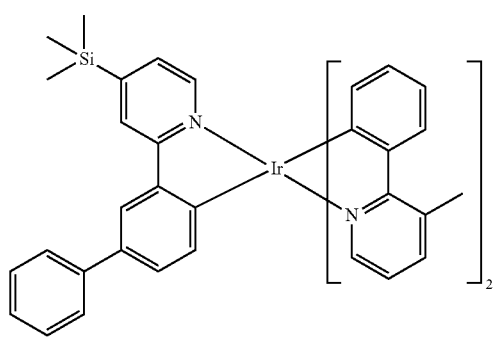
[Chemical Formula Q-9]
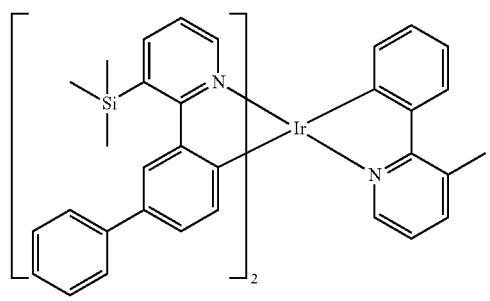
[Chemical Formula Q-10]
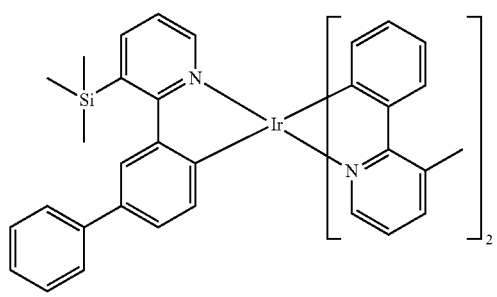
[Chemical Formula Q-11]
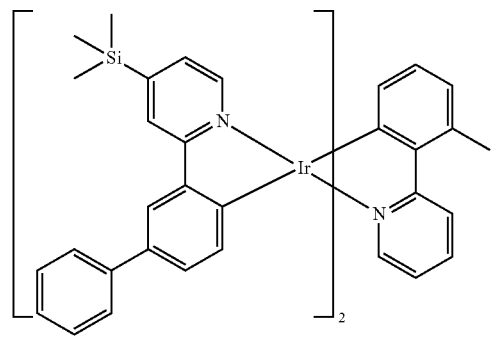
[Chemical Formula Q-12]
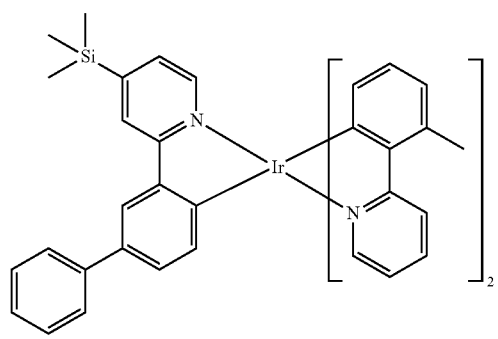
[Chemical Formula Q-13]
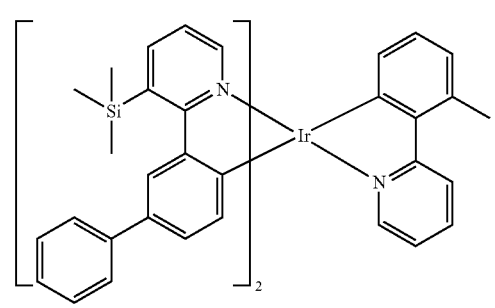
[Chemical Formula Q-14]
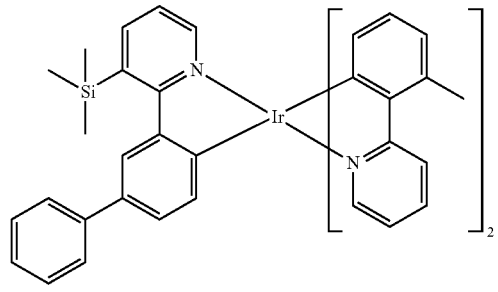
[Chemical Formula Q-15]
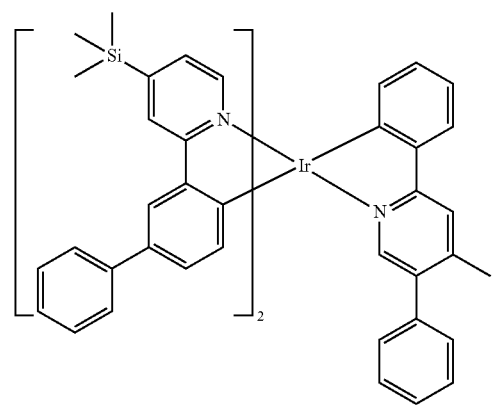

[Chemical Formula Q-16]
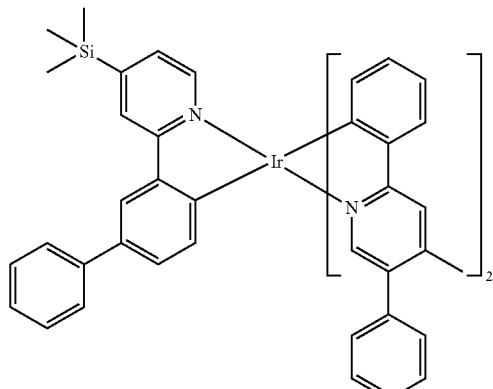
[Chemical Formula Q-17]
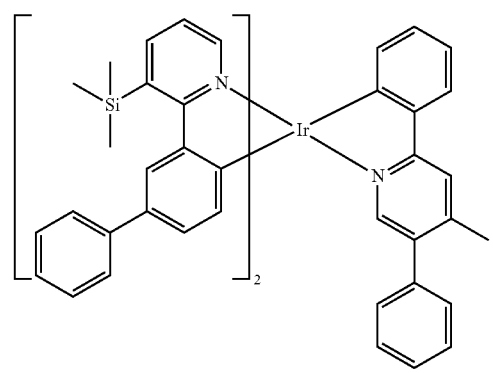
[Chemical Formula Q-18]
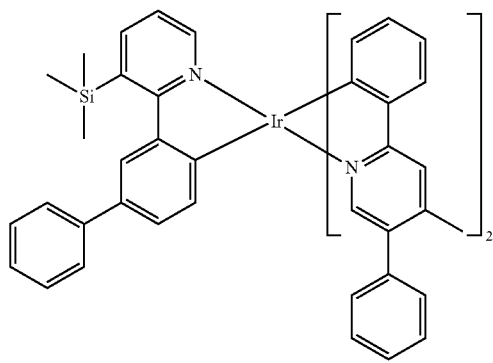
[Chemical Formula Q-19]
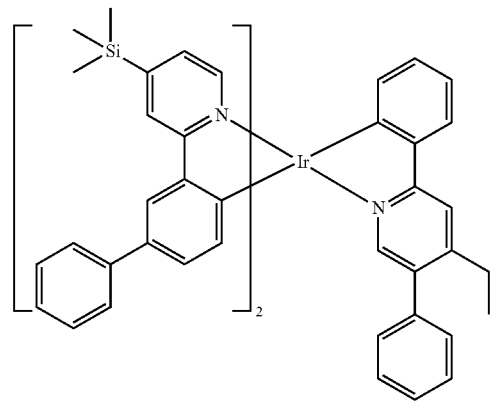
[Chemical Formula Q-20]
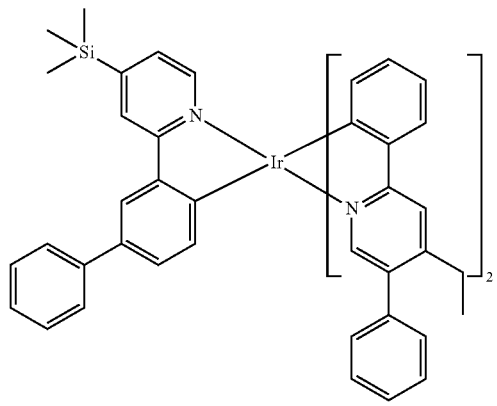
[Chemical Formula Q-21]
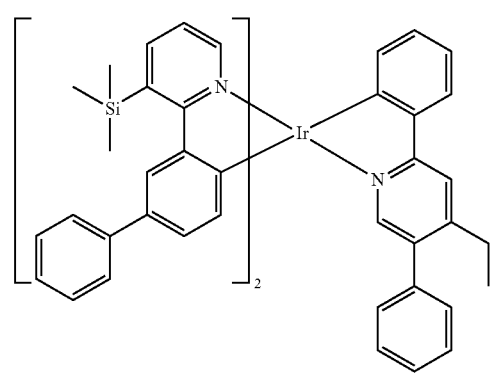
[Chemical Formula Q-22]
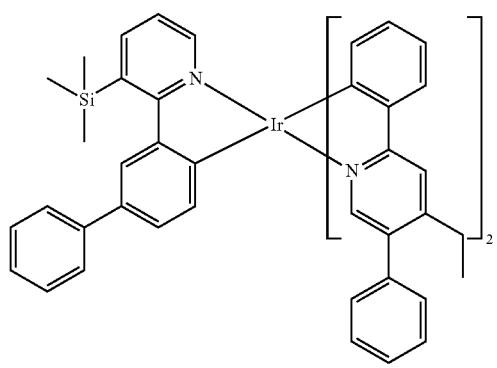
[Chemical Formula Q-23]
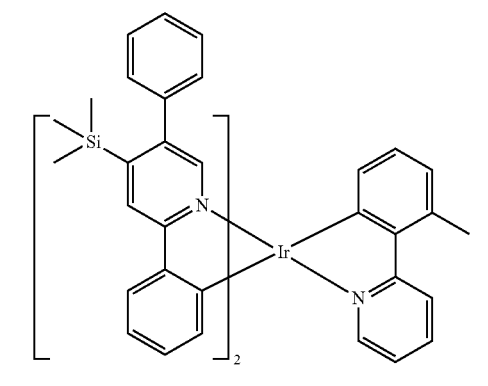

-continued
[Chemical Formula Q-24]
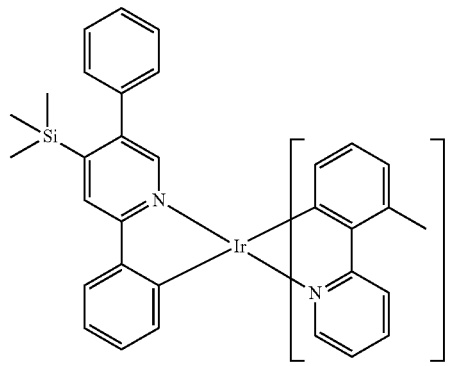
[Chemical Formula Q-25]
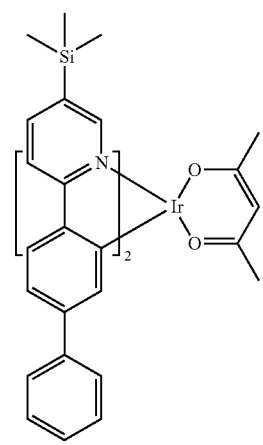
[Chemical Formula Q-26]
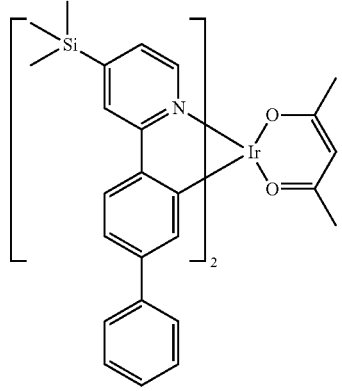
[Chemical Formula Q-27]
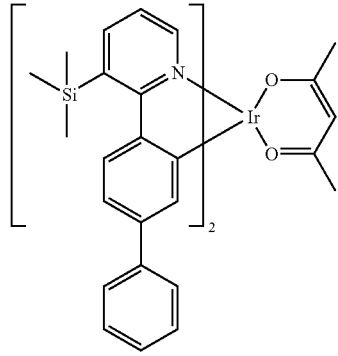
-continued
[Chemical Formula Q-28]
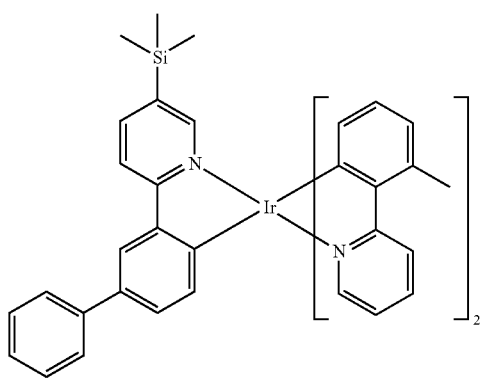
[Chemical Formula Q-29]
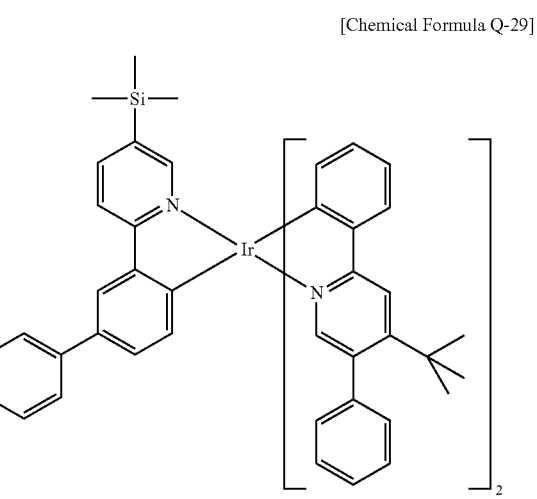
[Chemical Formula Q-30]
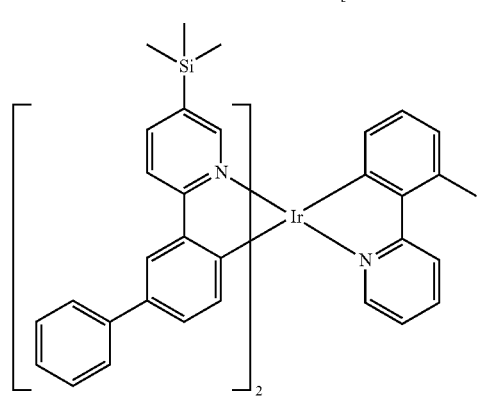

[Chemical Formula Q-31]
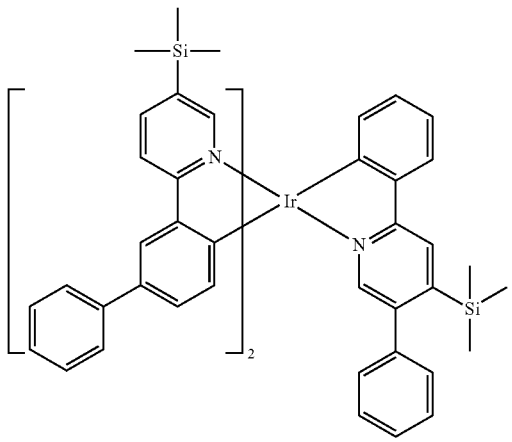
[Chemical Formula Q-32]
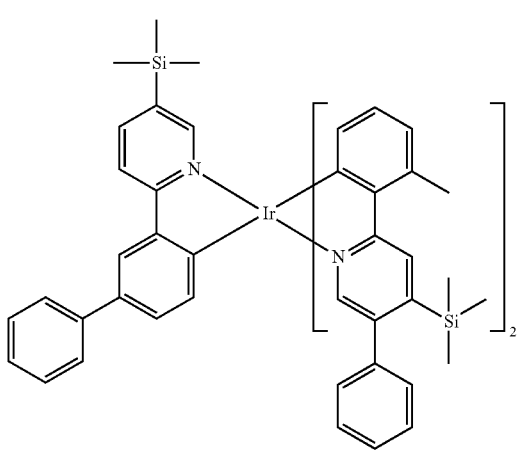
[Chemical Formula Q-33]
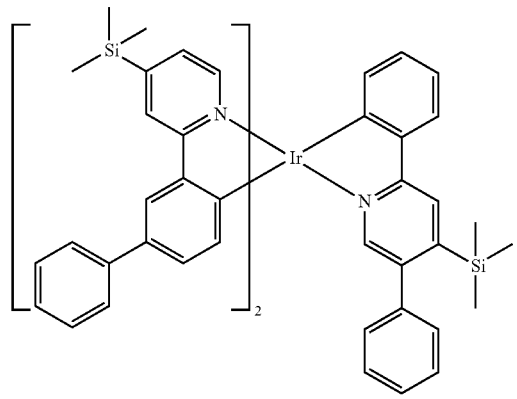
[Chemical Formula Q-34]
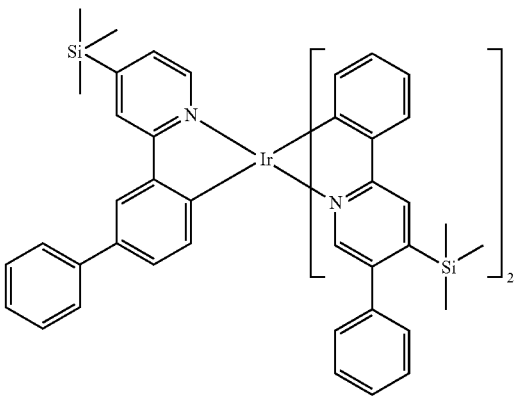
[Chemical Formula Q-35]
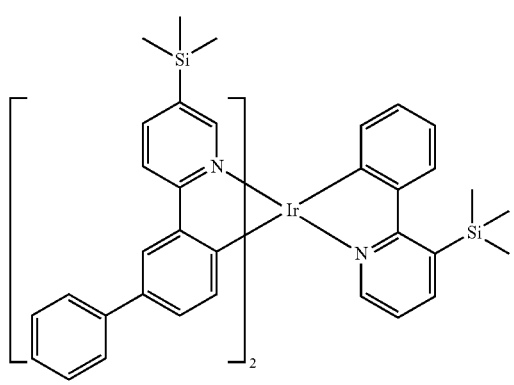
[Chemical Formula Q-36]
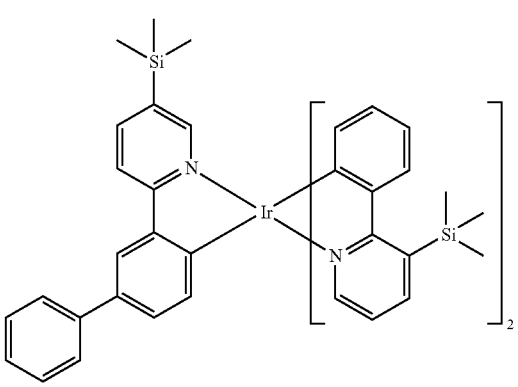
[Chemical Formula Q-37]
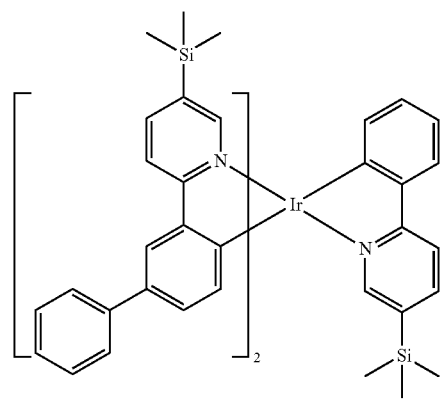

[Chemical Formula Q-38]
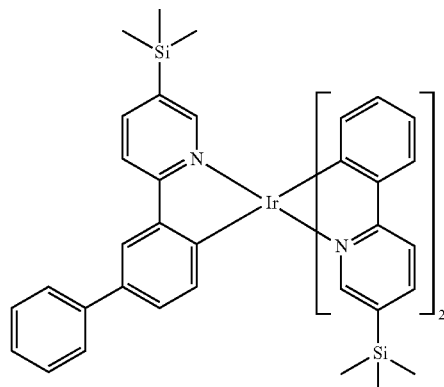
[Chemical Formula Q-39]
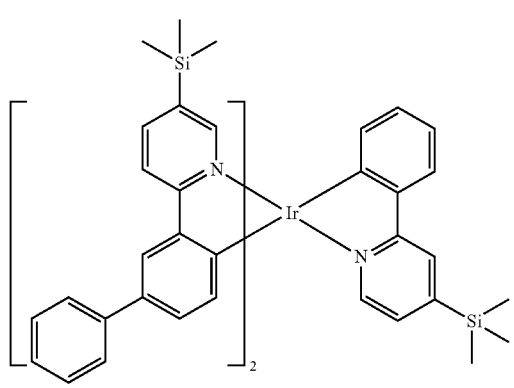
[Chemical Formula Q-40]
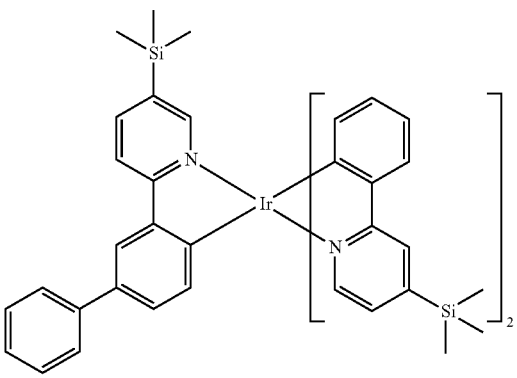
[Chemical Formula Q-41]
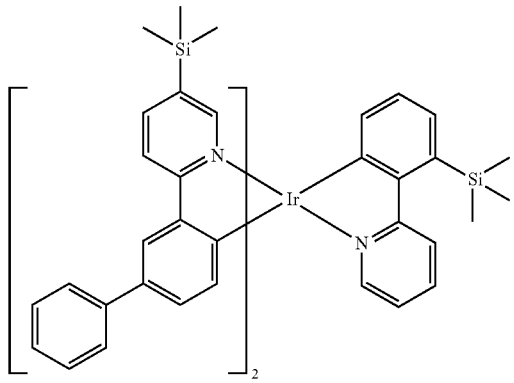
[Chemical Formula Q-42]
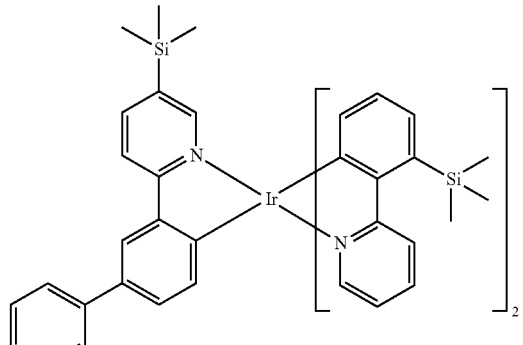
[Chemical Formula Q-43]
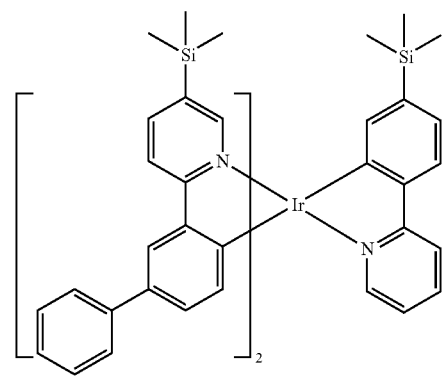
[Chemical Formula Q-44]
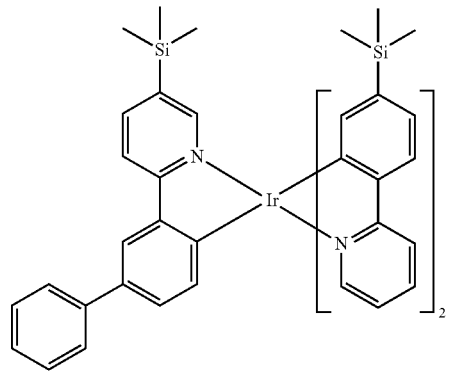
[Chemical Formula Q-45]
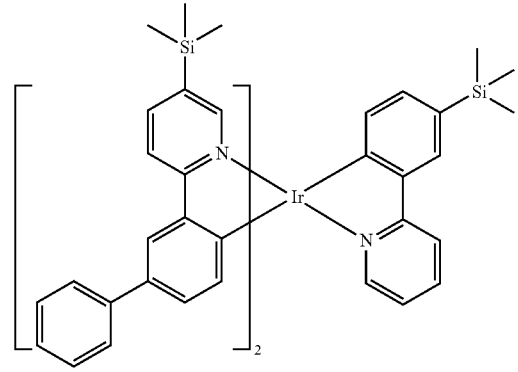

-continued

[Chemical Formula Q-46]

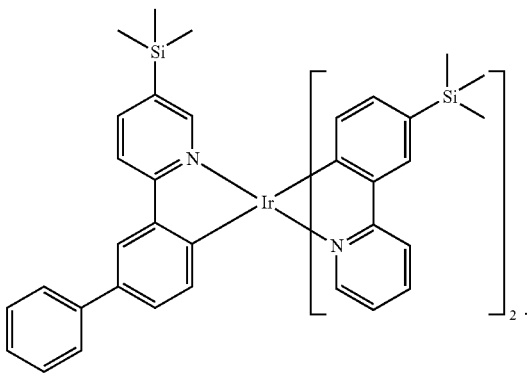

10. An organic light emitting diode, comprising:
an anode, a cathode, and
an organic thin layer interposed between the anode and the cathode,
wherein the organic thin layer includes the compound for an organic optoelectric device of claim 1.

11. The organic light emitting diode of claim 10, wherein the organic thin layer is an emission layer.

12. The organic light emitting diode of claim 11, wherein the compound for an organic optoelectric device is used as a dopant in the emission layer.

13. A display device comprising the organic light emitting diode of claim 10.

14. The compound for an organic optoelectric device of claim 1, wherein, in Chemical Formula 1,
$R^1$ to $R^{16}$ are independently hydrogen, a C1 to C10 alkyl group, a C6 to C20 aryl group, or —$SiR^{17}R^{18}R^{19}$, where $R^{17}$ to $R^{19}$ are independently a C1 to C6 alkyl group,
provided that one of $R^5$ to $R^8$ is a functional group represented by Chemical Formula 2, and one of $R^1$ to $R^4$ is —$SiR^{17}R^{18}R^{19}$, and
provided that one of $R^{13}$ to $R^{16}$ is a functional group represented by Chemical Formula 2, and one of $R^9$ to $R^{12}$ is —$SiR^{17}R^{18}R^{19}$.

* * * * *

UNITED STATES PATENT AND TRADEMARK OFFICE
CERTIFICATE OF CORRECTION

PATENT NO. : 9,882,149 B2
APPLICATION NO. : 14/390570
DATED : January 30, 2018
INVENTOR(S) : Hyung-Sun Kim et al.

It is certified that error appears in the above-identified patent and that said Letters Patent is hereby corrected as shown below:

On the Title Page

Item (54) and in the Specification, Column 1, Lines 1-6, should read -- COMPOUND FOR ORGANIC OPTOELECTRIC DEVICE, ORGANIC OPTOELECTRIC DEVICE COMPRISING SAME, AND DISPLAY APPARATUS COMPRISING ORGANIC OPTOELECTRIC DEVICE --.

Signed and Sealed this
Twenty-fifth Day of June, 2019

Andrei Iancu
*Director of the United States Patent and Trademark Office*